(12) United States Patent
Grant et al.

(10) Patent No.: US 11,976,113 B2
(45) Date of Patent: May 7, 2024

(54) BIOPHARMACEUTICAL COMPOSITIONS COMPRISING NUCLEIC ACIDS ENCODING IL-5 BINDING PROTEINS

(71) Applicant: GLAXOSMITHKLINE INTELLECTUAL PROPERTY DEVELOPMENT LIMITED, Middlesex (GB)

(72) Inventors: Steven Grant, Stevenage (GB); Martin Orecchia, Stevenage (GB); Chika Akinseye, Stevenage (GB); Laura Hook, Stevenage (GB); Alan Lewis, Stevenage (GB); Tejinder Bhinder, Stevenage (GB)

(73) Assignee: GLAXOSMITHKLINE INTELLECTUAL PROPERTY DEVELOPMENT LIMITED, Stevenage (GB)

(*) Notice: Subject to any disclaimer, the term of this patent is extended or adjusted under 35 U.S.C. 154(b) by 526 days.

(21) Appl. No.: 16/988,257

(22) Filed: Aug. 7, 2020

(65) Prior Publication Data
US 2021/0017269 A1    Jan. 21, 2021

Related U.S. Application Data

(62) Division of application No. 15/987,942, filed on May 24, 2018, now Pat. No. 10,787,509.

(60) Provisional application No. 62/511,441, filed on May 26, 2017.

(51) Int. Cl.
*C07K 16/24* (2006.01)
*A61K 39/395* (2006.01)
*A61K 39/00* (2006.01)

(52) U.S. Cl.
CPC ........ *C07K 16/244* (2013.01); *A61K 39/3955* (2013.01); *A61K 2039/505* (2013.01); *C07K 2317/24* (2013.01); *C07K 2317/33* (2013.01); *C07K 2317/51* (2013.01); *C07K 2317/515* (2013.01); *C07K 2317/52* (2013.01); *C07K 2317/524* (2013.01); *C07K 2317/565* (2013.01); *C07K 2317/567* (2013.01); *C07K 2317/71* (2013.01); *C07K 2317/72* (2013.01); *C07K 2317/76* (2013.01); *C07K 2317/90* (2013.01); *C07K 2317/92* (2013.01); *C07K 2317/94* (2013.01)

(58) Field of Classification Search
CPC .......................... C07K 16/244; A61K 39/3955
See application file for complete search history.

(56) References Cited

U.S. PATENT DOCUMENTS

| 9,334,331 B2* | 5/2016 | Igawa ..................... C07K 16/36 |
| 10,421,807 B2* | 9/2019 | Gonzales ................ A61P 11/00 |
| 10,787,509 B2 | 9/2020 | Grant et al. |
| 11,111,292 B2 | 9/2021 | Liddament et al. |

FOREIGN PATENT DOCUMENTS

| AU | 2008 201 419 A1 | 4/2008 |
| CN | 1175263 A | 3/1998 |
| CO | 2018001840 A2 | 5/2018 |
| EP | 1749840 A2 | 2/2007 |
| JP | 2013-091636 A | 5/2013 |
| JP | 2017-055771 A | 3/2017 |
| WO | 1996021000 A2 | 7/1996 |
| WO | 2008134721 A1 | 11/2008 |
| WO | 2008134724 A2 | 11/2008 |
| WO | 2009120927 A2 | 10/2009 |
| WO | 2012/083370 A1 | 6/2012 |
| WO | WO 2017/033121 A1 | 3/2017 |
| WO | 2018119016 A1 | 6/2018 |
| WO | 2019224724 A1 | 11/2019 |

OTHER PUBLICATIONS

Bork et al, Genome Res. 2000 10: 398-400.*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Rabia, et al. (2018, Biochemical Engineering Journal 137:365-374).*
Brummell et al., Biochemistry 32: 1180-1187, 1993.*
Skolnick et al., 2000, Trends in Biotech. 18(1):34-39.*
Paul, William E., Fundamental Immunology, 3rd Edition, Raven Press, New York, Chapt. 8, pp. 292-295 (1993).*
Casset et al (Biochemical and Biophysical Research Communications, 307:198-205, 2003).*
Doerks et al., 1998, Trends in Genetics 14:248-250.*
Smith et al., 1997, Nature Biotechnology 15:1222-1223.*
Brenner, 1999, Trends in Genetics 15:132-133.*
Tokuriki et al. (Current Opinion in Structural Biology 19: 596-604, 2009.*
Fenton et al. (Medicinal Chemistry Research 29:1133-1146, 2020.*
Bhattacharya et al. (PLoS ONE 12(3): e0171355, 2017).*
Wu et al. (J Mol Biol. 294: 151-162, 1999).*
Sela-Culang et al. (Front Immunol 4: 302, 2013).*
Kobayashi et al., Protein Engineering 12: 879-844, 1999.*
Burks et al., PNAS 94: 412-417, 1997.*
Brorson et al. J Immunol 163: 6694-6701.*
Colman, Res Immunol 145: 33-36, 1994.*
Zhang et al. (mAbs 7(1): 42-52, 2015.*
Vasudevan et al., Blood Cell Mol Dis 32: 176-181, 2004.*
Vajdos et al. (J Mol Biol. 320: 415-428, 2002).*
Holm et al. (Mol Immunology 44: 1075-1084, 2007.*
Chen et al. (J Mol Biol. 293: 865-881, 1999)/.*
Guo et al. (PNAS USA 101(25):9205-10, 2004).*

(Continued)

*Primary Examiner* — Zachary C Howard
(74) *Attorney, Agent, or Firm* — Cynthia Lan Martin

(57) ABSTRACT

The present disclosure relates to compositions, for treating interleukin 5 (IL-5) mediated diseases, and related methods.

16 Claims, 9 Drawing Sheets

Specification includes a Sequence Listing.

(56) References Cited

OTHER PUBLICATIONS

Bridgeman, Mary Barna, "Mepolizumab (Nucala) for Severe Eosinophilic Asthma", Oct. 31, 2016, Retrieved from the Internet: URL:https://www.ncbi.nlm.nih.gov/pmc/articles/PMC5046999/pdf/ptj4110619.pdf [retrieved on Jul. 18, 2018].

Elgert, K.D., "Immunology: Understanding the Immune System", New York: Wiley-Liss, Inc., pp. 58-63 (1996).

Hoogenboom HR, "Designing and optimizing library selection strategies for generating high-affinity antibodies", Trends in Biotechnology, Elsevier Publications, Cambridge, GB, vol. 15, No. 2, Feb. 1, 1997, pp. 62-70, ISSN: 0167-7799, DOI: 10.1016/S0167-7799(97)84205-9.

Liddament M. et al, "PI55 Higher binding affinity and in-vitro potency of reslizumab for interleukin-5 compared with mepolizumab", A Annals of Allergy, Asthma & Immunology, vol. 117, No. 5, Nov. 30, 2016, ISSN: 1081-1206, DOI: 10.1016/J.ANAI.2016.09.166.

Andersen, et al., "Nucleic acid secondary structures containing the double-headed nucleoside 5'(S)-C-(2-(thymin-1-yl)ethyl)thymidine", Organic & Biomolecular Chemistry, vol. 6, No. 21, 2008, p. 3983.

Koizumi, M., et al., "Biologically active oligodeoxyribonucleotides. Part 12:/\N/\-Methylation of 2'-deoxyguanosines enhances stability of parallel G-quadruplex and anti-HIV-1 activity", Bioorganic & Medicinal Chemistry Letters, vol. 10, No. 19, Oct. 2, 2000, pp. 2213-2216.

Liu, et al, "Recovery and purification process development for monoclonal antibody production", MABS, (Sep. 9, 2010), vol. 2, No. 5, pp. 480-499.

Manali, Mukherjee et al, "Anti-IL5 therapy for asthma and beyond", World Allergy Organization Journal, Biomed Central Ltd, London, UK, (Dec. 4, 2014), vol. 7, No. 1, p. 32.

Sørensen et al., "Synthesis of conformationally restricted dinucleotides by ring-closing metathesis", Organic Letters, vol. 2, No. 26, Dec. 28, 2000, pp. 4217-4219.

Tyther Raymond et al, "Quality Issues Arising from Post-translational Modification of Recombinant Antibodies", Antibody Expression and Production, pp. 293-303, (Jan. 1, 2011).

Wang, et al., "Biophysical and biochemical properties of oligodeoxynucleotides containing 4'-C- and 5'-C-substituted thymidines", Bioorg Med Chem Lett., Mar. 22, 1999;9(6):885-90.

\* cited by examiner

BIOPHARMACEUTICAL COMPOSITIONS COMPRISING NUCLEIC ACIDS ENCODING IL-5 BINDING PROTEINS

CROSS REFERENCE TO RELATED APPLICATIONS

This application is a divisional of U.S. application Ser. No. 15/987,942, filed May 24, 2018, now U.S. Pat. No. 10,787,509, which claims the benefit of U.S. Provisional Application No. 62/511,441, filed May 26, 2017, which are incorporated herein in their entirety.

SEQUENCE LISTING

The instant application contains a Sequence Listing, which has been submitted electronically in ASCII text file format and is hereby incorporated by reference in its entirety. Said ASCII file, created on Aug. 7, 2020, is named "PU66209TD1_US_SeqList" and is 22,100 bytes in size.

FIELD OF THE DISCLOSURE

The present disclosure relates to compositions, for treating interleukin 5 (IL-5) mediated diseases, and related methods.

BACKGROUND OF THE DISCLOSURE

IL-5 a secreted protein. IL-5 plays a role in a number of different diseases such as asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis. These serious diseases affect hundreds of millions of people world wide.

This means a need exists for compositions suitable for treating IL-5 mediated disease. Such compositions and related methods are provided by the present disclosure.

SUMMARY OF THE DISCLOSURE

One aspect of the disclosure is an antigen binding protein comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10.

Another aspect of the disclosure is an antigen binding protein comprising a heavy chain variable region sequence having the amino acid sequence shown in SEQ ID NO: 3; and a light chain variable region sequence having the amino acid sequence shown in SEQ ID NO: 4.

Another aspect of the disclosure is an antibody comprising a heavy chain and a light chain, wherein a) the heavy chain comprises a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and b) the light chain comprises a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10.

Another aspect of the disclosure is an antibody comprising a heavy chain and a light chain, wherein a) the heavy chain comprises a heavy chain variable region sequence having the amino acid sequence shown in SEQ ID NO: 3; and b) the light chain comprises a light chain variable region sequence having the amino acid sequence shown in SEQ ID NO: 4.

Another aspect of the disclosure is an antibody comprising a heavy chain having the amino acid sequence shown in SEQ ID NO: 1 and a light chain having the amino acid sequence shown in SEQ ID NO: 2.

Another aspect of the disclosure is a peptide chain comprising the amino acid sequence shown in SEQ ID NO: 3.

Another aspect of the disclosure is a peptide chain comprising the amino acid sequence shown in SEQ ID NO: 1.

Another aspect of the disclosure is a composition comprising a nucleic acid encoding the amino acid sequence shown in SEQ ID NO: 3 and a nucleic acid encoding the amino acid sequence shown in SEQ ID NO: 4.

Another aspect of the disclosure is a composition comprising a nucleic acid encoding the amino acid sequence shown in SEQ ID NO: 1 and a nucleic acid encoding the amino acid sequence shown in SEQ ID NO: 2.

Another aspect of the disclosure is a composition comprising a nucleic acid encoding the amino acid sequence shown in SEQ ID NO: 3.

Another aspect of the disclosure is a composition comprising a nucleic acid encoding the amino acid sequence shown in SEQ ID NO: 1.

Another aspect of the disclosure is a composition comprising a nucleic acid having the sequence shown in SEQ ID NO. 15 and a nucleic acid having the sequence shown in SEQ ID NO: 16.

Another aspect of the disclosure is a composition comprising a nucleic acid having the sequence shown in SEQ ID NO: 17 and a nucleic acid having the amino acid sequence shown in SEQ ID NO: 18.

Another aspect of the disclosure is a composition comprising a nucleic acid having the sequence shown in SEQ ID NO: 13 and a nucleic acid having the amino acid sequence shown in SEQ ID NO: 14.

Another aspect of the disclosure is a composition comprising a nucleic acid having the sequence shown in SEQ ID NO: 15.

Another aspect of the disclosure is a composition comprising a nucleic acid having the sequence shown in SEQ ID NO: 17.

Another aspect of the disclosure is a composition comprising a nucleic acid having the sequence shown in SEQ ID NO: 13.

Another aspect of the disclosure is a method for the production of a peptide chain comprising the amino acid sequence shown SEQ ID NO: 3 said method comprising the step of culturing a recombinant host cell comprising a nucleic acid encoding the amino acid sequence shown in SEQ ID NO: 3; and recovering the peptide chain.

Another aspect of the disclosure is a method for the production of an antibody comprising the steps of: a) culturing a recombinant host cell comprising an expression vector comprising a nucleic acid having the sequence shown in SEQ ID NO: 17 and a nucleic acid having the sequence shown in SEQ ID NO: 18; and b) recovering the antibody; whereby the antibody is produced.

Another aspect of the disclosure is a pharmaceutical composition comprising: a) an antigen binding protein comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) a pharmaceutically acceptable carrier.

Another aspect of the disclosure is a pharmaceutical composition comprising: a) an antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) a pharmaceutically acceptable carrier.

Another aspect of the disclosure is a pharmaceutical composition comprising: a) an antibody comprising a heavy chain and a light chain, wherein the heavy chain comprises a heavy chain variable region sequence having the amino acid sequence shown in SEQ ID NO: 3; and the light chain comprises a light chain variable region sequence having the amino acid sequence shown in SEQ ID NO: 4; and b) a pharmaceutically acceptable carrier.

Another aspect of the disclosure is a pharmaceutical composition comprising: a) an antibody comprising a heavy chain having the amino acid sequence shown in SEQ ID NO: 1 and a light chain having the amino acid sequence shown in SEQ ID NO: 2; and b) a pharmaceutically acceptable carrier.

Another aspect of the disclosure is a method of treating mild to moderate asthma in a subject comprising the steps of: a) identifying a subject having a mild asthma to moderate asthma diagnosis; and b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10; whereby the mild to moderate asthma in the subject is treated.

Another aspect of the disclosure is a method of treating mild to moderate asthma in a subject comprising the steps of: a) identifying a subject having a mild asthma to moderate asthma diagnosis; and b) administering to the subject a therapeutically effective amount of an antibody comprising a heavy chain having an amino acid sequence as shown in SEQ ID NO: 1 and a light chain having an amino acid sequence as shown in SEQ ID NO: 1; whereby the mild to moderate asthma in the subject is treated.

Another aspect of the disclosure is a method of treating mild to moderate asthma in a subject comprising the steps of: a) identifying a subject having a mild asthma to moderate asthma diagnosis; and b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier; whereby the mild to moderate asthma in the subject is treated.

Another aspect of the disclosure is a method of treating severe asthma in a subject comprising the steps of: a) identifying a subject having a severe asthma diagnosis; and b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10; whereby the severe asthma in the subject is treated.

Another aspect of the disclosure is a method of treating severe asthma in a subject comprising the steps of: a) identifying a subject having a severe asthma diagnosis; and b) administering to the subject a therapeutically effective amount of an antibody comprising a heavy chain having an amino acid sequence as shown in SEQ ID NO: 1 and a light chain having an amino acid sequence as shown in SEQ ID NO: 1; whereby the severe asthma in the subject is treated.

Another aspect of the disclosure is a method of treating severe asthma in a subject comprising the steps of: a) identifying a subject having a severe asthma diagnosis; and b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier; whereby the severe asthma in the subject is treated.

Another aspect of the disclosure is a method of treating moderate to severe atopic dermatitis in a subject in need thereof comprising the steps of: a) identifying a subject having at least one selected from the group consisting of: i) an atopic dermatitis diagnosis according to the Eichenfield revised criteria of Hanifin and Rajka; ii) a prior diagnosis of atopic dermatitis for greater than or equal to about two years before treatment; iii) a health care professional's global assessment score greater than or equal to about three; iv) atopic dermatitis involvement of greater than or equal to about 10% of body surface area; v) an eczema area and severity index score greater than or equal to 16; vi) an absolute blood eosinophil count of greater than or equal to 150 cells per μL, greater than or equal to 200 cells per μL, greater than or equal to 300 cells per μL, or greater than or equal to 350 cells per μL; and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10; whereby the atopic dermatitis in the subject is treated.

Another aspect of the disclosure is a method of treating moderate to severe atopic dermatitis in a subject in need thereof comprising the steps of: a) identifying a subject having at least one selected from the group consisting of: i) an atopic dermatitis diagnosis according to the Eichenfield revised criteria of Hanifin and Rajka; ii) a prior diagnosis of atopic dermatitis for greater than or equal to about two years before treatment; iii) a health care professional's global assessment score greater than or equal to about three; iv) atopic dermatitis involvement of greater than or equal to about 10% of body surface area; v) an eczema area and severity index score greater than or equal to 16; vi) an absolute blood eosinophil count of greater than or equal to 150 cells per µL; of greater than or equal to 200 cells per µL and greater than or equal to 350 cells per µL; and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and b) administering to the subject a therapeutically effective amount of an antibody comprising a heavy chain having an amino acid sequence as shown in SEQ ID NO: 1 and a light chain having an amino acid sequence as shown in SEQ ID NO: 1; whereby the atopic dermatitis in the subject is treated.

Another aspect of the disclosure is a method of treating moderate to severe atopic dermatitis in a subject comprising the steps of: a) identifying a subject having at least one selected from the group consisting of: i) an atopic dermatitis diagnosis according to the Eichenfield revised criteria of Hanifin and Rajka; ii) a prior diagnosis of atopic dermatitis for greater than or equal to about two years before treatment; iii) a health care professional's global assessment score greater than or equal to about three; iv) atopic dermatitis involvement of greater than or equal to about 10% of body surface area; v) an eczema area and severity index score greater than or equal to 16; vi) an absolute blood eosinophil count of of greater than or equal to 150 cells per µL of greater than or equal to 200 cells per µL and greater than or equal to 350 cells per µL; and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier; whereby the atopic dermatitis in the subject is treated.

Another aspect of the disclosure is a method of decreasing an absolute blood eosinophil count in a subject comprising the steps of: a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10; whereby the absolute blood eosinophil count in a subject is decreased.

Another aspect of the disclosure is a method of decreasing an absolute blood eosinophil count in a subject comprising the steps of: a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering to the subject a therapeutically effective amount of an antibody comprising a heavy chain having an amino acid sequence as shown in SEQ ID NO: 1 and a light chain having an amino acid sequence as shown in SEQ ID NO: 1; whereby the atopic dermatitis in the subject is treated.

Another aspect of the disclosure is a method of decreasing an absolute blood eosinophil count in a subject with comprising the steps of: a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier; whereby the absolute blood eosinophil count in a subject is decreased.

DETAILED DESCRIPTION OF THE DISCLOSURE

The present disclosure provides compositions, for treating interleukin 5 (IL-5) mediated diseases, and related subject matter.

The term "asthma" as used herein means an inflammatory disease of the airways characterized by reversible airflow obstruction and bronchospasm. Common symptoms include wheezing, coughing, chest tightness, and shortness of breath. Asthma is a heterogeneous disease, usually characterized by chronic airway inflammation. It is defined by the history of respiratory symptoms such as wheeze, shortness of breath, chest tightness and cough that vary over time and in intensity, together with variable expiratory airflow limitation.

Figure 8:
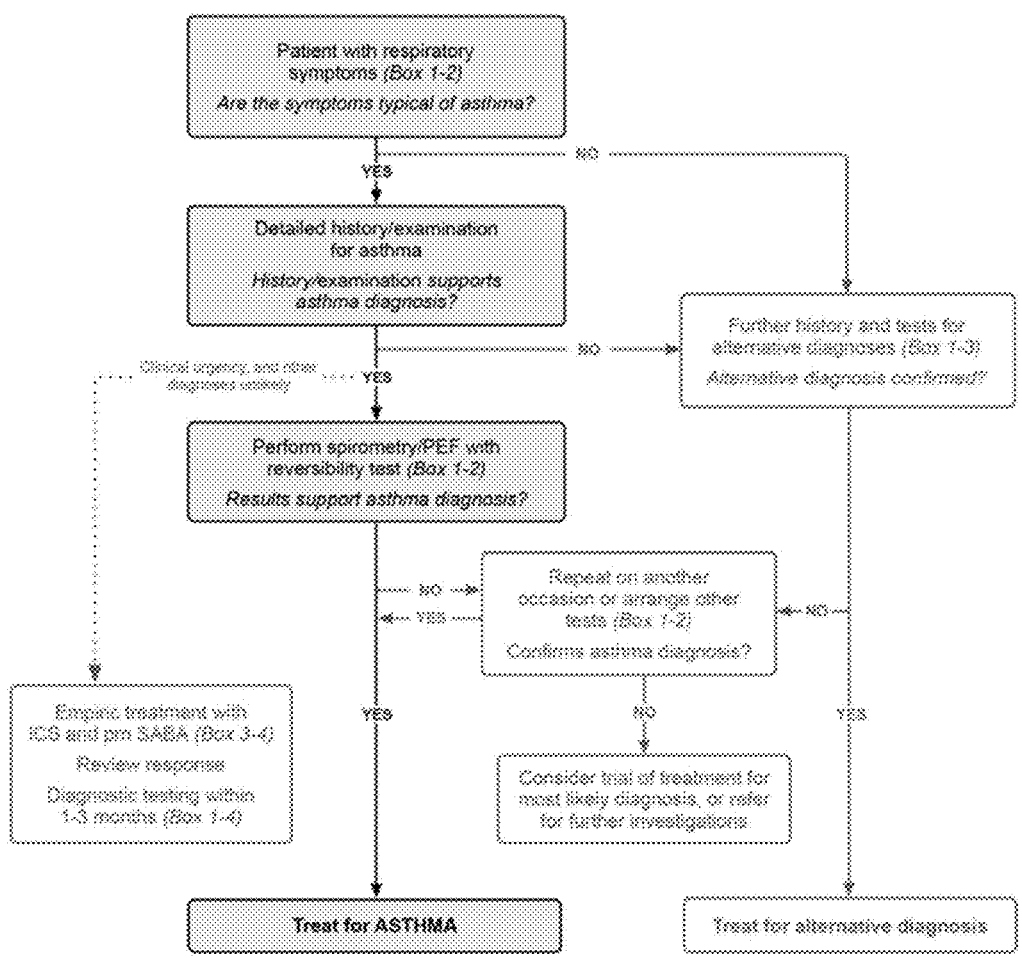
FIG. 8. Box 1-1. Diagnostic flowchart for clinical practice—initial presentation.

In the methods of the disclosure a diagnosis of asthma in a subject may be made according to the guidance provided by the Global Initiative for Asthma (GINA) the Global Strategy for Asthma Management and Prevention (2016 update) document. Those of ordinary skill in the art will be familiar with the GINA diagnostic flow chart for clinical practice (FIG. 8) and diagnostic criteria for asthma in adults, adolescents and children 6-11 years (Table 1) shown below as well as other aspect of the guidance (e.g., for pregnant women etc.). See also Table 2 and Table 3.

TABLE 1

Box 1-2. Diagnostic criteria for asthma in adults, adolescents, and children 6-11 years. Asthma is a heterogeneous disease, usually characterized by chronic airway inflammation. It is defined by the history of respiratory symptoms such as wheeze, shortness of breath, chest tightness and cough that vary over time and in intensity, together with variable expiratory airflow limitation.

| DIAGNOSTIC FEATURE | DIAGNOSTIC FEATURE |
|---|---|
| 1. History of variable respiratory symptoms | |
| Wheeze, shortness of breath, chest tightness and cough Descriptors may vary between cultures and by age, e.g. children may be described as having heavy breathing | Generally more than one type of respiratory symptom (in adults, isolated cough is seldom due to asthma) Symptoms occur variably over time and vary in intensity Symptoms are often worse at night or on waking Symptoms are often triggered by exercise, laughter, allergens, cold air Symptoms often appear or worsen with viral infections |
| 2. Confirmed variable expiratory airflow limitation | |
| Documented excessive variability in lung function* (one or more of the tests below) AND documented airflow limitation* | The greater the variations, or the more occasions excess variation is seen, the more confident the diagnosis At least once during diagnostic process when FEV1 is low, confirm that FEV1/FVC is reduced (normally >0.75-0.80 in adults, >0.90 in children) |
| Positive bronchodilator (BD) reversibility test* (more likely to be positive if BD medication is withheld before test: SABA >4 hours, LABA >15 hours) | Adults: increase in FEV1 of >12% and >200 mL from baseline, 10-15 minutes after 200-400 mcg albuterol or equivalent (greater confidence if increase is >15% and >400 mL). Children: increase in FEV1 of >12% predicted |
| Excessive variability in twice-daily PEF over 2 weeks* | Adults: average daily diurnal PEF variability >10%** Children: average daily diurnal PEF variability >13%** |

TABLE 1-continued

Box 1-2. Diagnostic criteria for asthma in adults, adolescents, and children 6-11 years.
Asthma is a heterogeneous disease, usually characterized by chronic airway inflammation.
It is defined by the history of respiratory symptoms such as wheeze, shortness of breath,
chest tightness and cough that vary over time and in intensity, together with variable
expiratory airflow limitation.

| DIAGNOSTIC FEATURE | DIAGNOSTIC FEATURE |
|---|---|
| Significant increase in lung function after 4 weeks of anti-inflammatory treatment | Adults: increase in FEV1 by >12% and >200 mL (or PEF† by >20%) from baseline after 4 weeks of treatment, outside respiratory infections |
| Positive exercise challenge test* | Adults: fall in FEV1 of >10% and >200 mL from baseline<br>Children: fall in FEV1 of >12% predicted, or PEF >15% |
| Positive bronchial challenge test (usually only performed in adults) | Fall in FEV1 from baseline of >20% with standard doses of methacholine or histamine, or >15% with standardized hyperventilation, hypertonic saline or mannitol challenge |
| Excessive variation in lung function between visits* (less reliable) | Adults: variation in FEV1 of >12% and >200 mL between visits, outside of respiratory infections<br>Children: variation in FEV1 of >12% in FEV1 or >15% in PEF† between visits (may include respiratory infections) |

BD: bronchodilator (short-acting SABA or rapid-acting LABA); FEV1: forced expiratory volume in 1 second; LABA: long-acting beta2-agonist; PEF: peak expiratory flow (highest of three readings); SABA: short-acting beta2-agonist. See Box 1-4 for diagnosis in patients already taking controller treatment.
*These tests can be repeated during symptoms or in the early morning.
**Daily diurnal PEF variability is calculated from twice daily PEF as ([day's highest minus day's lowest]/mean of day's highest and lowest), and averaged over one week.
†For PEF, use the same meter each time, as PEF may vary by up to 20% between different meters. BD reversibility may be lost during severe exacerbations or viral infections. If bronchodilator reversibility is not present at initial presentation, the next step depends on the availability of other tests and the urgency of the need for treatment. In a situation of clinical urgency, asthma treatment may be commenced and diagnostic testing arranged within the next few weeks (Box 1-4), but other conditions that can mimic asthma (Box 1-3) should be considered, and the diagnosis of asthma confirmed as soon as possible.

TABLE 2

Box 1-3. Differential diagnosis of asthma in adults, adolescents and children 6-11 years.

| Age | Condition | Symptoms |
|---|---|---|
| 6-11 years | Chronic upper airway cough syndrome | Sneezing, itching, blocked nose, throat-clearing |
| | Inhaled foreign body | Sudden onset of symptoms, unilateral wheeze |
| | Bronchiectasis | Recurrent infections, productive cough |
| | Primary ciliary dyskinesia | Recurrent infections, productive cough, sinusitis |
| | Congenital heart disease | Cardiac murmurs |
| | Bronchopulmonary dysplasia | Pre-term delivery, symptoms since birth |
| | Cystic fibrosis | Excessive cough and mucus production, gastrointestinal symptoms |
| 12-39 years | Chronic upper airway cough syndrome | Sneezing, itching, blocked nose, throat-clearing |
| | Vocal cord dysfunction | Dyspnea, inspiratory wheezing (stridor) |
| | Hyperventilation, dysfunctional breathing | Dizziness, paresthesia, sighing |
| | Bronchiectasis | Productive cough, recurrent infections |
| | Cystic fibrosis | Excessive cough and mucus production |
| | Congenital heart disease | Cardiac murmurs |
| | Alpha1-antitrypsin deficiency | Shortness of breath, family history of early emphysema |
| | Inhaled foreign body | Sudden onset of symptoms |
| 40+ years | Vocal cord dysfunction | Dyspnea, inspiratory wheezing (stridor) |
| | Hyperventilation, dysfunctional breathing | Dizziness, paresthesia, sighing |
| | COPD* | Cough, sputum, dyspnea on exertion, smoking or noxious exposure |
| | Bronchiectasis | Productive cough, recurrent infections |
| | Cardiac failure | Dyspnea with exertion, nocturnal symptoms |
| | Medication-related cough | Treatment with angiotensin converting enzyme (ACE) inhibitor |
| | Parenchymal lung disease | Dyspnea with exertion, non-productive cough, finger clubbing |
| | Pulmonary embolism | Sudden onset of dyspnea, chest pain |
| | Central airway obstruction | Dyspnea, unresponsive to bronchodilators |

*Any of the above conditions may also contribute to respiratory symptoms in patients with confirmed asthma.

TABLE 3

Box 1-4. Confirming the diagnosis of asthma in a patient already taking controller treatment.

| Current status | Steps to confirm the diagnosis of asthma |
|---|---|
| Variable respiratory symptoms and variable airflow limitation | Diagnosis of asthma is confirmed. Assess the level of asthma control and review controller treatment. |
| Variable respiratory symptoms but no variable airflow limitation | Repeat BD reversibility test again after withholding BD (SABA: 4 hours; LABA: 12+ hours) or during symptoms. If normal, consider alternative diagnoses (Box 1-3). If FEV1 is >70% predicted: consider a bronchial provocation test. If negative, consider stepping down controller treatment and reassess in 2-4 weeks. If FEV1 is <70% predicted: consider stepping up controller treatment for 3 months, then reassess symptoms and lung function. If no response, resume previous treatment and refer patient for diagnosis and investigation |
| Few respiratory symptoms, normal lung function, and no variable airflow limitation | Repeat BD reversibility test again after withholding BD (SABA: 4 hours; LABA: 12+ hours) or during symptoms. If normal, consider alternative diagnoses (Box 1-3). Consider stepping down controller treatment: If symptoms emerge and lung function falls: asthma is confirmed. Step up controller treatment to lowest previous effective dose. If no change in symptoms or lung function at lowest controller step: consider ceasing controller, and monitor patient closely for at least 12 months. |
| Persistent shortness of breath and fixed airflow limitation | Consider stepping up controller treatment for 3 months, then reassess symptoms and lung function. If no response, resume previous treatment and refer patient for diagnosis and investigation. Consider asthma-COPD overlap syndrome. |

BD: bronchodilator;
LABA: long-acting beta2-agonist;
SABA: short-acting beta2-agonist In the methods of the disclosure "asthma" may be "mild asthma," "moderate asthma" or "severe asthma." In the methods of the disclosure asthma severity can be assessed according to the GINA guidance. In particular, asthma severity can assessed retrospectively from the level of treatment required to control symptoms and exacerbations. For example, it can be assessed once the patient has been on controller treatment for several months and, if appropriate, treatment step down has been attempted to find the patient's minimum effective level of treatment. Asthma severity is not a static feature and may change over months or years.

Figure 9:
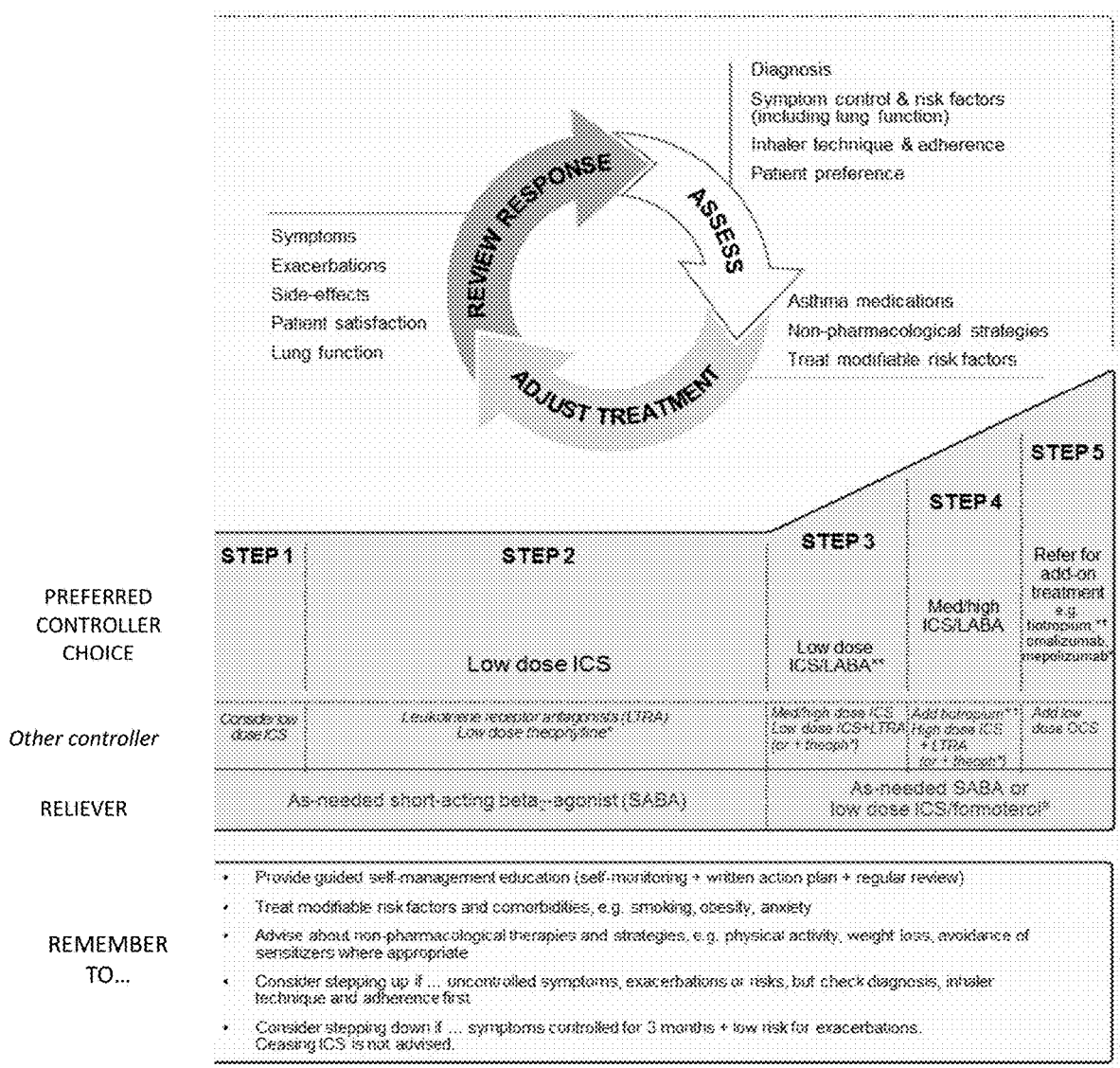
FIG. 9. Box 3-5. Stepwise approach to control symptoms and minimize future risk.

Asthma severity can be assessed when the patient has been on regular controller treatment for several months:
  "Mild asthma" is asthma that is well controlled with Step 1 or Step 2 treatment (see FIG. 9; Box 3-5), i.e., with as-needed reliever medication alone, or with low-intensity controller treatment such as low dose ICS, leukotriene receptor antagonists or chromones.
  "Moderate asthma" is asthma that is well controlled with Step 3 treatment (see FIG. 9; Box 3-5), e.g., low dose ICS/LABA.
  "Severe asthma" is asthma that requires Step 4 or 5 treatment (see FIG. 9; Box 3-5), e.g., high-dose ICS/LABA, to prevent it from becoming 'uncontrolled', or asthma that remains 'uncontrolled' despite this treatment. While many patients with uncontrolled asthma may be difficult to treat due to inadequate or inappropriate treatment, or persistent problems with adherence or comorbidities such as chronic rhinosinusitis or obesity, the European Respiratory Society/American Thoracic Society Task Force on Severe Asthma considered that the definition of "severe asthma" should be reserved for patients with refractory asthma and those in whom response to treatment of comorbidities is incomplete. Table 4 can also be referred to during the assessment of asthma severity.

TABLE 4

| | Daily dose (mcg) | | |
|---|---|---|---|
| Drug | Low | Medium | High |
| Box 3-6. Low, medium and high daily doses of inhaled corticosteroids. | | | |
| Beclometasone dipropionate (CFC)* | 200-500 | >500-1000 | >1000 |
| Beclometasone dipropionate (HFA) | 100-200 | >200-400 | >400 |
| Budesonide (DPI) | 200-400 | >400-800 | >800 |
| Ciclesonide (HFA) | 80-160 | >160-320 | >320 |
| Fluticasone furoate (DPI) | 100 | n.a. | 200 |
| Fluticasone propionate (DPI) | 100-250 | >250-500 | >500 |
| Fluticasone propionate (HFA) | 100-250 | >250-500 | >500 |
| Mometasone furoate | 110-220 | >220-440 | >440 |
| Triamcinolone acetonide | 400-1000 | >1000-2000 | >2000 |

TABLE 4-continued

| Drug | Daily dose (mcg) | | |
|---|---|---|---|
| | Low | Medium | High |
| Children 6-11 years (for children 5 years and younger) | | | |
| Beclometasone dipropionate (CFC)* | 100-200 | >200-400 | >400 |
| Beclometasone dipropionate (HFA) | 50-100 | >100-200 | >200 |
| Budesonide (DPI) | 100-200 | >200-400 | >400 |
| Budesonide (nebules) | 250-500 | >500-1000 | >1000 |
| Ciclesonide | 80 | >80-160 | >160 |
| Fluticasone furoate (DPI) | n.a. | n.a. | n.a. |
| Fluticasone propionate (DPI) | 100-200 | >200-400 | >400 |
| Fluticasone propionate (HFA) | 100-200 | >200-500 | >500 |
| Mometasone furoate | 110 | ≥220-<440 | ≥440 |
| Triamcinolone acetonide | 400-800 | >800-1200 | >1200 |

CFC: chlorofluorocarbon propellant;
DPI: dry powder inhaler;
HFA: hydrofluoroalkane propellant;
n.a. not applicable
*Beclometasone dipropionate CFC is included for comparison with older literature In the methods of the disclosure "asthma" may be "mild eosinophilic asthma," "moderate eosinophilic asthma," or "severe eosinophilic asthma."

"Mild eosinophilic asthma" is mild asthma with an eosinophilic phenotype. For example, subjects with mild eosinophilic asthma may have mild asthma and blood eosinophils greater than or equal to 150 eosinophils per per µL of blood in the past 12 months, greater than or equal to 200 eosinophils per µL of blood in the past 12 months, greater than or equal to 300 eosinophils per µL of blood in the past 12 months or greather than or equal to 350 eosinophils per µL of blood in the past 12 months.

"Moderate eosinophilic asthma" is moderate asthma with an eosinophilic phenotype. For example, subjects with moderate eosinophilic asthma may have moderate asthma and blood eosinophils greater than or equal to 150 eosinophils per per µL of blood in the past 12 months, greater than or equal to 200 eosinophils per µL of blood in the past 12 months, greater than or equal to 300 eosinophils per µL of blood in the past 12 months or greather than or equal to 350 eosinophils per µL of blood in the past 12 months.

"Severe eosinophilic asthma" is severe asthma with an eosinophilic phenotype. For example, subjects with severe eosinophilic asthma may have severe asthma and blood eosinophils greater than or equal to 150 eosinophils per per µL of blood in the past 12 months, greater than or equal to 200 eosinophils per µL of blood in the past 12 months, greater than or equal to 300 eosinophils per µL of blood in the past 12 months (preferred) or greather than or equal to 350 eosinophils per µL of blood in the past 12 months.

Subjects with severe eosinophilic asthma may also meet, one or more of, the criteria described in Table 5.

TABLE 5

A subject has severe eosinophilic asthma if they meet the following criteria:

1) The subject has clinical features of severe refractory asthma similar to those indicated in the American Thoracic Society Workshop on Refractory Asthma (162 Am. J. Respir. Crit. Care Med. 2341 (2000) for ≥12 months.

2) The subject has a well-documented requirement for regular treatment with high dose ICS (inhaled corticosteroids) (i.e., ≥880 pg/day fluticasone propionate or equivalent daily), with or without maintenance OCS (oral corticosteroids), in the past 12 months.

3) The subject has a well-documented requirement for controller medication, e.g., long-acting beta-2-agonist, leukotriene receptor antagonist or theophylline in the past 12 months.

4) The subject has persistent airflow obstruction as indicated by a pre-bronchodilator $FEV_1$ <80% predicted recorded or peak flow diurnal variability of >20% on 3 or more days.

5) The subject has airway inflammation which is likely to be eosinophilic in nature as indicated by one of the following characteristics at present or documented in the previous 12 months:

An elevated peripheral blood eosinophil level of ≥300/µL that is related to asthma or Sputum eosinophils ≥3% or Exhaled nitric oxide ≥50 ppb or Prompt deterioration of asthma control (based on documented clinical history or objective measures) following a ≤25% reduction in regular maintenance dose of inhaled or oral corticosteroid dose in the previous 12 months 8) The subject has a previously confirmed history of two or more asthma exacerbations requiring treatment with oral or systemic corticosteroids in the prior 12 months prior, despite the use of high-dose ICS and additional controller medication. For subjects receiving maintenance OCS with high-dose ICS plus controller, the OCS treatment for exacerbations had to be a two-fold or greater increase in the dose of OCS.

9) The subject has asthma as documented by either:

Airway reversibility ($FEV_1$ ≥12% and 200 mL) at present or documented in the previous 12 months or Airway hyper-responsiveness (provocative concentration causing a 20% fall in $FEV_1$ of methacholine <8 mg/mL or provocative dose causing a 20% fall in $FEV_1$ of histamine <7.8 µmol) documented in the prior 12 months or Airflow variability in clinic $FEV_1$ ≥20% between two examinations documented in the prior 12 months ($FEV_1$ recorded during an exacerbation is not valid) or Airflow variability as indicated by >20% diurnal variability in peak flow observed on 3 or more days.

Importantly, subjects with severe eosinophilic asthma according to these criteria may have less than 150 eosinophils per µL of blood at the initiation of treatment.

28Y042-7F11-1 is a monoclonal antibody comprising the heavy chain amino acid sequence shown in SEQ ID NO: 1 and the light chain amino acid sequence shown in SEQ ID NO: 2. 28Y042-7F11-1 and antigen binding proteins of the disclosure—in particular antibody molecules—comprising the heavy chain CDRs and light chain CDRs of 28Y042-7F11-1, may be used to treat severe eosinophilic asthma according to the methods of the disclosure. For example, 28Y042-7F11-1 or the antigen binding proteins of the disclosure, may be indicated for add-on maintenance treatment of severe eosinophilic asthma, as identified by blood eosinophils greater than or equal to 300 cells/µL in the past 12 months and/or blood eosinophils greater than or equal to 150 cells/µL at initiation of treatment and/or blood eosinophils less than 150 cells/µL at initiation of treatment, in patients. Alternatively, 28Y042-7F11-1, or the antigen binding proteins of the disclosure, may be indicated for add-on maintenance treatment of severe eosinophilic asthma, as identified by blood eosinophils greater than or equal to 300 cells/µL in the past 12 months and/or blood eosinophils greater than or equal to 150 cells/µL at initiation of treatment, in patients. 28Y042-7F11-1 or the antigen binding proteins of the disclosure, may be indicated for add-on maintenance treatment of severe eosinophilic asthma, as identified by blood eosinophils greater than or equal to 300 cells/µL in the past 12 months and/or blood eosinophils less than 150 cells/µL at initiation of treatment, in patients. Such patients may be aged 12 years and older. Treatment with 28Y042-7F11-1 or the antigen binding proteins of the disclosure may reduce exacerbations of asthma in patients (e.g., patients with an exacerbation history). The methods of the disclosure may be used when treatment with 28Y042-7F11-1 or the antigen binding proteins of the disclosure is indicated (i.e., such treatment with 28Y042-7F11-1 may be combined with the methods of the disclosure). Treatment with 28Y042-7F11-1 and the antigen binding proteins of the disclosure can:

a) Produce a reduction in exacerbation frequency. Compared with placebo, treatment with 28Y042-7F11-1 or the antigen binding proteins of the disclosure can reduce the rate of 1) clinically significant exacerbations, 2) exacerbations requiring hospitalization or ED visits, and 3) exacerbations requiring hospitalization. This benefit may potentially lead to reductions in morbidity and fatal events due to asthma.

b) Produce a reduction in daily OCS dose: Treatment with 28Y042-7F11-1 or the antigen binding proteins of the disclosure may allow subjects to reduce their daily dose of concomitant corticosteroid without experiencing loss of asthma control. Subjects treated with 28Y042-7F11-1 or the antigen binding compositions of the disclosure may achieve a median percentage reduction of from baseline in daily oral corticosteroid (OCS) dose versus those treated with placebo. In addition, subjects treated with 28Y042-7F11-1 or the antigen binding compositions of the disclosure may achieve a reduction of OCS dose compared with 32% of subjects treated with placebo.

c) Produce an improvement in lung function: Clinically relevant changes in pre- and post-bronchodilator $FEV_1$ may be demonstrated by treatment with 28Y042-7F11-1 or the antigen binding proteins of the disclosure compared with placebo. Any improvements in lung function are of particular clinical importance in this population of subjects as most are on maximal asthma therapy including high dose ICS (inhaled corticosteroids) and/or OCS plus a controller medication.

d) Produce an improvement in asthma control: Statistically significant and clinically relevant improvements may be observed in ACQ-5 with 28Y042-7F11-1 or the antigen binding proteins of the disclosure compared with placebo, indicating subjects may achieve asthma control with the addition of 28Y042-7F11-1 or the antigen binding proteins of the disclosure to their existing asthma treatment.

e) Produce an improvement in quality of life: Statistically significant and clinically relevant changes in SGRQ scores may be demonstrated with 28Y042-7F11-1 or the antigen binding proteins of the disclosure compared with placebo. Subjects may experience marked improvement in asthma symptoms and ability of perform daily activities.

f) Produce a persistence of efficacy and pharmacodynamic effect: Over a period of 32- and/or 52-week treatment durations, a sustained reduction in asthma exacerbations and blood eosinophils, and improvements in lung function, asthma control, and quality of life with no development of tolerance may be observed.

and g) Produce a reduction in blood eosinophils. Treatment with compositions comprising 28Y042-7F11-1 or the antigen binding proteins of the disclosure may result in rapid reduction of blood eosinophils in a subject.

In the methods of the disclosure "asthma" may be "severe asthma." In the methods of the disclosure "asthma" may also be "mild asthma," "moderate asthma," "severe asthma," "mild eosinophilic asthma," "moderate eosinophilic asthma," or "severe eosinophilic asthma" as discussed above. Treatment with compositions comprising 28Y042-7F11-1 or the antigen binding proteins of the disclosure may be used to treat these conditions according to the methods of the disclosure.

In the methods of the disclosure "asthma" may be "uncontrolled eosinophilic asthma." Subjects with uncontrolled eosinophilic asthma meet the criteria described in Table 6.

TABLE 6

A subject has uncontrolled eosinophilic asthma if they meet the following criteria:

1) The subject has a history of diagnosed asthma for at least the prior 12 months.

2) The subject has been prescribed daily use of medium-dose or high-dose ICS (inhaled corticosteroid) plus LABA (long-acting beta agonists) for at least the prior 12 months.

3) The subject's dose of other asthma controller medications must be stable for at least the prior 30 days.

4) The subject has at least 2 documented asthma exacerbations in the prior 12 months that required use of a systemic corticosteroid burst.

Treatment with compositions comprising 28Y042-7F11-1 or the antigen binding proteins of the disclosure may be used to treat uncontrolled eosinophilic asthma according to the methods of the disclosure.

In the methods of the disclosure "asthma" may be "eosinophilic asthma." Subjects with eosinophilic asthma meet the criteria described in Table 7.

TABLE 7

A subject has eosinophilic asthma if they meet the following criteria:
1) The patient has a previous diagnosis of asthma.
2) The patient has had at least 1 asthma exacerbation requiring oral, intramuscular (im), or intravenous (iv) corticosteroid use for at least 3 days in the prior 12 months.
3) The patient has a current blood eosinophil level of at least 400/μl.
4) The patient has airway reversibility of at least 12% to beta-agonist administration.
5) The patient has an ACQ score of at least 1.5.
6) The patient is taking inhaled fluticasone at a dosage of at least 440 μg, or equivalent, daily. Chronic oral corticosteroid use (no more than 10 mg/day prednisone or equivalent) is allowed. The patient's baseline asthma therapy regimen (including, but not limited to, inhaled corticosteroids, oral corticosteroids up to a maximum dose of 10 mg prednisone daily or equivalent, leukotriene antagonists, 5-lipoxygenase inhibitors, or cromolyn) must be stable for the prior 30 days.

In the methods of the disclosure "asthma" may be "sub-eosinophilic asthma." Subjects with sub-eosinophilic asthma meet the criteria described in Table 8.

TABLE 8

A subject has sub-eosinophilic asthma if they meet the following criteria:
1) The patient has a previous diagnosis of asthma.
2) The patient has had at least 1 asthma exacerbation requiring oral, intramuscular (im), or intravenous (iv) corticosteroid use for at least 3 days in the prior 12 months.
3) The patient has a current blood eosinophil level of less than 400/μl.
4) The patient has airway reversibility of at least 12% to beta-agonist administration.
5) The patient has an ACQ score of at least 1.5.
6) The patient is taking inhaled fluticasone at a dosage of at least 440 μg, or equivalent, daily. Chronic oral corticosteroid use (no more than 10 mg/day prednisone or equivalent) is allowed. The patient's baseline asthma therapy regimen (including, but not limited to, inhaled corticosteroids, oral corticosteroids up to a maximum dose of 10 mg prednisone daily or equivalent, leukotriene antagonists, 5-lipoxygenase inhibitors, or cromolyn) must be stable for the prior 30 days.

Treatment with compositions comprising 28Y042-7F11-1 or the antigen binding proteins of the disclosure may be used to treat eosinophilic asthma and may also be used to treat sub-eosinophilic asthma according to the methods of the disclosure.

The term "bullous pemphigoid" (BP) as used herein means an acute or chronic autoimmune skin disease, involving the formation of blisters, more appropriately known as bullae, at the space between the skin layers epidermis and dermis. BP is the most common autoimmune blistering skin disease. It characteristically affects the elderly (>70 years) with an annual incidence of 5 to 35 per million. The incidence of BP is dramatically increasing with an average of 17% per year. BP often starts with extremely pruritic skin lesions resembling eczema or urticaria before vesicles and blisters arise. In 10-30% of patients, BP also involves the oral mucosa. Disease severity can be determined by means of the autoimmune bullous skin disorder intensity score (ABSIS) that evaluates the involved area as well as the disease activity. The disease is due to an autoimmune response to structural components of junctional adhesion complexes leading to the damage of the dermal-epidermal junction with subepidermal blister formation. Specifically, autoreactive B and T cell responses against the hemidesmosomal antigens BP180 and BP230 have been identified. Serum levels of autoantibodies to BP180 reflect the disease severity and activity. The T cells are memory CD4+ cells producing both Th1 and Th2 cytokines, mostly IL-4, IL-5 and IL-13. IL-5 as well as eotaxin are abundantly found in ister fluids. The production of IL-5 is indeed associated with blood eosinophilia and significant eosinophil infiltration in the skin of BP patients. Eosinophils are thought to be critically implicated in blister formation by releasing toxic granule proteins (ESP, MBP) and proteolytic enzymes.

The term "eosinophilic esophagitis" (EoE) as used herein means an allergic inflammatory condition of the esophagus that involves eosinophils. Symptoms are swallowing difficulty, food impaction, and heartburn. EoE is characterised by a dense infiltrate with white blood cells of the eosinophil type into the epithelial lining of the esophagus. EoE is believed to be an allergic reaction against ingested food, based on the important role eosinophils play in allergic reactions. The EoE diagnostic panel can be used to diagnose EoE. EoE can also be diagnosed if gastroesophageal reflux does not respond to a 6 week trial of twice-a-day high-dose proton-pump inhibitors (PPIs) or if a negative ambulatory pH study ruled out gastroesophageal reflux disease (GERD). Endoscopically, ridges, furrows, or rings may be seen in the oesophageal wall. Sometimes, multiple rings may occur in the esophagus, leading to the term "corrugated esophagus" or "feline esophagus" due to similarity of the rings to the cat esophagus. The presence of white exudates in esophagus is also suggestive of the diagnosis. On biopsy taken at the time of endoscopy, numerous eosinophils can typically be seen in the superficial epithelium. A minimum of 15 eosinophils per high-power field are required to make the diagnosis. Eosinophilic inflammation is not limited to the oesophagus alone, and does extend though the whole gastrointestinal tract. Profoundly degranulated eosinophils may also be present, as may microabcesses and an expansion of the basal layer.

Radiologically, the term "ringed esophagus" has been used for the appearance of eosinophilic esophagitis on barium swallow studies to contrast with the appearance of transient transverse folds sometimes seen with esophageal reflux (termed "feline esophagus").

Treatment with compositions comprising 28Y042-7F11-1 or the antigen binding proteins of the disclosure may be used to treat COPD according to the methods of the disclosure.

Subjects with "chronic obstructive pulmonary disease" (COPD) may meet one or more following criteria: a) a prior COPD diagnosis: subjects with a clinically documented history of COPD for at least 1 year in accordance with the definition by the American Thoracic Society/European Respiratory Society; b) severity of COPD: Subjects may present with the following: a measured pre and post-salbutamol Forced Expiratory Volume in one second/Forced vital capacity ($FEV_1/FVC$) ratio of <0.70 to confirm a diagnosis of COPD; a measured post-salbutamol $FEV_1$>20 percent and <=80 percent of predicted normal values calculated using National Health and Nutrition Examination Survey (NHANES) III reference equations; c) a history of exacerbations: a well documented history (like medical record verification) in the 12 months of: at least two moderate COPD exacerbations. Moderate is defined as the use of systemic corticosteroids (IM, intravenous, or oral) and/or treatment with antibiotics, or at least one severe COPD exacerbation. Severe is defined as having required hospitalization. Note: At least one exacerbation must have occurred while the subject was taking Inhaled corticosteroid (ICS) plus long acting beta2-agonist (LABA) plus long acting muscarinic antagonist (LAMA). Note: Prior use of antibiotics alone does not qualify as a moderate exacerbation unless the use was specifically for the treatment of worsening symptoms of COPD; and d) concomitant COPD therapy: a well documented requirement for optimized standard of care (SoC) background therapy that includes ICS plus 2 additional COPD medications (i.e., triple therapy) for the 12 months prior and meets the following criteria: Immediately prior to visit to the healthcare provider, a minimum of 3 months of use of an inhaled corticosteroid (at a dose>=500 micrograms (mcg)/day fluticasone propionate dose equivalent plus); or LABA and LAMA.

Treatment with compositions comprising 28Y042-7F11-1 or the antigen binding proteins of the disclosure may be used to treat COPD according to the methods of the disclosure.

The term "eosinophilic granulomatosis with polyangiitis" (EGPA) as used herein means an autoimmune condition that causes inflammation of small and medium-sized blood vessels (vasculitis) in persons with a history of airway allergic hypersensitivity (atopy). EGPA may also be referred to as Churg-Strauss Syndrome (CSS) or allergic granulomatosis. EGPA usually manifests in three stages. The early (prodromal) stage is marked by airway inflammation; almost all patients experience asthma and/or allergic rhinitis. The second stage is characterized by abnormally high numbers of eosinophils (hypereosinophilia), which causes tissue damage, most commonly to the lungs and the digestive tract. The third stage consists of vasculitis, which can eventually lead to cell death and can be life-threatening.

Subjects with EGPA may meet one or more following criteria: a) asthma; b) blood eosinophil levels greater than 10% of a differential white blood cell count; c) presence of mononeuropathy or polyneuropathy; d) unfixed pulmonary infiltrates; e) presence of paranasal sinus abnormalities; and e) histological evidence of extravascular eosinophils. For classification purposes, a patient shall be said to have EGPA if at least four of the preceding six criteria are positive.

Treatment with compositions comprising 28Y042-7F11-1 or the antigen binding proteins of the disclosure may be used to treat EGPA according to the methods of the disclosure. The compositions of the disclosure may be administered to an EGPA patient in an amount of 300 mg once every 4 weeks.

The term "hypereosinophilic syndrome" (HES) as used herein means a disease characterized by a persistently elevated eosinophil count ($\geq$1500 eosinophils/mm$^3$) in the blood for at least six months without any recognizable cause, with involvement of either the heart, nervous system, or bone marrow.

Subjects with hypereosinophilic syndrome may meet one or more following criteria: a) a documented history of hypereosinophilic syndrome; b) a blood eosinophil count greater than 1500 cells for 6 months; c) signs and symptoms of organ system involvement; and d) no evidence of parasitic, allergic or other causes of eosinophilia after comprehensive evaluation.

Treatment with compositions comprising 28Y042-7F11-1 or the antigen binding proteins of the disclosure may be used to treat hypereosinophilic syndrome according to the methods of the disclosure.

The term "nasal polyposis" as used herein means a disease characterized by the presence of polyps nasal cavity. Such polyps may be in the upper nasal cavity and/or may originate from within the ostiomeatal complex.

Subjects with nasal polyposis may meet one or more following criteria: a) a documented history of nasal polyposis; or b) nasal polyps apparent on examination (e.g., endoscopic examination).

Treatment with compositions comprising 28Y042-7F11-1 or the antigen binding proteins of the disclosure may be used to treat nasal polyposis according to the methods of the disclosure.

The term "atopic dermatitis" as used herein means an inflammatory skin condition characterized by chronic pruritus, lichenification, xerosis, erythematous papules and plaques.

In the methods of the disclosure "atopic dermatitis" may be "moderate to severe atopic dermatitis." Subjects with moderate to severe atopic dermatitis may meet, one or more of, the criteria described in Table 9.

TABLE 9

A subject has moderate to severe atopic dermatitis if they meet the following criteria (e.g., all, or "one or more"):
1. An atopic dermatitis diagnosis according to the Eichenfield revised criteria of Hanifin and Rajka (Eichenfield et al., 70 J Am Acad Dermatol 338 (2014)). See Table 10.
2. Diagnosis of atopic dermatitis $\geq$2 years prior to beginning treatment.
3. A health care professional's global assessment (HGA; also sometimes called an investigator's global assessment or IGA) score $\geq$3 prior to beginning treatment. See Table 11.
4. Atopic dermatitis involvement of $\geq$10% BSA prior to beginning treatment. See Table 12.

TABLE 9-continued

5. An eczema area and severity index (EASI) score ≥16 prior to beginning treatment. See Table 13.
6. An absolute blood eosinophil count ≥350 cells/μL prior to beginning treatment.
7. Optionally, applied a non-prescription, non-medicated (without an active ingredient) emollient twice-daily for at least 7 days immediately prior to beginning treatment.
8. Prior to beginning treatment having at least one of: a) an inadequate response ≤6 months to a stable regimen of prescription topical medication for atopic dermatitis; b) poor tolerance of prescription topical medications for atopic dermatitis; c) a concern for potential side effects from prescription topical medications for atopic dermatitis, such as skin thinning or increased risk of hypothalamic-pituitary-adrenal [HPA] suppression; and/or d) an inadequate response to optimization of nonpharmacological measures for atopic dermatitis such as moisturizers. An "inadequate response" to a stable regimen of prescription topical medication for atopic dermatitis (such as medium to high potency topical corticosteroids or topical calcineurin inhibitors) is defined as failure to achieve and maintain remission or low disease activity state (equivalent to an HGA score =0 [clear] to 2 [mild]) despite treatment for the recommended duration as per label or for the maximum duration recommended for the subject treatment, whichever is shorter.

Subjects with moderate to severe atopic dermatitis may be children under 18 years of age, adults at least 18 years of age or older, or adults between 18 and 70 years of age inclusive. Subjects may be male or female. It is preferred female subjects to be treated are not pregnant, not lactating and/or not likely to become pregnant.

The diagnosis of atopic dermatitis is based on the Eichenfield revised criteria of Hanifin and Rajka Eichenfield revised criteria of Hanifin and Rajka. See Table 10 and Eichenfield et al., 70 J Am Acad Dermatol 338 (2014).

The health care professional's global assessment (HGA) a clinical tool for assessing the current state/severity of a subject's atopic dermatitis. See Rehal et al, 6 PLos ONE e17520 (2011) and Table 11. It is a static 5-point morphological assessment of overall disease severity as determined by a trained healthcare professional using the clinical characteristics of erythema, infiltration, papulation, oozing, and crusting as guidelines. The HGA is made without reference to previous scores. Each assessment should be made as a visual 'average' of the severity of all affected areas at the time of the assessment.

TABLE 10

Criteria for Atopic Dermatitis Diagnosis

ESSENTIAL FEATURES- Must be present:
    Pruritus
    Eczema (acute, subacute, chronic)
        Typical morphology and age-specific patterns*
        Chronic or relapsing history
    *Patterns include:
        1. Facial, neck, and extensor involvement in infants and children
        2. Current or previous flexural lesions in any age group
        3. Sparing of the groin and axillary regions
IMPORTANT FEATURES- Seen in most cases, adding support to the diagnosis:
    Early age of onset
    Atopy
        Personal and/or family history
        Immunoglobulin E reactivity
    Xerosis
ASSOCIATED FEATURES- These clinical associations help to suggest the diagnosis of atopic dermatitis but are too nonspecific to be used for defining or detecting atopic dermatitis for research and epidemiologic studies:
    Atypical vascular responses (e.g., facial pallor, white dermographism, delayed blanch response)
    Keratosis pilaris/pityriasis alba/hyperlinear palms/ichthyosis
    Ocular/periorbital changes
    Other regional findings (e.g., perioral changes/periauricular lesions)
    Perifollicular accentuation/lichenification/prurigo lesions
EXCLUSIONARY CONDITIONS-It should be noted that a diagnosis of atopic dermatitis depends on excluding conditions, such as:
    Scabies
    Seborrheic dermatitis
    Contact dermatitis (irritant or allergic)
    Ichthyoses
    Cutaneous T-cell lymphoma
    Psoriasis
    Photosensitivity dermatoses
    Immune deficiency diseases
    Erythroderma of other causes

TABLE 11

Healthcare Professional's Global Assessment (HGA)

| Score/Grade | | Description |
|---|---|---|
| 0 | Clear | No erythema or induration/papulation, no oozing/crusting; there may be residual discoloration. |
| 1 | Almost Clear | There may be trace faint pink erythema, with almost no induration/papulation, and no oozing/crusting. |
| 2 | Mild | There may be faint pink erythema, with induration/papulation with barely perceptible elevations, and no oozing/crusting. |
| 3 | Moderate | There may be clearly distinguishable dull red erythema with induration/papulation with clearly perceptible elevations but not prominent; there may be some oozing/crusting. |
| 4 | Severe | There may be deep or bright red erythema with induration/papulation with prominent elevations (deep step off of border), with oozing/crusting. |

The assessment of percentage of body surface area (% BSA) is an estimate of the percentage of total involved skin with atopic dermatitis. See Table 12. The % BSA assessment may be performed by looking at inflamed areas from within each of the 4 body surface regions separately: the head and neck, the upper extremities, the trunk and the lower extremities, and each of these body regions can potentially have up to 100% involvement. The raters (e.g., health care professional) will estimate the percentage of involved skin for each of the regions for a % BSA area score that is then multiplied by the appropriate proportionality multiplier to yield the % BSA regional involved value (for subjects≥8 years of age, 0.1 for head, 0.2 upper extremities, 0.3 for trunk and 0.4 for lower extremities). The regional % BSA involved values are summed to generate the total involved % BSA. The regional % BSA area score will also be utilized as part of the matrix to calculate the EASI score.

TABLE 12

Body Surface Area

% BSA area score may be determined by following the 3 steps described here to calculate total % BSA involvement. Step 1: Estimate %BSA involvement in each body region; Step 2: Multiply % involvement by fraction of total body area; Step 3: Calculate the total involved %BSA. The an example of how % total involved BSA may be calculated is provided below:

| Body Region | % Involvement (0-100% each area) | % Involvement × Proportionality Multiplier | Regional % BSA Involvement |
|---|---|---|---|
| Head and neck | | ___ × 0.1 | |
| Upper extremities | | ___ × 0.2 | |
| Trunk | | ___ × 0.3 | |
| Lower extremities | | ___ × 0.4 | |
| Total involved % BSA (sum of the 4 area values) = | | | ___ |

The EASI scoring system is a standardized clinical tool for the assessment of atopic dermatitis that takes into account the overall extent of the % body surface area (% BSA) involved and the severity scores for each of the clinical signs: erythema, induration/papulation, excoriation, and lichenification. See Hanifin et al., 10 Exp Dermatol 11 (2001); Rullo et al., 36 Allergol et Immunopathol 201 (2008) and Table 13. The % BSA area score from the % BSA assessment is to be used as part of the matrix to calculate the EASI score. Severity scores for each of the clinical signs (erythema, induration/papulation, excoriation, and lichenification) are graded on a 4-point scale (0 to 3) for each of the 4 body regions (head and neck, upper extremities, lower extremities, and trunk). The severity scores for each of the signs are summed for each region and multiplied by the % BSA area score and by the appropriate proportionality multiplier (for subjects>8 years of age, 0.1 for head, 0.2 upper extremities, 0.3 for trunk and 0.4 for lower extremities) to generate a regional EASI score. The regional EASI scores are then summed to yield the final EASI score. The EASI score is a static assessment made without reference to previous scores.

TABLE 13

Eczema Area and Severity Index (EASI)

Once a % BSA involvement for each region is determined, each percentage is translated to an area score based on the following definitions:

0 = No involvement

1 = <10%

2 = 10%-29%

3 = 30%-49%

TABLE 13-continued

Eczema Area and Severity Index (EASI)

4 = 50%-69%
5 = 70%-89%
6 = 90%-100%

Severity of Signs: Grade the severity of each sign on a scale of 0 to 3:
✓ Take an average of the severity across the involved area.
✓ Half-points may be used, e.g., 2.5

0     Absent
1     Mild
2     Moderate
3     Severe

Scoring table:

| Body Region | Erythema (0-3) | Induration/ Papulation (0-3) | Excoriation (0-3) | Lichenification (0-3) | Region score (0-6) | Multiplier | Score per body region |
|---|---|---|---|---|---|---|---|
| Head/neck | ( + | + | + | ) | X | × 0.1 | |
| Trunk | ( + | + | + | ) | X | × 0.3 | |
| Upper extremities | ( + | + | + | ) | X | × 0.2 | |
| Lower extremities | ( + | + | + | ) | X | × 0.4 | |

The final EASI score is the sum of the 4 region scores: (0-72)

Therapeutically effective amounts of 28Y042-7F11-1 or the antigen binding proteins of the disclosure can be used to treat a patient with atopic dermatitis or reduce absolute blood eosinophil counts in such patients. Such atopic dermatitis may be moderate atopic dermatitis or severe atopic dermatitis.

Treatment of atopic dermatitis—such as moderate atopic dermatitis or severe atopic dermatitis—with 28Y042-7F11-1 or the antigen binding proteins of the disclosure, according to the methods of the disclosure can produce at least one result selected from the group consisting of:

a) an HGA score of 0 or 1 and at least a 2-grade improvement in the HGA (e.g., relative to a starting HGA score);
b) a decrease in Eczema Area and Severity Index (EASI) score (e.g., relative to a starting EASI score);
c) a decrease in percent of total body surface area (% BSA) affected (e.g., relative to a starting % BSA); and/or
d) a determination by a health care professional that a subject does not have atopic dermatitis according to the Eichenfield revised criteria of Hanifin and Rajka (Eichenfield et al., 70 J Am Acad Dermatol 338 (2014).

The EASI score after treatment according to the methods of the disclosure may be less than 16 such as for example from about 0 to less than 16. The EASI score after treatment may also be from about 0 to about 15, about 0 to about 14, about 0 to about 13, about 0 to about 12, about 0 to about 11, about 0 to about 10, about 0 to about 9, about 0 to about 8, about 0 to about 7, about 0 to about 6, about 0 to about 5, about 0 to about 4, about 0 to about 3, about 0 to about 2, about 0 to about 1, from about 1 to less than 16, from about 2 to less than 16, from about 3 to less than 16, from about 4 to less than 16, from about 5 to less than 16, from about 6 to less than 16, from about 7 to less than 16, from about 8 to less than 16, from about 9 to less than 16, from about 10 to less than 16, from about 11 to less than 16, from about 12 to less than 16, from about 13 to less than 16, from about 14 to less than 16, from about 15 to less than 16, from about 2 to about 15, from about 3 to about 14, from about 4 to about 13, from about 5 to about 12, from about 6 to about 11, from about 7 to about 10, from about 8 to about 9, from about 0 to about 8, from about 8 to less than 16, from about 0 to about 4, from about 4 to about 8, from about 8 to about 12 and from about 12 to less than 16.

The % BSA after treatment according to the methods of the disclosure may be less than about 10% such as for example from about 0% to less than 10%. The % BSA after treatment may also be from about 1% to less than 10%, from about 2% to less than 10%, from about 3% to less than 10%, from about 4% to less than 10%, from about 5% to less than 10%, from about 6% to less than 10%, from about 7% to less than 10%, from about 8% to less than 10%, from about 9% to less than 10%, from about 0% to about 9%, from about 0% to about 8%, from about 0% to about 7%, from about 0% to about 6%, from about 0% to about 5%, from about 0% to about 4%, from about 0% to about 3%, from about 0% to about 3%, from about 0% to about 2%, from about 0% to about 1%, from about 0% to about 5%, from about 5% to less than 10%, from about 0% to about 2.5%, from about 2.5% to about 5%, from about 5% to about 7.5% and from about 7.5% to less than 10%.

The term "antigen binding protein", as used herein refers to isolated antibodies, antibody fragments (e.g., Fabs etc.) and other antibody derived protein constructs—such as those comprising antibody domains (e.g., domain antibodies etc.)—which are capable of binding to human IL-5 (SEQ ID NO: 11).

The term "antibody" as used herein refers to molecules with an immunoglobulin-like domain (e.g., IgG, IgM, IgA, IgD or IgE) and includes monoclonal, recombinant, polyclonal, monoclonal, recombinant, polyclonal, chimeric, human, and humanized molecules of this type. Monoclonal antibodies may be produced by a eukaryotic cell clone expressing an antibody. Monoclonal antibodies may also be produced by a eukaryotic cell line which can recombinantly express the heavy chain and light chain of the antibody by virtue of having nucleic acid sequences encoding these introduced into the cell. Methods to produce antibodies from different eukaryotic cell lines such as Chinese Hamster Ovary cells, hybridomas or immortalized antibody cells derived from an animal (e.g., human) are well known.

The antibody may be derived from rat, mouse, primate (e.g., cynomolgus, Old World monkey or Great Ape), human or other sources such as nucleic acids generated using molecular biology techniques which encode an antibody molecule.

The antibody may comprise a constant region, which may be of any isotype or subclass. The constant region may be of the IgG isotype, for example, $IgG_1$, $IgG_2$, $IgG_3$, $IgG_4$ or variants thereof. The antigen binding protein constant region may be $IgG_1$.

The antigen binding protein may comprise one or more modifications selected from a mutated constant domain such that the antibody has enhanced effector functions/ADCC and/or complement activation.

An antibody may be capable of binding to a target antigen. Examples, of such target antigens include human IL-5 comprising the amino acid sequence shown in SEQ ID NO: 11.

28Y042-7F11-1 comprising the heavy chain amino acid sequence shown in SEQ ID NO: 1 and the light chain amino acid sequence shown in SEQ ID NO: 2 is an example of an antibody. 28Y042-7F11-1 or the antigen binding proteins of the disclosure bind human IL-5 and antagonizes its activity.

28Y042-7F11-1 is a recombinant humanized monoclonal antibody ($IgG_1$, Kappa) 28Y042-7F11-1 has two light and two heavy chains.

The 28Y042-7F11-1 heavy chain is encoded by the nucleic acid sequence shown in SEQ ID NO: 15. The 28Y042-7F11-1 light chain is encoded by the nucleic acid sequence shown in SEQ ID NO: 16.

The 28Y042-7F11-1 heavy and light chains are covalently linked by a single disulfide bond and the heavy chains are linked to each other by two disulfide bonds resulting in a typical IgG molecule.

28Y042-7F11-1 or the antigen binding proteins of the disclosure can be provided as a lyophilized powder containing the antibody and excipients which can be reconstituted with a pharmaceutically acceptable carrier (e.g., sterile water). This reconstituted pharmaceutical composition can then be administered either subcutaneously or intravenously (e.g., with further dilution). 28Y042-7F11-1 or the antigen binding proteins of the disclosure can also be provided as a liquid formulation containing the antibody, excipients and a pharmaceutically acceptable carrier. This liquid pharmaceutical composition can then be administered either subcutaneously or intravenously (e.g., with further dilution).

The term "antibody variant" as used herein means an antibody that differs from a parent antibody by virtue of at least one amino acid modification (e.g., by having a different amino acid side chain), post-translational modification or other modification in at least one heavy chain, light chain, or combinations of these that results in a structural change (e.g., different amino acid side chain, different post-translational modification or other modification) relative to the parent antibody. 28Y042-7F11-1 is an example of a such a parent antibody. Structural changes can be determined directly by a variety of methods well know in the art such as LC-MS, direct sequencing or indirectly via methods such as isoelectric focusing and the like. Such methods are well known to those of ordinary skill in the art.

The term "IL-5" as used herein means human IL-5 comprising the amino acid sequence shown in SEQ ID NO: 11.

The term "specifically binds", as used herein in relation to antigen binding proteins means that the antigen binding protein binds to a target antigen as well as a discrete domain, or discrete amino acid sequence, within a target antigen with no or insignificant binding to other (for example, unrelated) proteins. This term, however, does not exclude the fact that the antigen binding proteins may also be cross-reactive with closely related molecules (for example, those with a high degree of sequence identity or from another genera or species). The antigen binding proteins described herein may bind to human IL-5 or the human IL-5 receptor with at least 2, 5, 10, 50, 100, or 1000-fold greater affinity than they bind to closely related molecules.

The binding affinity ($K_D$) of the antigen binding protein-target antigen interaction may be 1 mM or less, 100 nM or less, 10 nM or less, 2 nM or less or 1 nM or less. Alternatively, the $K_D$ may be between 5 and 10 nM; or between 1 and 2 nM. The $K_D$ may be between 1 pM and 500 pM; or between 500 pM and 1 nM. The binding affinity of the antigen binding protein is determined by the association constant (Ka) and the dissociation constant (Kd) (KD=Kd/Ka). The binding affinity may be measured by BIACORE™, for example, by capture of the test antibody onto a protein-A coated sensor surface and flowing target antigen over this surface. Alternatively, the binding affinity can be measured by FORTEBIO, for example, with the test antibody receptor captured onto a protein-A coated needle and flowing target antigen over this surface.

The $K_d$ may be $1\times10^{-3}$ $Ms^{-1}$ or less, $1\times10^{-4}$ $Ms^{-1}$ or less, or $1\times10^{-5}$ $Ms^{-1}$ or less. The $K_d$ may be between $1\times10^{-5}$ $Ms^{-1}$ and $1\times10^{-4}$ $Ms^{-1}$; or between $1\times10^{-4}$ $Ms^{-1}$ and $1\times10^{-3}$ $Ms^{-1}$. A slow $K_d$ may result in a slow dissociation of the antigen binding protein-target antigen complex and improved neutralization of the target antigen.

The term "specific antigen binding activity" as used herein means antigen binding activity as measured by Surface Plasmon Resonance (SPR). IL-5 specific binding activity may be determined by SPR using a BIACORE™ instrument, for example performed in the binding mode. It is binding activity divided by total protein (e.g., 28Y042-7F11-1) content in a sample.

The term "FcRn binding activity" as used herein means Neonatal Fc (FcRn) Receptor binding activity as measured by Surface Plasmon Resonance (SPR). FcRn binding may be determined using a BIACORE™ instrument. It is binding activity to the FcRn receptor, divided by the total protein concentration of the sample.

The SPR method for specific antigen binding and FcRn binding uses a reference standard of 28Y042-7F11-1. The 28Y042-7F11-1 reference standard can be used in assays to obtain system suitability and sample comparability data, to ensure methods are performing appropriately. The reference standard can allow the establishment of a calibration curve and concentrations of the samples are interpolated from the curve.

By "isolated", it is intended that the molecule, such as an antigen binding protein or nucleic acid, is removed from the environment in which it may be found in nature. For example, the molecule may be purified away from substances with which it would normally exist in nature. For example, the mass of the molecule in a sample may be 95% of the total mass. The disclosure also provides isolated nucleic acids comprising SEQ ID NO:s 13, 14, 15, 16, 17 and/or 18 and portions thereof as well as compositions of these. Importantly, the nucleic acid of the disclosure are typically provided as composition that can comprise any combination of the nucleic acids of the disclosure, buffer, residual buffer, salts, counter ions, water, alcohols or vector and the like. Alternatively, the composition of the disclosure can comprise just the nucleic acids of the disclosure.

The terms "$V_H$" and "$V_L$" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least one CDR and wherein the at least one CDR is CDRH3. Framework regions follow each of these CDR regions. Acceptable heavy chain variable region and light chain variable region framework 1, framework 2 and framework 3 regions are readily recognized by those of ordinary skill in the art. Acceptable heavy chain constant regions (including hinge regions) and light chain constant regions are readily recognized by those of ordinary skill in the art as well. Acceptable antibody isotypes are similarly readily recognized by those of ordinary skill in the art.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the specification follow the Kabat numbering convention.

It will be apparent to those skilled in the art that there are alternative numbering conventions for amino acid residues in variable domain sequences and full length antibody sequences. There are also alternative numbering conventions for CDR sequences, for example those set out according to the Chothia numbering convention. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 14 below represents one definition using each numbering convention for each CDR or binding unit. The Kabat numbering scheme is used in Table 14 to number the variable domain amino acid sequence. It should be noted that some of the CDR definitions may vary depending on the individual publication used.

TABLE 14

| | Kabat CDR | Chothia CDR | AbM CDR | Contact CDR | Minimum binding unit |
|---|---|---|---|---|---|
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

"Percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query sequence may be described by a nucleic acid sequence identified in one or more claims herein.

Nucleic acid sequences which may be useful, and included, in the compositions and related methods of the disclosure may have between about 85% to about 100%, about 90% to about 100%, about 95% to about 100%, about 91%, about 92%, about 93%, about 94%, about 95%, about 96%, about 97%, about 98%, about 99% and about 100% identity to the nucleic acid sequences identified in the disclosure (e.g., nucleic acids encoding an antibody heavy chain or antibody light chain). In the disclosure, percent identity between the nucleic acid sequences described may include any discrete subrange of the percent identify ranges recited above (e.g., any range of integer values within a particular range or discrete subvalues within a particular range).

"Percent identity" between a query amino acid sequence and a subject amino acid sequence is the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query sequence may be described by an amino acid sequence identified in one or more claims herein.

The amino acid sequences which may be useful, and included, in compositions and related methods of the disclosure may have between about 85% to about 100%, about 90% to about 100%, about 95% to about 100%, about 91%, about 92%, about 93%, about 94%, about 95%, about 96%, about 97%, about 98%, about 99% and about 100% identity to the amino acid sequences identified in the disclosure (e.g., to an antibody heavy chain or antibody light chain). In the disclosure, percent identity between the amino acid sequences described may includes any discrete subrange of the percent identify ranges recited above (e.g., any range of integer values within a particular range or discrete subvalues within a particular range).

The terms "peptide", "polypeptide", "protein" and "peptide chain" each refer to a molecule comprising two or more amino acid residues. A peptide may be monomeric or polymeric.

It is well recognized in the art that certain amino acid substitutions are regarded as being "conservative" Amino acids are divided into groups based on common side-chain properties and substitutions within groups that maintain all or substantially all of the binding affinity of the antigen binding protein are regarded as conservative substitutions. See Table 15. The antigen binding proteins disclosed herein can comprise such "conservative" amino acid substitutions.

TABLE 15

| Side chain | Members |
| --- | --- |
| Hydrophobic | met, ala, val, leu, ile |
| Neutral hydrophilic | cys, ser, thr |
| Acidic | asp, glu |
| Basic | asn, gln, his, lys, arg |
| Residues that influence chain orientation | gly, pro |
| Aromatic | trp, tyr, phe |

The term "pharmaceutical composition" as used herein means a composition suitable for administration to a patient.

The pharmaceutical compositions described herein may comprise purified preparations of an antibody as described herein.

For example, the pharmaceutical preparation may comprise a purified preparation of an antibody as described herein in combination with a pharmaceutically acceptable carrier.

Typically, such pharmaceutical compositions comprise a pharmaceutically acceptable carrier as known and called for by acceptable pharmaceutical practice. Examples of such carriers include sterilized carriers, such as saline, Ringers solution, or dextrose solution, optionally buffered with suitable buffers to a pH within a range of 5 to 8.

Pharmaceutical compositions may be administered by injection or infusion (e.g., intravenous, intraperitoneal, intradermal, subcutaneous, intramuscular, or intraportal). Such compositions are suitably free of visible particulate matter. Pharmaceutical compositions may comprise between 1 mg to 10 g of antigen binding protein, for example, between 5 mg and 1 g of antigen binding protein. Alternatively, the composition may comprise between 5 mg and 500 mg of antigen binding protein, for example, between 5 mg and 50 mg.

Methods for the preparation of such pharmaceutical compositions are well known to those skilled in the art. Pharmaceutical compositions may comprise between 1 mg to 10 g of antigen binding protein in unit dosage form, optionally together with instructions for use. Pharmaceutical compositions may be lyophilized (freeze dried) for reconstitution prior to administration according to methods well known or apparent to those skilled in the art. Where antibodies have an IgG$_1$ isotype, a chelator of copper, such as citrate (e.g., sodium citrate) or EDTA or histidine, may be added to the pharmaceutical composition to reduce the degree of copper-mediated degradation of antibodies of this isotype. Pharmaceutical compositions may also comprise a solubilizer, such as arginine, a surfactant/anti-aggregation agent such as polysorbate 80, and an inert gas such as nitrogen to replace vial headspace oxygen.

The term "therapeutically effective amount" as used herein means an amount of an agent (such as an antibody or a pharmaceutical composition), which provides a therapeutic benefit in the treatment or management of one or more symptoms of a condition to be treated (such as asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis). Examples of such treatment or management of one or more symptoms of asthma—including asthma, mild asthma, moderate asthma, severe asthma, mild eosinophilic asthma, moderate eosinophilic asthma, severe eosinophilic asthma, uncontrolled eosinophilic asthma, eosinophilic asthma and sub-eosinophilic asthma—include 1) a reduction of the frequency of asthma exacerbations; 2) a reduction in the time to first clinically significant exacerbation requiring oral or systemic corticosteroids, hospitalisation, and/or emergency department (ED) visits; 3) a reduction in the frequency of exacerbations requiring hospitalization (including intubation and admittance to an intensive care unit) or ED visits; 4) a reduction in the time to first exacerbation requiring hospitalization or ED visit; 5) a change from baseline in clinic pre-bronchodilator FEV$_1$; 6) a change from baseline in clinic post-bronchodilator FEV$_1$; 7) a change from baseline in an Asthma Control Questionnaire (ACQ) score; 8) improved lung function as assessed by spirometry (e.g., vital capacity (VC), forced vital capacity (FVC), forced expiratory volume (FEV) at timed intervals of 0.5, 1.0 (FEV$_1$), 2.0, and 3.0 seconds, forced expiratory flow 25-75% (FEF 25-75) and maximal voluntary ventilation (MVV) total lung capacity, idal volume, residual volume, expiratory reserve volume, inspiratory reserve volume, inspiratory capacity, inspiratory vital capacity, vital capacity, functional residual capacity, residual volume expressed as percent of total lung capacity, alveolar gas volume, actual volume of the lung including the volume of the conducting airway, forced vital capacity, etc.); and 9) a reduction in asthma exacerbations requiring steroids for control (such as oral steroids or steroids—like prednisone, prednisolone etc.—administered by any route). Such a reduction in asthma exacerbations requiring steroids for control may be an approximately 50% reduction in exacerbations requiring steroids (e.g., oral steroids).

Therapeutically effective amounts and treatment regimes are generally determined empirically and may be dependent on factors, such as the age, weight, and health status of the patient and disease or disorder to be treated. Such factors are within the purview of the attending physician.

The dosage of antigen binding protein administered to a subject is generally between 1 μg/kg to 150 mg/kg, between 0.1 mg/kg and 100 mg/kg, between 0.5 mg/kg and 50 mg/kg, between 1 and 25 mg/kg, between about 0.3 mg/kg and about 3 mg/kg or between 1 and 10 mg/kg of the subject's body weight. For example, the dose may be 10 mg/kg, 30 mg/kg, or 60 mg/kg. The dose may also be from 10 mg/kg to 110 mg/mg 15 mg/kg to 25 mg/kg or 15 mg/kg to 100 mg/kg. The antigen binding protein may be administered, for example, parenterally, subcutaneously, intravenously, or intramuscularly. Doses may also be administered on a per subject basis such as about 20 mg per subject to about 750 mg per subject, about 75 mg per subject to about 750 mg per subject, about 20 mg per subject to about 200 mg per subject. The dose may be any discrete subrange with these dosage ranges. For example, the dose may also be administered subcutaneously on a per subject basis such as about 100 mg per subject (e.g., once every four weeks), or 300 mg per subject (or other doses administered may be subcutaneously with provided approximately the same, or comparable, bioavailability is achieved as with intravenous administration—e.g., three doses of 100 mg per subject to achieve a total dose administered subcutaneously of 300 mg per subject).

Ranges provided herein, of any type, include all values within a particular range described and values about an endpoint for a particular range.

If desired, the effective daily dose of an antibody or antigen binding protein of the disclosure (e.g., as a pharmaceutical composition) may be administered as two, three, four, five, six or more doses administered separately at appropriate intervals throughout the day, optionally, in unit dosage forms.

The administration of a dose may be by slow continuous infusion over a period of from 2 to 24 hours, such as of from 2 to 12 hours, or from 2 to 6 hours. Such an administration may result in reduced side effects.

The administration of a dose may be repeated one or more times as necessary, for example, three times daily, once every day, once every 2 days, once a week, once a every 14 days, once a month, once every 3 months, once every 4 months, once every 6 months, or once every 12 months. The antigen binding proteins may be administered by maintenance therapy, for example once a week for a period of 6 months or more. The antigen binding proteins may be administered by intermittent therapy, for example, for a period of 3 to 6 months and then no dose for 3 to 6 months, followed by administration of antigen binding proteins again for 3 to 6 months, and so on, in a cycle.

For example, the dose may be administered subcutaneously, once every 14 or 28 days, in the form of multiple doses on each day of administration. In one embodiment, the dosage of the composition is 100 mg once every 4 weeks (28 days).

The antigen binding protein may be administered to the subject in such a way as to target therapy to a particular site.

The antigen binding protein in the methods of the disclosure may be used in combination with one or more other therapeutically active agents, such as antibodies or small molecule inhibitors By the term "treating" and grammatical variations thereof as used herein, is meant therapeutic therapy. In reference to a particular condition, treating means: (1) to ameliorate the condition of one or more of the biological manifestations of the condition, (2) to interfere with a) one or more points in the biological cascade that leads to or is responsible for the condition or b) one or more of the biological manifestations of the condition, (3) to alleviate one or more of the symptoms, effects or side effects associated with the condition or treatment thereof, (4) to slow the progression of the condition or one or more of the biological manifestations of the condition or (5) to prevent the onset of one or more of the biological manifistations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

The terms "individual", "subject" and "patient" are used herein interchangeably. The subject is typically a human. The subject may also be a mammal, such as a mouse, rat, or primate (e.g., a marmoset or monkey). The subject can be a non-human animal. The antigen binding proteins, compositions and methods of the disclosure also have veterinary use. The subject to be treated may be a farm animal, for example, a cow or bull, sheep, pig, ox, goat or horse, or may be a domestic animal such as a dog or cat. The animal may be any age, or a mature adult animal.

Treatment can be therapeutic, prophylactic or preventative. The subject will be one who is in need thereof. Those in need of treatment may include individuals already suffering from a particular medical disease, in addition to those who may develop the disease in the future.

Thus, the methods, antigen binding proteins and compositions of the disclosure described herein can be used for prophylactic treatment or preventative treatment if specified. In this case, methods, antigen binding proteins and compositions of the disclosure can be used to prevent or delay the onset of one or more aspects or symptoms of a disease. The subject can be asymptomatic. The subject may have a genetic predisposition to the disease. A prophylactically effective amount of the antigen binding protein is administered to such an individual. A prophylactically effective amount is an amount which prevents or delays the onset of one or more aspects or symptoms of a disease described herein.

The methods, antigen binding proteins and compositions of the disclosure need not affect a complete cure, or eradicate every symptom or manifestation of the disease to constitute a viable therapeutic treatment. As is recognised in the art, drugs employed as therapeutic agents in methods of treatment may reduce the severity of a given disease state, but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

One aspect of the disclosure is an antigen binding protein comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10.

In one embodiment of the antigen binding protein the disclosure the heavy chain variable region further comprises a heavy chain FR4 amino acid sequence as shown in SEQ ID NO: 21.

In one embodiment the antigen binding protein of the disclosure comprises a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

Another aspect of the disclosure is an antigen binding protein comprising a heavy chain variable region sequence having the amino acid sequence shown in SEQ ID NO: 3; and a light chain variable region sequence having the amino acid sequence shown in SEQ ID NO: 4.

Another aspect of the disclosure is an antibody comprising a heavy chain and a light chain, wherein a) the heavy chain comprises a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and b) the light chain comprises a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10.

In one embodiment of the antibody of the disclosure the heavy chain variable region further comprises a heavy chain FR4 amino acid sequence as shown in SEQ ID NO: 21.

In one embodiment of the antibody of the disclosure the heavy chain comprises a heavy chain Fc domain having a tyrosine residue at position 252, a threonine residue at position 254 and a glutamic acid residue at position 256.

Another aspect of the disclosure is an antibody comprising a heavy chain and a light chain, wherein a) the heavy chain comprises a heavy chain variable region sequence having the amino acid sequence shown in SEQ ID NO: 3; and b) the light chain comprises a light chain variable region sequence having the amino acid sequence shown in SEQ ID NO: 4.

In one embodiment of the antibody of the disclosure the heavy chain comprises a heavy chain Fc domain having a tyrosine residue at position 252, a threonine residue at position 254 and a glutamic acid residue at position 256.

Another aspect of the disclosure is an antibody comprising a heavy chain having the amino acid sequence shown in SEQ ID NO: 1 and a light chain having the amino acid sequence shown in SEQ ID NO: 2.

Another aspect of the disclosure is a peptide chain comprising the amino acid sequence shown in SEQ ID NO: 3.

Another aspect of the disclosure is a peptide chain comprising the amino acid sequence shown in SEQ ID NO: 1.

In one embodiment the composition of the disclosure comprises a nucleic acid encoding the heavy chain variable region of the disclosure and a nucleic acid encoding the light chain variable region of the antigen binding protein of the disclosure.

In one embodiment the composition of the disclosure comprises a nucleic acid encoding the heavy chain variable region of the disclosure and a nucleic acid encoding the light chain variable region of the disclosure.

In one embodiment the composition of the disclosure comprises a nucleic acid encoding the heavy chain Fc domain connected to the carboxy terminus of the heavy chain variable region of the disclosure and a nucleic acid encoding the light chain variable region of the disclosure.

Another aspect of the disclosure is a composition comprising a nucleic acid encoding the amino acid sequence shown in SEQ ID NO: 3 and a nucleic acid encoding the amino acid sequence shown in SEQ ID NO: 4.

Another aspect of the disclosure is a composition comprising a nucleic acid encoding the amino acid sequence shown in SEQ ID NO: 1 and a nucleic acid encoding the amino acid sequence shown in SEQ ID NO: 2.

Another aspect of the disclosure is a composition comprising a nucleic acid encoding the amino acid sequence shown in SEQ ID NO: 3.

Another aspect of the disclosure is a composition comprising a nucleic acid encoding the amino acid sequence shown in SEQ ID NO: 1.

Another aspect of the disclosure is a composition comprising a nucleic acid having the sequence shown in SEQ ID NO: 15 and a nucleic acid having the sequence shown in SEQ ID NO: 16.

Another aspect of the disclosure is a composition comprising a nucleic acid having the sequence shown in SEQ ID NO: 17 and a nucleic acid having the amino acid sequence shown in SEQ ID NO: 18.

Another aspect of the disclosure is a composition comprising a nucleic acid having the sequence shown in SEQ ID NO: 13 and a nucleic acid having the amino acid sequence shown in SEQ ID NO: 14.

Another aspect of the disclosure is a composition comprising a nucleic acid having the sequence shown in SEQ ID NO: 15.

Another aspect of the disclosure is a composition comprising a nucleic acid having the sequence shown in SEQ ID NO: 17.

Another aspect of the disclosure is a composition comprising a nucleic acid having the sequence shown in SEQ ID NO: 13.

In one embodiment the composition of the disclosure comprises a nucleic acid encoding the heavy chain variable region of the disclosure.

In one embodiment the composition of disclosure comprises a nucleic acid encoding the heavy chain variable region of the disclosure.

In one embodiment the composition of the disclosure comprises a nucleic acid encoding the heavy chain Fc domain connected to the carboxy terminus of the heavy chain variable region of the disclosure.

In one embodiment the expression vector of the disclosure comprises a composition of the disclosure.

In one embodiment the recombinant host cell of the disclosure comprises an expression vector comprising the composition of the disclosure. In an alternative embodiment the recombinant host cell can comprise a first expression vector encoding a first antigen binding protein peptide chain (e.g., an antibody heavy chain) and a second expression vector encoding a second antigen binding peptide chain of the disclosure (e.g., an antibody light chain).

Another aspect of the disclosure is a method for the production of a peptide chain comprising the amino acid sequence shown SEQ ID NO: 3 said method comprising the step of culturing a recombinant host cell comprising a nucleic acid encoding the amino acid sequence shown in SEQ ID NO: 3; and recovering the peptide chain.

In one embodiment of the method of the disclosure the nucleic acid comprises the sequence shown in SEQ ID NO: 15.

In one embodiment of the method of the disclosure the nucleic acid comprises the sequence shown in SEQ ID NO: 13.

In one embodiment of the method of the disclosure the nucleic acid comprises the sequence shown in SEQ ID NO: 17.

One embodiment of the disclosure is a method for the production of an antigen binding protein comprising the steps of: a) culturing a recombinant host cell comprising an expression vector comprising the composition of the disclosure; and b) recovering the antigen binding protein; whereby the antigen binding protein is produced.

In one embodiment of the disclosure an antigen binding protein produced by the method of disclosure.

One embodiment of the disclosure is a method for the production of an antibody comprising the steps of: a) culturing a recombinant host cell comprising an expression vector comprising a composition of the disclosure; and b) recovering the antibody; whereby the antibody is produced.

One embodiment of the disclosure is an antibody produced by the method of the disclosure.

Another aspect of the disclosure is a method for the production of an antibody comprising the steps of: a) culturing a recombinant host cell comprising an expression vector comprising a nucleic acid having the sequence shown in SEQ ID NO: 17 and a nucleic acid having the sequence shown in SEQ ID NO: 18; and b) recovering the antibody; whereby the antibody is produced.

Another aspect of the disclosure is a pharmaceutical composition comprising: a) an antigen binding protein comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) a pharmaceutically acceptable carrier.

In one embodiment of the pharmaceutical composition of the disclosure the heavy chain variable region further comprises a heavy chain FR4 amino acid sequence as shown in SEQ ID NO: 21.

In one embodiment the pharmaceutical composition of the disclosure comprises a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

In one embodiment of the pharmaceutical composition of the disclosure the antigen binding protein is at a concentration between about 75 mg/ml to about 150 mg/ml.

In one embodiment of the pharmaceutical composition of the disclosure the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

In one embodiment of the pharmaceutical composition of the disclosure the pH is about 6.0 and the antigen binding protein is at a concentration of about 150 mg/ml.

Another aspect of the disclosure is a pharmaceutical composition comprising: a) an antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) a pharmaceutically acceptable carrier. 58. The pharmaceutical composition of claim 57 wherein the antibody is at a concentration between about 75 mg/ml to about 150 mg/ml.

In one embodiment of the pharmaceutical composition of the disclosure the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

In one embodiment of the pharmaceutical composition of the disclosure the pH is about 6.0 and the antibody is at a concentration of about 150 mg/ml.

Another aspect of the disclosure is a pharmaceutical composition comprising: a) an antibody comprising a heavy chain and a light chain, wherein the heavy chain comprises a heavy chain variable region sequence having the amino acid sequence shown in SEQ ID NO: 3; and the light chain comprises a light chain variable region sequence having the amino acid sequence shown in SEQ ID NO: 4; and b) a pharmaceutically acceptable carrier.

Another aspect of the disclosure is a pharmaceutical composition comprising: a) an antibody comprising a heavy chain having the amino acid sequence shown in SEQ ID NO: 1 and a light chain having the amino acid sequence shown in SEQ ID NO: 2; and b) a pharmaceutically acceptable carrier.

One embodiment of the disclosure is a method of treating a disease in a subject comprising the steps of: a) identifying a subject with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of an antigen binding protein according to the disclosure to the subject; whereby the disease in the subject is treated.

In one embodiment of the methods of the disclosure the amount of antigen binding protein is about 2 mg to about 600 mg. For example, the amount of antigen binding protein (e.g., antibody) may be a 2 mg, 10 mg, 30 mg, 100 mg, 300 mg or 600 mg dose.

In one embodiment of the method of the disclosure the antigen binding protein is administered once every 3 months or once every 6 months.

In one embodiment of the method of the disclosure the subject has an absolute blood eosinophil count selected from the group consisting of greater than or equal to 200 cells per µL and greater than or equal to 350 cells per µL.

One embodiment of the disclosure is a method of treating a disease in a subject comprising the steps of: a) identifying a subject with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of an antibody according to the disclosure to the subject; whereby the disease in the subject is treated.

One embodiment of the disclosure is a method of treating a disease in a subject comprising the steps of a) identifying a subject with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering a therapeutically effective amount of a composition according to the disclosure to the subject; whereby the disease in the subject is treated.

Another aspect of the disclosure is a method of treating mild to moderate asthma in a subject comprising the steps of: a) identifying a subject having a mild asthma to moderate asthma diagnosis; and b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10; whereby the mild to moderate asthma in the subject is treated.

One embodiment is a method of the disclosure wherein the heavy chain variable region further comprises a heavy chain FR4 amino acid sequence as shown in SEQ ID NO: 21.

One embodiment is a method of the disclosure wherein the antibody comprises a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

One embodiment is a method of the disclosure wherein the antibody comprises a heavy chain variable region sequence having the amino acid sequence shown in SEQ ID NO: 3; and a light chain variable region sequence having the amino acid sequence shown in SEQ ID NO: 4.

One embodiment is a method of the disclosure wherein the antibody is administered subcutaneously.

Another aspect of the disclosure is a method of treating mild to moderate asthma in a subject comprising the steps of: a) identifying a subject having a mild asthma to moderate asthma diagnosis; and b) administering to the subject a therapeutically effective amount of an antibody comprising a heavy chain having an amino acid sequence as shown in SEQ ID NO: 1 and a light chain having an amino acid sequence as shown in SEQ ID NO: 1; whereby the mild to moderate asthma in the subject is treated.

Another aspect of the disclosure is a method of treating mild to moderate asthma in a subject comprising the steps of: a) identifying a subject having a mild asthma to moderate asthma diagnosis; and b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier; whereby the mild to moderate asthma in the subject is treated.

One embodiment is a method of the disclosure wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

Another aspect of the disclosure is a method of treating severe asthma in a subject comprising the steps of: a) identifying a subject having a severe asthma diagnosis; and b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10; whereby the severe asthma in the subject is treated.

Another aspect of the disclosure is a method of treating severe asthma in a subject comprising the steps of: a) identifying a subject having a severe asthma diagnosis; and b) administering to the subject a therapeutically effective amount of an antibody comprising a heavy chain having an amino acid sequence as shown in SEQ ID NO: 1 and a light chain having an amino acid sequence as shown in SEQ ID NO: 1; whereby the severe asthma in the subject is treated.

Another aspect of the disclosure is a method of treating severe asthma in a subject comprising the steps of: a) identifying a subject having a severe asthma diagnosis; and b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier; whereby the severe asthma in the subject is treated.

Another aspect of the disclosure is a method of treating moderate to severe atopic dermatitis in a subject in need thereof comprising the steps of: a) identifying a subject having at least one selected from the group consisting of: i) an atopic dermatitis diagnosis according to the Eichenfield revised criteria of Hanifin and Rajka; ii) a prior diagnosis of atopic dermatitis for greater than or equal to about two years before treatment; iii) a health care professional's global assessment score greater than or equal to about three; iv) atopic dermatitis involvement of greater than or equal to about 10% of body surface area; v) an eczema area and severity index score greater than or equal to 16; vi) an absolute blood eosinophil count of greater than or equal to 150 cells per µL, greater than or equal to 200 cells per µL, greater than or equal to 300 cells per µL, or greater than or equal to 350 cells per µL; and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10; whereby the atopic dermatitis in the subject is treated.

One embodiment is a method of the disclosure wherein the antibody is administered intravenously.

Another aspect of the disclosure is a method of treating moderate to severe atopic dermatitis in a subject in need thereof comprising the steps of: a) identifying a subject having at least one selected from the group consisting of: i) an atopic dermatitis diagnosis according to the Eichenfield revised criteria of Hanifin and Rajka; ii) a prior diagnosis of atopic dermatitis for greater than or equal to about two years before treatment; iii) a health care professional's global assessment score greater than or equal to about three; iv) atopic dermatitis involvement of greater than or equal to about 10% of body surface area; v) an eczema area and severity index score greater than or equal to 16; vi) an absolute blood eosinophil count of greater than or equal to 150 cells per µL, greater than or equal to 200 cells per µL, greater than or equal to 300 cells per µL, or greater than or equal to 350 cells per µL; and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and b) administering to the subject a therapeutically effective amount of an antibody comprising a heavy chain having an amino acid sequence as shown in SEQ ID NO: 1 and a light chain having an amino acid sequence as shown in SEQ ID NO: 1; whereby the atopic dermatitis in the subject is treated.

Another aspect of the disclosure is a method of treating moderate to severe atopic dermatitis in a subject comprising the steps of: a) identifying a subject having at least one selected from the group consisting of: i) an atopic dermatitis diagnosis according to the Eichenfield revised criteria of Hanifin and Rajka; ii) a prior diagnosis of atopic dermatitis for greater than or equal to about two years before treatment; iii) a health care professional's global assessment score greater than or equal to about three; iv) atopic dermatitis involvement of greater than or equal to about 10% of body surface area; v) an eczema area and severity index score greater than or equal to 16; vi) an absolute blood eosinophil count of greater than or equal to 150 cells per µL, greater than or equal to 200 cells per µL, greater than or equal to 300 cells per µL, or greater than or equal to 350 cells per µL; and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier; whereby the atopic dermatitis in the subject is treated.

Another aspect of the disclosure is a method of decreasing an absolute blood eosinophil count in a subject comprising the steps of: a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10; whereby the absolute blood eosinophil count in a subject is decreased.

One embodiment of the method of the disclosure further comprises the steps of: a) making a first measurement of an absolute blood eosinophil count in the subject; b) making a second measurement of an absolute blood eosinophil count in the subject after administering to the subject a therapeutically effective amount of the antigen binding protein; and c) comparing the first measurement and second measurement.

One embodiment of the method of the disclosure further comprises the steps of: a) making a first measurement of an absolute blood eosinophil count in the subject; b) making a second measurement of an absolute blood eosinophil count in the subject after administering to the subject a therapeutically effective amount of the antigen binding protein; and c) comparing the first measurement and second measurement; and wherein the subject has an absolute blood eosinophil count selected from the group consisting of greater than or equal to 200 cells per µL and greater than or equal to 350 cells per µL.

Another aspect of the disclosure is a method of decreasing an absolute blood eosinophil count in a subject comprising the steps of: a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering to the subject a therapeutically effective amount of an antibody comprising a heavy chain having an amino acid sequence as shown in SEQ ID NO: 1 and a light chain having an amino acid sequence as shown in SEQ ID NO: 1; whereby the atopic dermatitis in the subject is treated.

Another aspect of the disclosure is a method of decreasing an absolute blood eosinophil count in a subject with comprising the steps of: a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier; whereby the absolute blood eosinophil count in a subject is decreased.

One embodiment of the disclosure is a composition according to the disclosure for use in therapy.

One embodiment of the disclosure is a composition according to the disclosure for use in treating asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis.

The compositions of the disclosure may further comprise a buffering agent selected from the group consisting of sodium phosphate dibasic heptahydrate, phosphate, citric acid, citrate, sodium phosphate, potassium phosphate, sodium citrate, and histidine, providing a pH of between 6.8 and 7.2 or a pH of from pH 6.2 to pH 6.6 with a pH value of 6.3 being preferred. The buffer in the compositions of the disclosure may be present in the range from about 10-30 mM, about 10-20 mM, about 20 mM or about 15.5 mM. For example, the buffer in the compositions of the disclosure is present at about 20 mM, or at about 15.5 mM sodium phosphate dibasic heptahydrate.

The compositions of the disclosure may comprise sodium phosphate dibasic heptahydrate and citric acid buffering agents providing a pH of from 6.2 to 6.6 inclusive with a pH value of 6.3 being preferred. The sodium phosphate dibasic heptahydrate buffering agent may be present in the range from about 15-16.4 mM and the citric acid buffering agent may be present in the range from about 3.8-4.9 mM. For example, the compositions of the disclosure may comprise about 15.5 mM sodium phosphate dibasic heptahydrate and about 4.5 mM citric acid monohydrate.

The compositions of the disclosure may further comprise a sugar. The compositions of the disclosure may further comprise sucrose. Sucrose may be present in the compositions of the disclosure in the range from about 5-20%; about 10-15%, about 11-13% or at about 12% weight by volume.

The compositions of the disclosure may further comprise polysorbate 80. Polysorbate 80 may be present in the range from about 0.01-0.1% weight by volume. For example, polysorbate 80 may be present in the compositions of the disclosure at about 0.02% weight by volume, or at about 0.05% weight by volume.

The compositions of the disclosure may further comprise EDTA. EDTA may be present in the range from about 0.01-0.1 mM. For example, EDTA may be present at about 0.05 mM.

In one embodiment, the compositions of the disclosure further comprise 20 mM sodium phosphate dibasic heptahydrate, 12% weight of sucrose to volume and 0.05% weight of polysorbate 80 to volume.

In another embodiment, the compositions of the disclosure further comprise 15.5 mM sodium phosphate dibasic, 3.9 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.2 containing 16.1 mM sodium phosphate dibasic heptahydrate, 3.9 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.2 containing 15.2 mM sodium phosphate dibasic heptahydrate, 4.8 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.4 containing 15.8 mM sodium phosphate dibasic heptahydrate, 4.2 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.6 containing 16.3 mM sodium phosphate dibasic heptahydrate, 3.7 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.3 containing 15.5 mM sodium phosphate dibasic heptahydrate, 4.5 mM citric acid monohydrate, 12% weight of sucrose to volume, 0.02% weight of polysorbate 80 to volume and 0.05 mM EDTA. Importantly, the tangential filtration and ultrafiltration exchange step of Example 1 below may be adjusted to produce the compositions of the disclosure, such as a composition of the disclosure comprising 15.5 mM sodium phosphate dibasic heptahydrate, 4.5 mM citric acid monohydrate, 12% weight to volume sucrose, 0.02% weight to volume polysorbate 80, 0.05 mM EDTA at a pH of 6.3—or other such liquid formulations.

The compositions of the disclosure may comprise a purified preparation of a monoclonal antibody and a buffering agent, wherein the composition is at a pH from 6.8 to 7.2, wherein the buffering agent is histidine, phosphate, citric acid, citrate or a salt thereof.

In the compositions of the disclosure the buffering agent may be at least one selected from the group consisting of sodium phosphate dibasic heptahydrate, phosphate, citric acid and citrate.

In the compositions of the disclosure the buffering agent may be sodium phosphate, potassium phosphate, or sodium citrate.

The compositions of the disclosure may comprise a sugar, a carbohydrate and/or a salt.

The compositions of the disclosure may also comprise sucrose or trehalose.

The compositions of the disclosure may also comprise a purified preparation of a monoclonal antibody and a buffering agent, wherein the composition is at a pH from 6.8 to 7.2, wherein the buffering agent is phosphate or a salt thereof.

The composition of the disclosure may also comprise one selected from a first formulation of 20 mM sodium phosphate dibasic heptahydrate, 12% weight of sucrose to volume and 0.05% weight of polysorbate 80 to volume; and a second formulation of 15.5 mM sodium phosphate dibasic heptahydrate, 3.9 mM citric acid monohydrate, 12% weight of sucrose to volume, 0.02% weight of polysorbate 80 to volume and 0.05 mM EDTA; and a third formulation of 26 mM sodium phosphate dibasic heptahydrate, 15% weight of sucrose to volume and 0.065% weight of polysorbate 80 to volume. The composition may be at a pH between about 6.8 to about 7.2, about 6.1 to about 6.5 or about 6 to about 6.6.

The compositions described herein may be produced by any number of conventional techniques. For example, the compositions may be expressed in and purified from recombinant expression systems. In one embodiment, the composition is produced by a method of culturing a host cell under conditions suitable for expression of a polypeptide comprising SEQ ID NO: 1 and SEQ ID NO:2, wherein the composition is expressed, and optionally purified, and optionally formulated within a pharmaceutical composition.

A number of different expression systems and purification regimes can be used to produce the compositions. Generally, host cells are transformed with a recombinant expression vector encoding the antibody. A wide range of host cells can be employed, including Eukaryotic cell lines of mammalian origin (e.g., CHO, Perc6, HEK293, HeLa, NS0). Suitable host cells include mammalian cells such as CHO (e.g., CHOK1 and CHO-DG44).

The host cell may be an isolated host cell. The host cell is usually not part of a multicellular organism (e.g., plant or animal). The host cell may be a non-human host cell.

Appropriate cloning and expression vectors for use with eukaryotic or mammalian cellular hosts and methods of cloning are known in the art.

The cells may be cultured under conditions that promote expression of the antibody. For example, a production bioreactor is used to culture the cells. The production bioreactor volume may be: (i) about 20,000 litres, about 10,000 litres; about 5,000 litres; about 2,000 litres; about 1,000 litres; or about 500 litres; or (ii) between 500 and 20,000 litres; between 500 and 10,000 litres; between 500 and 5,000 litres; between 1,000 and 10,000 litres, or between 2,000 and 10,000 litres. For example, the cells may be cultured in a production bioreactor at a pH of about 6.75 to pH 7.00. Alternatively, the cells may be cultured in a production bioreactor for about 12 to about 18 days. Alternatively, the cells may be cultured in a production bioreactor at a pH of about 6.75 to pH 7.00, for about 12 to about 18 days. This culture step may help to control the level of deamidated antibody variants, for example, to reduce the level of deamidated antibody variants.

The composition may be recovered and purified by conventional protein purification procedures. For example, the composition may be harvested directly from the culture medium. Harvest of the cell culture medium may be via clarification, for example by centrifugation and/or depth filtration. Recovery of the composition is followed by purification to ensure adequate purity.

One or more chromatography steps may be used in purification, for example one or more chromatography resins; and/or one or more filtration steps. For example affinity chromatography using resins, such as protein A, G, or L may be used to purify the composition. Alternatively, or in addition to, an ion-exchange resin such as a cation-exchange may be used to purify the composition. Alternatively, or in addition to, a hydrophobic interaction chromatographic resin may be used to purify the composition. Alternatively the purification steps comprise: an affinity chromatography resin step, followed by a cation-exchange resin step, followed by a hydrophobic interaction chromatographic resin step.

For example, the harvest is placed in contact with a protein A resin. The solution comprising the composition may be eluted from the protein A resin and treated at pH 3.3 to 3.7 for 15 to 240 minutes. This protein A resin step may help to control the level of aggregated antibody variants, for example, to reduce the level of aggregated antibody variants.

The solution comprising the composition may then be further clarified by depth filtration and/or dual layer filtration.

Alternatively, or in addition to, an anion exchange resin may be used. The solution comprising the composition may be placed in contact with an anion exchange resin (for example Q-SEPHAROSE™ Fast Flow anion exchange chromatography) at a load pH of 8.3 to 8.7. The solution comprising the composition may be eluted from the anion exchange resin and held for 96 hours or less. This anion exchange resin step may help to control the level of deamidated antibody variants, for example, to reduce the level of deamidated antibody variants.

Optionally, guanidine and/or ammonium sulphate may be added to the solution comprising the composition, and held for 15 to 240 minutes.

Alternatively, or in addition to, a hydrophobic interaction chromatographic resin may be used. The solution comprising the composition may be placed in contact with a hydrophobic interaction chromatographic resin (e.g., phenyl SEPHAROSE™ fast flow chromatography) at a load ratio of 12 to 27 g protein/L resin. For example, the solution comprising the composition may be eluted using an elution gradient volume (bed volumes; BV) of about 9 to about 11. An elution peak cut stop (% of maximum peak height) of about 17 to about 23 may be used during elution from the hydrophobic interaction chromatographic resin. This hydrophobic interaction chromatographic resin step may help to control the level of aggregated antibody variants, for example, to reduce the level of aggregated antibody variants.

The solution comprising the composition may then be filtered to remove virus. The solution comprising the composition may then be formulated at an antibody concentration of about 76 g protein/L to about 82 g protein/L, or to about 100 g protein/L. The solution comprising the composition may be filled into containers and frozen. Aliquots of the solution comprising the composition may be lyophilized Lyophilizate may be reconstituted by the addition of water to produce a composition comprising 75 mg/L of protein, the monoclonal anti-IL-5 antibody and 20 mM sodium phosphate dibasic heptahydrate, 12% weight of sucrose to volume and 0.05% weight of polysorbate 80 to volume at a pH of from about 6.8 to about 7.2.

In summary, the disclosure includes:
1. An antigen binding protein comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10.
2. The antigen binding protein of 1 wherein the heavy chain variable region further comprises a heavy chain FR4 amino acid sequence as shown in SEQ ID NO: 21.
3. The antigen binding protein of 2 comprising a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.
4. An antigen binding protein comprising a heavy chain variable region sequence having the amino acid sequence shown in SEQ ID NO: 3; and a light chain variable region sequence having the amino acid sequence shown in SEQ ID NO: 4.
5. The antigen binding protein of 4 comprising a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.
6. An antibody comprising a heavy chain and a light chain, wherein
   a) the heavy chain comprises a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and b) the light chain comprises a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10.

7. The antibody of 6 wherein the heavy chain variable region further comprises a heavy chain FR4 amino acid sequence as shown in SEQ ID NO: 21.

8. The antibody of 7 wherein the heavy chain comprises a heavy chain Fc domain having a tyrosine residue at position 252, a threonine residue at position 254 and a glutamic acid residue at position 256.

9. An antibody comprising a heavy chain and a light chain, wherein
a) the heavy chain comprises a heavy chain variable region sequence having the amino acid sequence shown in SEQ ID NO: 3; and
b) the light chain comprises a light chain variable region sequence having the amino acid sequence shown in SEQ ID NO: 4.

10. The antibody of 9 wherein the heavy chain comprises a heavy chain Fc domain having a tyrosine residue at position 252, a threonine residue at position 254 and a glutamic acid residue at position 256.

11. An antibody comprising a heavy chain having the amino acid sequence shown in SEQ ID NO: 1 and a light chain having the amino acid sequence shown in SEQ ID NO: 2.

12. A peptide chain comprising the amino acid sequence shown in SEQ ID NO: 3.

13. A peptide chain comprising the amino acid sequence shown in SEQ ID NO: 1.

14. A composition comprising a nucleic acid encoding the heavy chain variable region of 1 and a nucleic acid encoding the light chain variable region of the antigen binding protein of 1.

15. A composition comprising a nucleic acid encoding the heavy chain variable region of 2 and a nucleic acid encoding the light chain variable region of 2.

16. A composition comprising a nucleic acid encoding the heavy chain Fc domain connected to the carboxy terminus of the heavy chain variable region of 3 and a nucleic acid encoding the light chain variable region of 3.

17. A composition comprising a nucleic acid encoding the heavy chain variable region of 6 and a nucleic acid encoding the light chain variable region of the antigen binding protein of 6.

18. A composition comprising a nucleic acid encoding the heavy chain variable region of 7 and a nucleic acid encoding the light chain variable region of 7.

19. A composition comprising a nucleic acid encoding the heavy chain Fc domain connected to the carboxy terminus of the heavy chain variable region of 8 and a nucleic acid encoding the light chain variable region of 8.

20. A composition comprising a nucleic acid encoding the amino acid sequence shown in SEQ ID NO: 3 and a nucleic acid encoding the amino acid sequence shown in SEQ ID NO: 4.

21. A composition comprising a nucleic acid encoding the amino acid sequence shown in SEQ ID NO: 1 and a nucleic acid encoding the amino acid sequence shown in SEQ ID NO: 2.

22. A composition comprising a nucleic acid encoding the amino acid sequence shown in SEQ ID NO: 3.

23. A composition comprising a nucleic acid encoding the amino acid sequence shown in SEQ ID NO: 1.

24. A composition comprising a nucleic acid having the sequence shown in SEQ ID NO. 15 and a nucleic acid having the sequence shown in SEQ ID NO: 16.

25. A composition comprising a nucleic acid having the sequence shown in SEQ ID NO: 17 and a nucleic acid having the amino acid sequence shown in SEQ ID NO: 18.

26. A composition comprising a nucleic acid having the sequence shown in SEQ ID NO: 13 and a nucleic acid having the amino acid sequence shown in SEQ ID NO: 14.

27. A composition comprising a nucleic acid having the sequence shown in SEQ ID NO: 15.

28. A composition comprising a nucleic acid having the sequence shown in SEQ ID NO: 17.

29. A composition comprising a nucleic acid having the sequence shown in SEQ ID NO: 13.

30. A composition comprising a nucleic acid encoding the heavy chain variable region of 1.

31. A composition comprising a nucleic acid encoding the heavy chain variable region of 2.

32. A composition comprising a nucleic acid encoding the heavy chain Fc domain connected to the carboxy terminus of the heavy chain variable region as in 3.

33. An expression vector comprising the composition of 14, 15, 16, 17, 18, 19, 20, 21, 22, 23, 24, 25, 26, 27, 28, 29, 30, 31 or 32.

34. A recombinant host cell comprising an expression vector comprising the composition of 14, 15, 16, 17, 18, 19, 20, 21, 22, 23, 24, 25, 26, 27, 28, 29, 30, 31 or 32.

35. A method for the production of a peptide chain comprising the amino acid sequence shown SEQ ID NO: 3 said method comprising the step of culturing a recombinant host cell comprising a nucleic acid encoding the amino acid sequence shown in SEQ ID NO: 3; and recovering the peptide chain.

36. The method of 35 wherein the nucleic acid comprises the sequence shown in SEQ ID NO: 15.

37. The method of 35 wherein the nucleic acid comprises the sequence shown in SEQ ID NO: 13.

38. The method of 35 wherein the nucleic acid comprises the sequence shown in SEQ ID NO: 17.

39. A method for the production of an antigen binding protein comprising the steps of:
a) culturing a recombinant host cell comprising an expression vector comprising the composition of 14, 15 or 16; and
b) recovering the antigen binding protein; whereby the antigen binding protein is produced.

40. An antigen binding protein produced by the method of 39.

41. A method for the production of an antibody comprising the steps of:
a) culturing a recombinant host cell comprising an expression vector comprising the composition of 17, 18 or 19; and
b) recovering the antibody;
whereby the antibody is produced.

42. An antibody produced by the method of 41.

43. A method for the production of an antibody comprising the steps of:
a) culturing a recombinant host cell comprising an expression vector comprising the composition of 20 or 22; and
b) recovering the antibody;
whereby the antibody is produced.

44. An antibody produced by the method of 43.

45. A method for the production of an antibody comprising the steps of:
a) culturing a recombinant host cell comprising an expression vector comprising the composition of 24, 26 or 27; and
b) recovering the antibody;
whereby the antibody is produced.

46. An antibody produced by the method of 45.

47. A method for the production of an antibody comprising the steps of:
a) culturing a recombinant host cell comprising an expression vector comprising a nucleic acid having the sequence shown in SEQ ID NO: 17 and a nucleic acid having the sequence shown in SEQ ID NO: 18; and
b) recovering the antibody;
whereby the antibody is produced.

48. An antibody produced by the method of 47.

49. A pharmaceutical composition comprising:
a) an antigen binding protein comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and
b) a pharmaceutically acceptable carrier.

50. The pharmaceutical composition of 49 wherein the heavy chain variable region further comprises a heavy chain FR4 amino acid sequence as shown in SEQ ID NO: 21.

51. The pharmaceutical composition of 50 comprising a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

52. The pharmaceutical composition of 51 wherein the antigen binding protein is at a concentration between about 75 mg/ml to about 150 mg/ml.

53. The pharmaceutical composition of 49, 50, 51 or 52 wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

54. The pharmaceutical composition of 53 wherein the pH is about 6.0 and the antigen binding protein is at a concentration of about 150 mg/ml.

55. A pharmaceutical composition comprising:
a) an antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and
b) a pharmaceutically acceptable carrier.

56. The pharmaceutical composition of 55 wherein the heavy chain variable region further comprises a heavy chain FR4 amino acid sequence as shown in SEQ ID NO: 21.

57. The pharmaceutical composition of 56 comprising a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

58. The pharmaceutical composition of 57 wherein the antibody is at a concentration between about 75 mg/ml to about 150 mg/ml.

59. The pharmaceutical composition of 55, 56, 57 or 58 wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

60. The pharmaceutical composition of 59 wherein the pH is about 6.0 and the antibody is at a concentration of about 150 mg/ml.

61. A pharmaceutical composition comprising:
a) an antibody comprising a heavy chain and a light chain, wherein the heavy chain comprises a heavy chain variable region sequence having the amino acid sequence shown in SEQ ID NO: 3; and the light chain comprises a light chain variable region sequence having the amino acid sequence shown in SEQ ID NO: 4; and
b) a pharmaceutically acceptable carrier.

62. The pharmaceutical composition of 61 comprising a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

63. The pharmaceutical composition of 62 wherein the antibody is at a concentration between about 75 mg/ml to about 150 mg/ml.

64. The pharmaceutical composition of 61, 62 or 63 wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

65. The pharmaceutical composition of 64 wherein the pH is about 6.0 and the antibody is at a concentration of about 150 mg/ml.

66. A pharmaceutical composition comprising:
a) an antibody comprising a heavy chain having the amino acid sequence shown in SEQ ID NO: 1 and a light chain having the amino acid sequence shown in SEQ ID NO: 2; and
b) a pharmaceutically acceptable carrier.

67. The pharmaceutical composition of 66 wherein the antigen binding protein is at a concentration between about 75 mg/ml to about 150 mg/ml.
68. The pharmaceutical composition of 67 wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.
69. The pharmaceutical composition of 68 wherein the pH is about 6.0 and the antigen binding protein is at a concentration of about 150 mg/ml.
70. A method of treating a disease in a subject comprising the steps of:
    a) identifying a subject with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and
    b) administering a therapeutically effective amount of an antigen binding protein according to 1, 2, 3, 4, 5 or 40 to the subject;
    whereby the disease in the subject is treated.
71. The method of 70 wherein the amount of antigen binding protein is about 2 mg to about 600 mg.
72. The method of 71 wherein the antigen binding protein is administered once every 3 months or once every 6 months.
73. The method of 70, 71 or 72 wherein the subject has an absolute blood eosinophil count selected from the group consisting of greater than or equal to 200 cells per µL and greater than or equal to 350 cells per µL.
74. A method of treating a disease in a subject comprising the steps of
    a) identifying a subject with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and
    b) administering a therapeutically effective amount of an antibody according to 6, 7, 8, 9, 10, 11, 42, 44, 46 and 48 to the subject;
    whereby the disease in the subject is treated.
75. The method of 74 wherein the amount of antibody is about 2 mg to about 600 mg.
76. The method of 75 wherein the antibody is administered once every 3 months or once every 6 months.
77. The method of 74, 75 or 76 wherein the subject has an absolute blood eosinophil count selected from the group consisting of greater than or equal to 200 cells per µL and greater than or equal to 350 cells per µL.
78. A method of treating a disease in a subject comprising the steps of
    a) identifying a subject with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and
    b) administering a therapeutically effective amount of a composition according to 49, 50, 51, 52, 53 or 54 to the subject;
    whereby the disease in the subject is treated.
79. The method of 78 wherein the amount of the composition provides an antigen binding protein dose of about 2 mg to about 600 mg.
80. The method of 79 wherein the composition is administered once every 3 months or once every 6 months.
81. The method of 78, 79 or 80 wherein the subject has an absolute blood eosinophil count selected from the group consisting of greater than or equal to 200 cells per µL and greater than or equal to 350 cells per µL.
82. A method of treating a disease in a subject comprising the steps of
    a) identifying a subject with a disease selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and
    b) administering a therapeutically effective amount of a composition according to 55, 56, 57, 58, 59, 60, 61, 62, 63, 65, 65, 66, 67, 68 or 69 to the subject;
    whereby the disease in the subject is treated.
83. The method of 82 wherein the amount of the composition provides an antigen binding protein dose of about 2 mg to about 600 mg.
84. The method of 83 wherein the antibody is administered once every 3 months or once every 6 months.
85. The method of 82, 83 or 84 wherein the subject has an absolute blood eosinophil count selected from the group consisting of greater than or equal to 200 cells per µL and greater than or equal to 350 cells per µL.
86. A method of treating mild to moderate asthma in a subject comprising the steps of:
    a) identifying a subject having a mild asthma to moderate asthma diagnosis; and
    b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10;

whereby the mild to moderate asthma in the subject is treated.

87. The method of 86 wherein the heavy chain variable region further comprises a heavy chain FR4 amino acid sequence as shown in SEQ ID NO: 21.

88. The method of 87 wherein the antibody comprises a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

89. The method of 88 wherein the antibody comprises a heavy chain variable region sequence having the amino acid sequence shown in SEQ ID NO: 3; and a light chain variable region sequence having the amino acid sequence shown in SEQ ID NO: 4.

90. The method of 89 wherein the antibody dose is about 2 mg to about 600 mg.

91. The method of 90 wherein the antibody is administered once every 3 months or once every 6 months.

92. The method of 90 wherein the antibody is administered subcutaneously.

93. The method of 86, 87, 88, 89, 90, 91 or 92 wherein the subject has an absolute blood eosinophil count selected from the group consisting of greater than or equal to 200 cells per μL and greater than or equal to 350 cells per μL.

94. A method of treating mild to moderate asthma in a subject comprising the steps of:
   a) identifying a subject having a mild asthma to moderate asthma diagnosis; and
   b) administering to the subject a therapeutically effective amount of an antibody comprising a heavy chain having an amino acid sequence as shown in SEQ ID NO: 1 and a light chain having an amino acid sequence as shown in SEQ ID NO: 1;
whereby the mild to moderate asthma in the subject is treated.

95. The method of 94 wherein the antibody dose is about 2 mg to about 600 mg.

96. The method of 95 wherein the antibody is administered once every 3 months or once every 6 months.

97. The method of 96 wherein the antibody is administered subcutaneously.

98. The method of 94, 95, 96 or 97 wherein the subject has an absolute blood eosinophil count selected from the group consisting of greater than or equal to 200 cells per μL and greater than or equal to 350 cells per μL.

99. A method of treating mild to moderate asthma in a subject comprising the steps of:
   a) identifying a subject having a mild asthma to moderate asthma diagnosis; and
   b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier;
whereby the mild to moderate asthma in the subject is treated.

100. The method of 92 wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

101. The method of 100 wherein the antibody dose is about 2 mg to about 600 mg.

102. The method of 101 wherein the pharmaceutical composition is administered once every 3 months or once every 6 months.

103. The method of 102 wherein the pharmaceutical composition is administered subcutaneously.

104. The method of 99, 100, 101, 102 or 103 wherein the subject has an absolute blood eosinophil count selected from the group consisting of greater than or equal to 200 cells per μL and greater than or equal to 350 cells per μL.

105. A method of treating severe asthma in a subject comprising the steps of:
   a) identifying a subject having a severe asthma diagnosis; and
   b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10;
whereby the severe asthma in the subject is treated.

106. The method of 105 wherein the heavy chain variable region further comprises a heavy chain FR4 amino acid sequence as shown in SEQ ID NO: 21.

107. The method of 106 wherein the antibody comprises a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

108. The method of 107 wherein the antibody comprises a heavy chain variable region sequence having the amino acid sequence shown in SEQ ID NO: 3; and a light chain variable region sequence having the amino acid sequence shown in SEQ ID NO: 4.

109. The method of 108 wherein the antibody dose is about 2 mg to about 600 mg.

110. The method of 109 wherein the antibody is administered once every 3 months or once every 6 months.

111. The method of 110 wherein the antibody is administered subcutaneously.

112. The method of 105, 106, 107, 108, 109, 110 or 111 wherein the subject has an absolute blood eosinophil count selected from the group consisting of greater than or equal to 200 cells per μL and greater than or equal to 350 cells per μL.

113. A method of treating severe asthma in a subject comprising the steps of:
   a) identifying a subject having a severe asthma diagnosis; and
   b) administering to the subject a therapeutically effective amount of an antibody comprising a heavy chain having an amino acid sequence as shown in SEQ ID NO: 1 and a light chain having an amino acid sequence as shown in SEQ ID NO: 1;
whereby the severe asthma in the subject is treated.

114. The method of 113 wherein the antibody dose is about 2 mg to about 600 mg.
115. The method of 114 wherein the antibody is administered once every 3 months or once every 6 months.
116. The method of 115 wherein the antibody is administered subcutaneously.
117. The method of 113, 114, 115 or 116 wherein the subject has an absolute blood eosinophil count selected from the group consisting of greater than or equal to 200 cells per µL and greater than or equal to 350 cells per µL.
118. A method of treating severe asthma in a subject comprising the steps of:
   a) identifying a subject having a severe asthma diagnosis; and
   b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier;
whereby the severe asthma in the subject is treated.
119. The method of 118 wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.
120. The method of 119 wherein the antibody dose is about 2 mg to about 600 mg.
121. The method of 120 wherein the pharmaceutical composition is administered once every 3 months or once every 6 months.
122. The method of 121 wherein the pharmaceutical composition is administered subcutaneously.
123. The method of 118, 119, 120, 121 or 122 wherein the subject has an absolute blood eosinophil count selected from the group consisting of greater than or equal to 200 cells per µL and greater than or equal to 350 cells per µL.
124. A method of treating moderate to severe atopic dermatitis in a subject in need thereof comprising the steps of:
   a) identifying a subject having at least one selected from the group consisting of:
      i) an atopic dermatitis diagnosis according to the Eichenfield revised criteria of Hanifin and Rajka;
      ii) a prior diagnosis of atopic dermatitis for greater than or equal to about two years before treatment;
      iii) a health care professional's global assessment score greater than or equal to about three;
      iv) atopic dermatitis involvement of greater than or equal to about 10% of body surface area;
      v) an eczema area and severity index score greater than or equal to 16;
      vi) an absolute blood eosinophil count of greater than or equal to 150 cells per µL of greater than or equal to 200 cells per µL and greater than or equal to 350 cells per µL;
      and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and
   b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10;
whereby the atopic dermatitis in the subject is treated.
125. The method of 124 wherein the heavy chain variable region further comprises a heavy chain FR4 amino acid sequence as shown in SEQ ID NO: 21.
126. The method of 125 wherein the antibody comprises a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.
127. The method of 126 wherein the antibody comprises a heavy chain variable region sequence having the amino acid sequence shown in SEQ ID NO: 3; and a light chain variable region sequence having the amino acid sequence shown in SEQ ID NO: 4.
128. The method of 127 wherein the antibody dose is about 2 mg to about 600 mg.
129. The method of 128 wherein the antibody is administered once every 3 months or once every 6 months.
130. The method of 128 wherein the antibody is administered subcutaneously.
131. The method of 128 wherein the antibody is administered intravenously.
132. A method of treating moderate to severe atopic dermatitis in a subject in need thereof comprising the steps of:
   a) identifying a subject having at least one selected from the group consisting of:
      i) an atopic dermatitis diagnosis according to the Eichenfield revised criteria of Hanifin and Rajka;
      ii) a prior diagnosis of atopic dermatitis for greater than or equal to about two years before treatment;
      iii) a health care professional's global assessment score greater than or equal to about three;
      iv) atopic dermatitis involvement of greater than or equal to about 10% of body surface area;
      v) an eczema area and severity index score greater than or equal to 16;
      vi) an absolute blood eosinophil count of greater than or equal to 150 cells per µL of greater than or equal to 200 cells per µL and greater than or equal to 350 cells per µL;
      and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and b) administering to the subject a therapeutically effective amount of an antibody comprising a heavy chain having an amino acid sequence as shown in SEQ ID NO: 1 and a light chain having an amino acid sequence as shown in SEQ ID NO: 1;
whereby the atopic dermatitis in the subject is treated.

133. The method of 132 wherein the antibody dose is about 2 mg to about 600 mg.

134. The method of 133 wherein the antibody is administered once every 3 months or once every 6 months.

135. The method of 134 wherein the antibody is administered subcutaneously.

136. The method of 132, 133, 134 or 135 wherein the subject has an absolute blood eosinophil count selected from the group consisting of greater than or equal to 200 cells per µL and of greater than or equal to 150 cells per µL of greater than or equal to 200 cells per µL and greater than or equal to 350 cells per µL.

137. A method of treating moderate to severe atopic dermatitis in a subject comprising the steps of:
　a) identifying a subject having at least one selected from the group consisting of:
　　i) an atopic dermatitis diagnosis according to the Eichenfield revised criteria of Hanifin and Rajka;
　　ii) a prior diagnosis of atopic dermatitis for greater than or equal to about two years before treatment;
　　iii) a health care professional's global assessment score greater than or equal to about three;
　　iv) atopic dermatitis involvement of greater than or equal to about 10% of body surface area;
　　v) an eczema area and severity index score greater than or equal to 16;
　　vi) an absolute blood eosinophil count of greater than or equal to 150 cells per µL of greater than or equal to 200 cells per µL and greater than or equal to 350 cells per µL;
　　and vii) at least one condition prior to treatment selected from the group consisting of: 1) an inadequate response, for greater than or equal to six months, to a topical medication for atopic dermatitis; 2) poor tolerance of a topical medication for atopic dermatitis; 3) a side effect from a topical medication for atopic dermatitis; and 4) an inadequate response to a nonpharmacological treatment for atopic dermatitis; and
　b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier;
whereby the atopic dermatitis in the subject is treated.

138. The method of 137 wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

139. The method of 138 wherein the antibody dose is about 2 mg to about 600 mg.

140. The method of 139 wherein the pharmaceutical composition is administered once every 3 months or once every 6 months.

141. The method of 140 wherein the pharmaceutical composition is administered subcutaneously.

142. The method of 137, 138, 139, 140 or 141 wherein the subject has an absolute blood eosinophil count selected from the group consisting of greater than or equal to 200 cells per µL and greater than or equal to 350 cells per µL.

143. A method of decreasing an absolute blood eosinophil count in a subject comprising the steps of:
　a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis and atopic dermatitis; and
　b) administering to the subject a therapeutically effective amount of an antibody comprising a heavy chain variable region having a CDR amino acid sequence as shown in SEQ ID NO: 5, a CDR amino acid sequence as shown in SEQ ID NO: 6, and a CDR amino acid sequence as shown in SEQ ID NO: 7; and a light chain variable region having a CDR amino acid sequence as shown in SEQ ID NO: 8, a CDR amino acid sequence as shown in SEQ ID NO: 9, and a CDR amino acid sequence as shown in SEQ ID NO: 10;
whereby the absolute blood eosinophil count in a subject is decreased.

144. The method of 143 wherein the heavy chain variable region further comprises a heavy chain FR4 amino acid sequence as shown in SEQ ID NO: 21.

145. The method of 144 wherein the antibody comprises a heavy chain Fc domain having a tyrosine residue at position 252, a threonine residue at position 254 and a glutamic acid residue at position 256 and wherein an amino terminus of the heavy chain Fc domain is connected to a carboxy terminus of the heavy chain variable region.

146. The method of 145 wherein the antibody comprises a heavy chain variable region sequence having the amino acid sequence shown in SEQ ID NO: 3; and a light chain variable region sequence having the amino acid sequence shown in SEQ ID NO: 4.

147. The method of 146 wherein the antibody dose is about 2 mg to about 600 mg.

148. The method of 147 wherein the antibody is administered once every 3 months or once every 6 months.

149. The method of 148 wherein the antibody is administered subcutaneously.

150. The method of 142, 144, 145, 146, 147, 148 or 149 wherein the subject has an absolute blood eosinophil count selected from the group consisting of greater than or equal to 200 cells per µL and greater than or equal to 350 cells per µL.

151. The method 142, 144, 145, 146, 147, 148 or 149 further comprising the steps of:
　a) making a first measurement of an absolute blood eosinophil count in the subject;
　b) making a second measurement of an absolute blood eosinophil count in the subject after administering to the subject a therapeutically effective amount of the antigen binding protein; and
　c) comparing the first measurement and second measurement.

152. The method of 142, 144, 145, 146, 147, 148 or 149 further comprising the steps of:
   a) making a first measurement of an absolute blood eosinophil count in the subject;
   b) making a second measurement of an absolute blood eosinophil count in the subject after administering to the subject a therapeutically effective amount of the antigen binding protein; and
   c) comparing the first measurement and second measurement; and wherein the subject has an absolute blood eosinophil count selected from the group consisting of greater than or equal to 200 cells per µL and greater than or equal to 350 cells per µL.

153. A method of decreasing an absolute blood eosinophil count in a subject comprising the steps of:
   a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and
   b) administering to the subject a therapeutically effective amount of an antibody comprising a heavy chain having an amino acid sequence as shown in SEQ ID NO: 1 and a light chain having an amino acid sequence as shown in SEQ ID NO: 1;
whereby the atopic dermatitis in the subject is treated.

154. The method of 153 wherein the antibody dose is about 2 mg to about 600 mg.

155. The method of 154 wherein the antibody is administered once every 3 months or once every 6 months.

156. The method of 155 wherein the antibody is administered subcutaneously.

157. The method of 154, 155, 156 or 157 wherein the subject has an absolute blood eosinophil count selected from the group consisting of greater than or equal to 200 cells per µL and greater than or equal to 350 cells per µL.

158. The method of 154, 155, 156 or 157 wherein the subject has an absolute blood eosinophil count selected from the group consisting of greater than or equal to 200 cells per µL and greater than or equal to 350 cells per µL.

159. The method 154, 155, 156 or 157 further comprising the steps of:
   a) making a first measurement of an absolute blood eosinophil count in the subject;
   b) making a second measurement of an absolute blood eosinophil count in the subject after administering to the subject a therapeutically effective amount of the antigen binding protein; and
   c) comparing the first measurement and second measurement.

160. The method of 154, 155, 156 or 157 further comprising the steps of:
   a) making a first measurement of an absolute blood eosinophil count in the subject;
   b) making a second measurement of an absolute blood eosinophil count in the subject after administering to the subject a therapeutically effective amount of the antigen binding protein; and
   c) comparing the first measurement and second measurement; and wherein the subject has an absolute blood eosinophil count selected from the group consisting of greater than or equal to 200 cells per µL and greater than or equal to 350 cells per µL.

161. A method of decreasing an absolute blood eosinophil count in a subject with comprising the steps of:
   a) identifying a subject having a condition selected from the group consisting of asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis; and
   b) administering to the subject a therapeutically effective amount of a pharmaceutical composition comprising an antibody comprising a heavy chain having an amino acid sequence as shown in SEQ ID NO: 1 and a light chain having an amino acid sequence as shown in SEQ ID NO: 1 and a pharmaceutically effective carrier;
whereby the absolute blood eosinophil count in a subject is decreased.

162. The method of 161 wherein the pharmaceutically effective carrier comprises an aqueous liquid formulation at about pH 5.5 to about pH 6.0 containing about 40 mM histidine, about 180 mM trehalose, about 100 mM arginine, about 8 mM methionine, about 0.02% weight of polysorbate 80 to volume and about 0.05 mM EDTA.

163. The method of 162 wherein the antibody dose is about 2 mg to about 600 mg.

164. The method of 163 wherein the pharmaceutical composition is administered once every 3 months or once every 6 months.

165. The method of 164 wherein the pharmaceutical composition is administered subcutaneously.

166. The method of 162, 163, 164, 165 or 166 wherein the subject has an absolute blood eosinophil count selected from the group consisting of greater than or equal to 200 cells per µL and greater than or equal to 350 cells per µL.

167. The method 162, 163, 164, 165 or 166 further comprising the steps of:
   a) making a first measurement of an absolute blood eosinophil count in the subject;
   b) making a second measurement of an absolute blood eosinophil count in the subject after administering to the subject a therapeutically effective amount of the antigen binding protein; and
   c) comparing the first measurement and second measurement.

168. The method of 162, 163, 164, 165 or 166 further comprising the steps of:
   a) making a first measurement of an absolute blood eosinophil count in the subject;
   b) making a second measurement of an absolute blood eosinophil count in the subject after administering to the subject a therapeutically effective amount of the antigen binding protein; and
   c) comparing the first measurement and second measurement; and wherein the subject has an absolute blood eosinophil count selected from the group consisting of greater than or equal to 200 cells per μL and greater than or equal to 350 cells per μL.

169. A composition according to any one of 1-11, 40, 42, 44, 46, 47 or 49-69 for use in therapy.
170. A composition according to any one of 1-11, 40, 42, 44, 46, 47 or 49-69 for use in treating asthma, mild asthma, moderate asthma, severe asthma, mild eosinophilic asthma, moderate eosinophilic asthma, severe eosinophilic asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid, eosinophilic esophagitis, atopic dermatitis, moderate atopic dermatitis and severe atopic dermatitis.

EXAMPLES

Example 1

Kinetic Analysis of 28Y042-7F11-1

Kinetic analyses were performed to compare 28Y042-7F11-1, mepolizumab, and GSK3559090A (a comparator IgG1 anti-IL-5 mAb molecule based). Results are summarised in Table 16 below. Due to the high affinity of 28Y042-7F11-1, it was not possible to accurately determine the dissociation rate by Biacore 4000 at 25° C.; therefore KINEXA analysis was used to calculate an accurate affinity for 28Y042-7F11-1 binding to human IL-5 at 25° C. The affinity of 28Y042-7F11-1 to human IL-5 at 25° C. by KINEXA solution phase affinity analysis was 10.47 pM (95% confidence range 0.88 pM-31.97 pM). This compared to an affinity of 122.8 pM for mepolizumab binding to human IL-5 (determined by BIACORE 4000 at 25° C.).

The comparator antibody GSK3559090A was analysed by BIACORE 4000 for binding to human IL-5 at 25° C., giving an affinity ($K_D$) value of 16.4 pM. GSK3559090A has a 10 times higher $K_D$ for human IL-5 than mepolizumab, mainly as a result of a 20 times faster association rate ($k_a$) of GSK3559090A compared to mepolizumab.

The affinity of 28Y042-7F11-1 to human and cynomolgus IL-5 at 37° C. was determined using BIACORE T200. The higher temperature increased the dissociation rate ($k_d$) of 28Y042-7F11-1 so that it was within the range of the instrument. The affinity of 28Y042-7F11-1 to human and cynomolgus IL-5 at 37° C. is 39.13 pM and 23.93 pM respectively.

A competition assay carried out on the FORTEBIO OCTET RED384 BLI instrument demonstrated that 28Y042-7F11-1 competes with mepolizumab for binding to human IL-5. Table 16 legend/description: Summary of kinetic $K_D$ data. (N.D. not determined).

TABLE 16

|  | Biacore 4000 25° C. ($K_D$, pM) human IL-5 | Kinexa 25° C. ($K_D$, pM) human IL-5 | Biacore T200 37° C. ($K_D$, pM) human IL-5 | Biacore T200 37° C. ($K_D$, pM) cyno IL-5 |
|---|---|---|---|---|
| Mepolizumab | 122.8 | N.D. | N.D. | N.D. |
| 28Y042-7F11-1 | N.D. | 10.5 | 39.1 | 23.9 |
| GSK3559090A | 16.4 | N.D. | N.D. | N.D. |

Binding to Human Fc Receptors

28Y042-7F11-1 has approximately a 13-fold increase in affinity for human FcRn at pH 6.0 compared to mepolizumab (157 nM and 2082 nM, respectively) and also binds with low affinity at pH 7.4; affinity is 16 μM at pH 7. The KD values determined by BIACORE T200 at 37° C. are shown in Table 17. Table 17 legend/description: Comparison of binding affinity of 28Y042-7F11-1 and mepolizumab for human FcRn at pH 6.0 and pH 7.4.

TABLE 17

|  | Affinity (nM) | |
|---|---|---|
|  | pH 6.0 | pH 7.4 |
| mepolizumab | 2082 | not detected |
| 28Y042-7F11-1 | 157 | 16160 |

Analysis of the binding of 28Y042-7F11-1 to human Fc gamma receptors (FcγR) by PROTEON XPR36 demonstrated comparability with the YTE containing control antibody. The binding affinities to FcγR of these YTE-containing mAbs were approximately 1.5-fold lower than that of the human IgG1 wild type control. 28Y042-7F11-1 also had a lower affinity than the human IgG1 wild type control for complement component C1q (750 nM and 465 nM respectively).

In a separate experiment, 28Y042-7F11-1 displayed approximately a 3 fold increase in affinity for human neonatal receptor at pH 6.0 compared to the human IgG1 wild type control (130 nM and 359 nM respectively) and also binds with low affinity at pH 7.4 (2650 nM) whilst the wild type control has no binding to FcRn at this pH (Table 18). This is comparable to the YTE control used in the experiment. Table 18 legend/description: Binding of 28Y042-7F11-1 to recombinant human neonatal receptor (FcRn) using the PROTEON. The wildtype isotype control and Fc disabled isotype control are derived from a non-functional (for CDR binding) antibody, originally raised against F9 coagulation factor IX. The Fc disabled isotype control contains two point mutations in the Fc region (L235 and G237, both mutated to Alanine) that reduces the interaction to Fc gamma receptors.

TABLE 18

|  | $K_D$ (nM) | |
|---|---|---|
| Antibodies | Human FcRn pH 6.0 | Human FcRn pH 7.4 |
| 28Y042-7F11-1 | 130.0 | 2650.0 |
| GSK2800528 | 94.3 | 1190.0 |
| IgG$_1$ wildtype isotype control | 359.0 | NB |
| IgG$_1$ Fc disabled isotype control | 314.0 | NB |

TF-1 Functional Cell Assay

The ability of 28Y042-7F11-1 to inhibit, in a dose dependent manner, human IL-5 mediated proliferation of TF-1 cells was assessed. TF-1 cells are an erythroleukemic cell line that has been engineered to proliferate in response to human and cynomolgus IL-5 stimulation.

Figure 1:
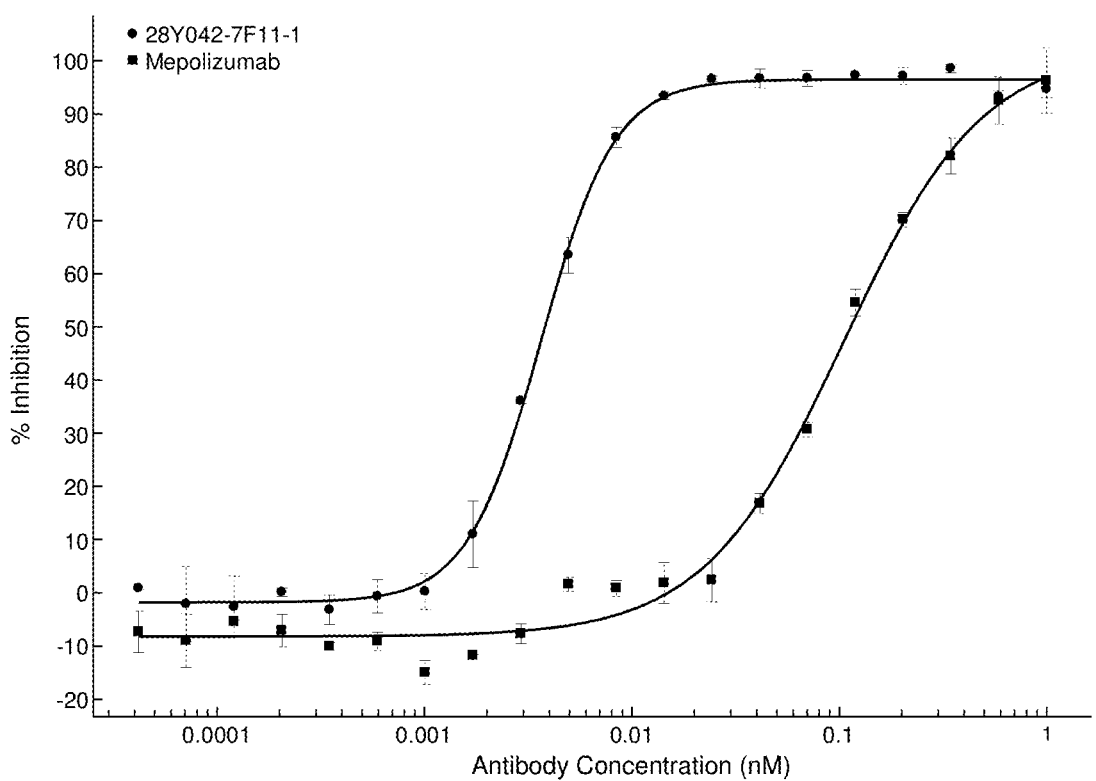
FIG. 1. 28Y042-7F11-1 and mepolizumab both caused a dose dependent inhibition of human IL-5 induced TF-1 cell proliferation ($IC_{50}$ of 4 pM and 105 pM respectively) when tested at a 1 nM-0.042 pM concentration range.

Analysis of the effect of 28Y042-7F11-1 in the TF-1 cell proliferation assay showed that it is a potent inhibitor of the IL-5 mediated proliferation of TF-1 cells. 28Y042-7F11-1 and mepolizumab both caused a dose dependent inhibition of human IL-5 induced TF-1 cell proliferation when tested at a 1 nM-0.042 pM concentration range (IC$_{50}$ of 4 pM and 105 pM respectively, FIG. 1). This demonstrates an approximate 30 fold improvement in cell assay potency of 28Y042-7F11-1 compared to mepolizumab.

28Y042-7F11-1 and mepolizumab both caused a dose dependent inhibition of human IL-5 induced TF-1 cell proliferation when tested at a 1 nM-0.042 pM concentration range ($IC_{50}$ of 0.004 nM and 0.105 nM respectively).

Further analysis of 28Y042-7F11-1 was performed following exposure of the molecule to thermal stress by incubating for 1 week at 40° C. in either acetate or phosphate buffer. In these conditions, the $IC_{50}$ value for 28Y042-7F11-1 in the TF-1 cell assay was in the range of 4 pM-5 pM, showing similar values to 28Y042-7F11-1 exposed to 'un-stressed' control conditions.

Eosinophil Shape Change Assay & Binding to Endogenous IL-5

Figure 2:
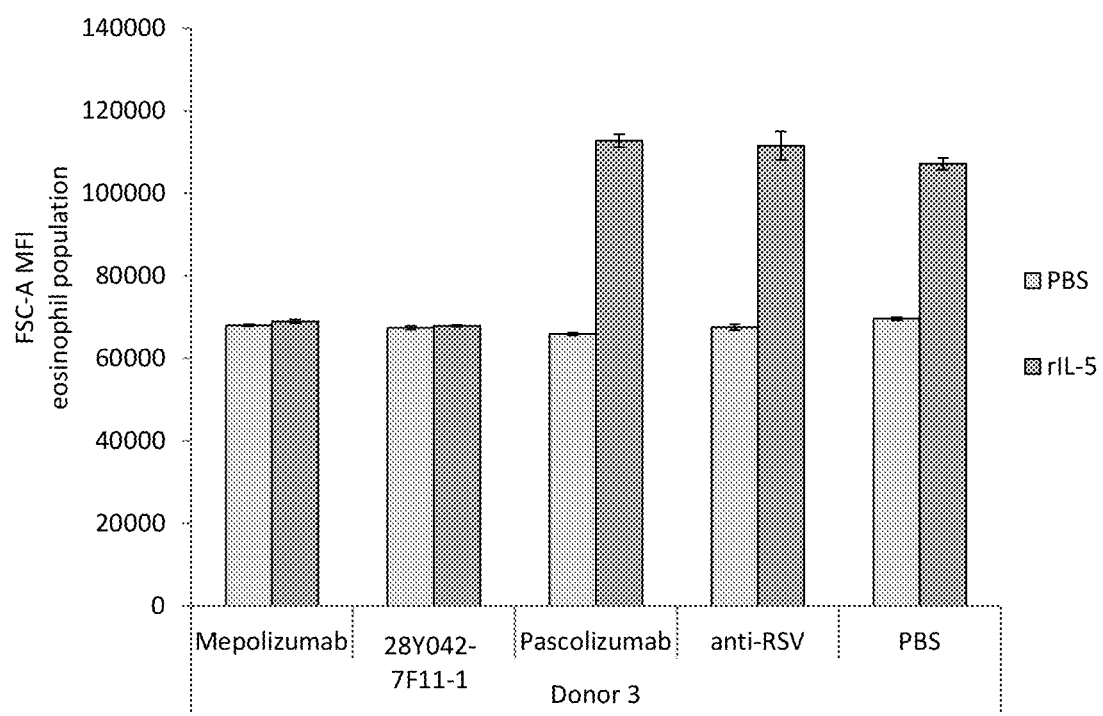
FIG. 2. Inhibition of recombinant IL-5-mediated eosinophil shape change by 28Y042-7F11-1 and mepolizumab in human whole blood. Data shown is representative of 6 donors.

The ability of 28Y042-7F11-1 to inhibit IL-5 mediated eosinophil shape change in human whole blood was assessed. Both mepolizumab and 28Y042-7F11-1 (10 μg/ml) showed inhibition of recombinant IL-5 (10 ng/ml) mediated eosinophil shape change, whereas control antibodies pascolizumab and anti-RSV (Fc disabled) failed to prevent IL-5 mediated eosinophil shape change (FIG. 2).

Figure 3:
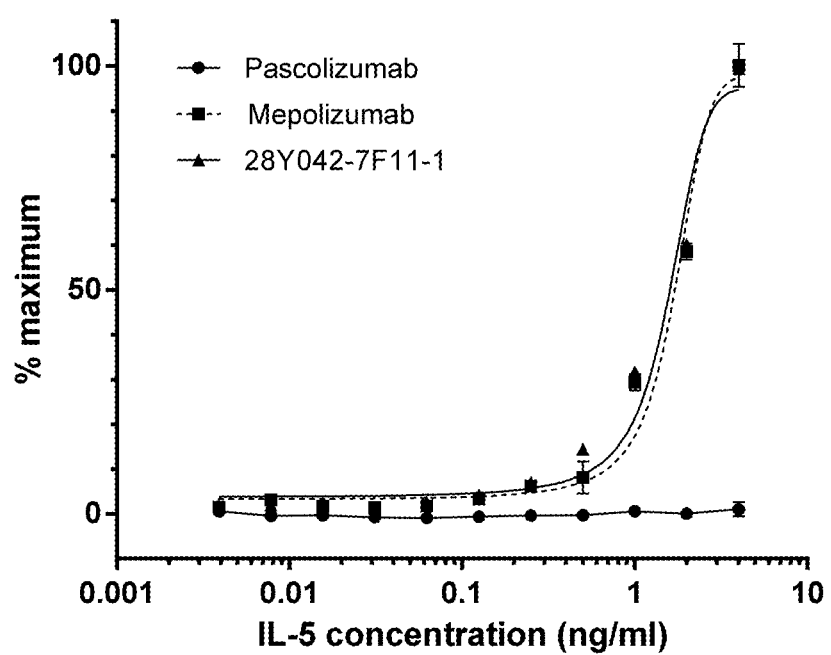
FIG. 3. Binding of native IL-5 to 28Y042-7F11-1 and mepolizumab by ELISA.

The ability of 28Y042-7F11-1 and mepolizumab (both 1 μg/ml) to bind native IL-5 from the supernatant of CD3/CD28-stimulated peripheral blood mononuclear cells (PBMCs), by ELISA was assessed. 28Y042-7F11-1 and mepolizumab bound native IL-5, whilst the control antibody pascolizumab did not. Although the assay demonstrated binding to native IL-5, it was not optimised further to determine accurate $EC_{50}$ values (FIG. 3).

Figure 4:
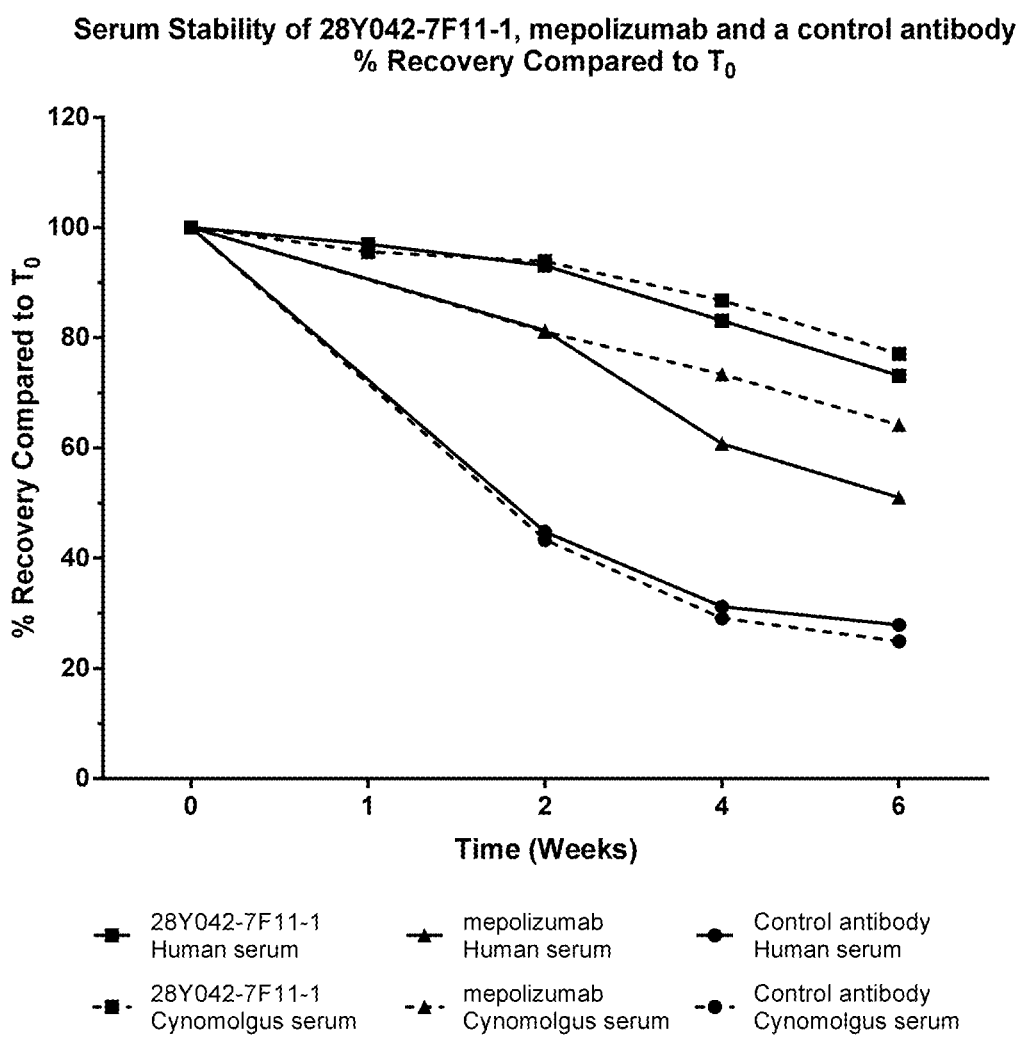
FIG. 4. Comparison of the stability of 28Y042-7F11-1 incubated at 37° C. for 6 weeks in pooled human or cynomolgus monkey serum. Data plotted in comparison to previous results obtained for mepolizumab and an IL-13 specific control antibody.

In Vitro Stability of 28Y042-7F11-1 in Human and Cynomolgus Serum by Immunoassay The ability of 28Y042-7F11-1 to bind recombinant IL-5 was assessed following incubation at 37° C. for 6 weeks in pooled control human or cynomolgus serum (FIG. 4). Following incubation, samples were tested in an MSD immunoassay, where remaining active 28Y042-7F11-1 was captured using immobilised biotinylated IL-5 and then detected using a directly labelled anti-human Fc monoclonal reagent. In both human and cynomolgus serum, the recovery of active 28Y042-7F11-1 showed a gradual drop over time, reaching 73.1% and 77.1% respectively of the $T_0$ concentration after 6 weeks. This compares to historic data obtained for mepolizumab (51.0% [human] and 64.2% [cynomolgus]) and an control antibody specific for IL-13 that is known to have poor stability in this assay (27.9% [human] and 24.9% [cynomolgus]). Results from this study demonstrated that the in vitro human and cynomolgus serum stability of 28Y042-7F11-1 compared favourably to historical values obtained for mepolizumab and suggests 28Y042-7F11-1 behaves in line with expectations for a typical monoclonal antibody.

28Y042-7F11-1 PK/PD Determination in Cynomolgus Monkey

A 9 month non-GLP in vivo pharmacokinetic/pharmacodynamic (PK/PD) study was performed comprising 4 groups of cynomolgus monkey (*Macaca fascicularis*), each group consisting of 2 male and 2 female animals. Animals were administered by intravenous bolus injection on Day 1 with either 28Y042-7F11-1 (0.05 mg/kg or 1 mg/kg), mepolizumab (1 mg/kg), or vehicle. In addition to determining the PK parameters of the injected antibodies, two PD parameters were assessed to compare the activity of 28Y042-7F11-1 to mepolizumab in vivo: a) the level and duration of eosinophil suppression; b) the level and duration of total IL-5 serum concentration.

PK Assessment of 28Y042-7F11-1

PK assessment was performed on cynomolgus serum samples up to 5376 hours (week 32). Analysis revealed that 28Y042-7F11-1 has a 1.8 fold reduction in serum clearance rate compared to mepolizumab (0.105 ml/hr/kg vs 0.185 ml/hr/kg respectively) and an improved half-life of 24.5 days compared to 11.5 days for mepolizumab (Table 19). Table 19 legend/description: Pharmacokinetic parameters determined from the cynomolgus monkey PK study (* median value).

TABLE 19

| Group | Animal | AUC (hr · μg/ml) | $AUC_{inf}$ (hr · μg/ml) | $C_{max}$ (μg/ml) | $T_{max}$ (hr) | Half-life (hr) | MRT (hr) | Cl (ml/hr/kg) | $V_{ss}$ (ml/kg) |
|---|---|---|---|---|---|---|---|---|---|
| 28Y042-7F11-1 | 301 | 493 | 542 | 1.30 | 0.25 | 598 | 672 | 0.0923 | 80.1 |
| (0.05 mg/kg) | 302 | 394 | 467 | 1.20 | 3.00 | 501 | 447 | 0.107 | 74.8 |
| IV | 351 | 427 | 556 | 1.23 | 0.25 | 649 | 484 | 0.0899 | 81.1 |
| | 352 | 515 | 573 | 1.41 | 0.25 | 614 | 630 | 0.0873 | 75.1 |
| | Mean: | 457 | 534 | 1.29 | 0.25* | 590 | 558 | 0.0942 | 77.8 |
| 28Y042-7F11-1 | 401 | 9930 | 9950 | 24.1 | 0.25 | 543 | 735 | 0.100 | 75.1 |
| (1 mg/kg) IV | 402 | 9400 | 9430 | 22.6 | 0.25 | 616 | 748 | 0.106 | 81.3 |
| | 451 | 9840 | 9870 | 23 | 0.25 | 558 | 745 | 0.101 | 77.0 |
| | 452 | 9020 | 9070 | 24 | 0.25 | 603 | 749 | 0.110 | 85.3 |
| | Mean: | 9550 | 9580 | 23.4 | 0.25 | 580 | 744 | 0.105 | 79.7 |
| Mepolizumab | 201 | 5140 | 5190 | 27.7 | 0.25 | 304 | 374 | 0.193 | 76.0 |
| (1 mg/kg) IV | 202 | 5790 | 5850 | 28.9 | 0.25 | 307 | 400 | 0.171 | 71.9 |
| | 251 | 5060 | 5160 | 30.4 | 0.25 | 242 | 302 | 0.194 | 63.8 |
| | 252 | 5390 | 5540 | 28.8 | 0.25 | 253 | 308 | 0.181 | 62.2 |
| | Mean: | 5350 | 5430 | 29.0 | 0.25 | 276 | 346 | 0.185 | 68.5 |

28Y042-7F11-1 Mediated Eosinophil Suppression

Figure 5:
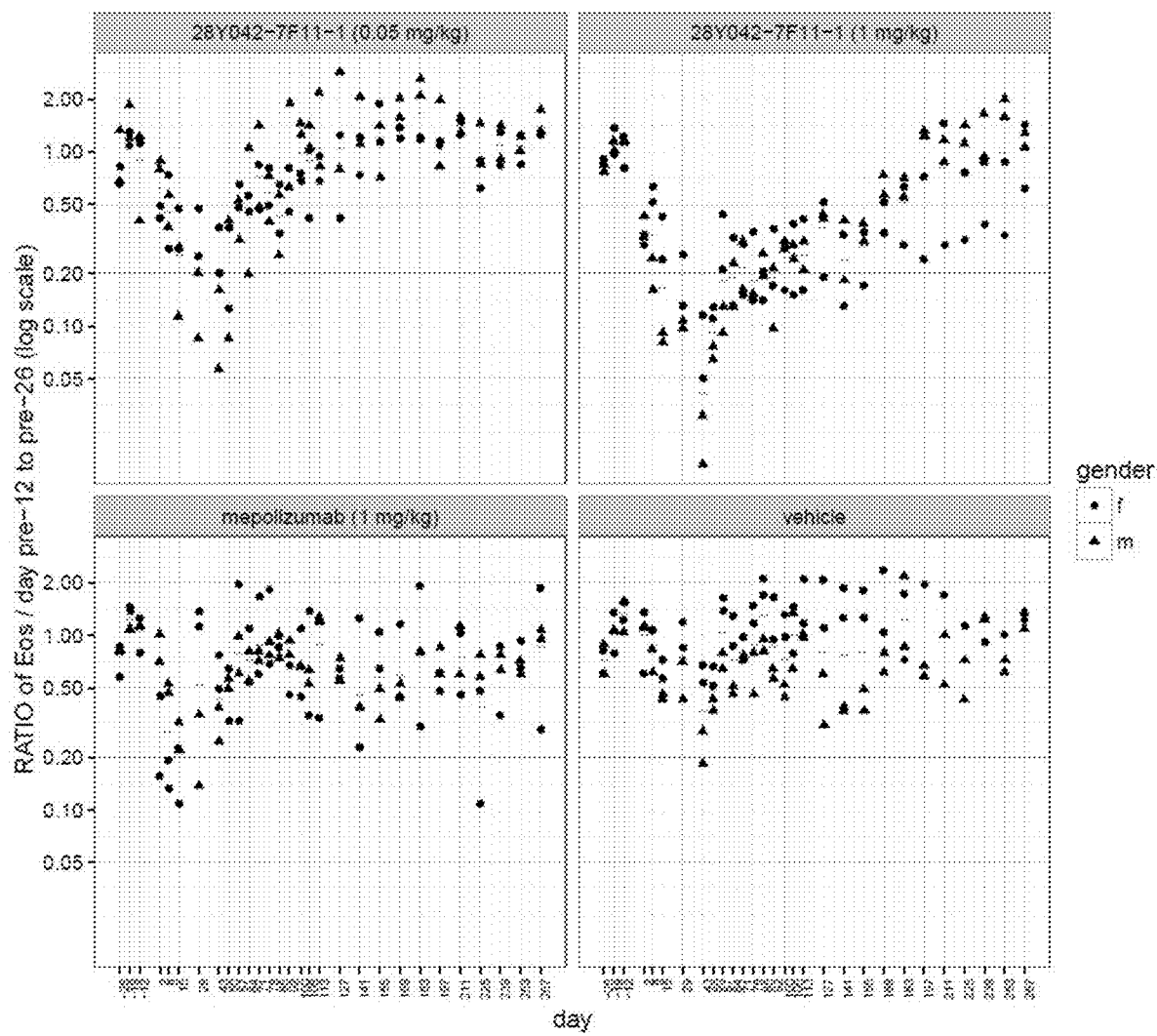
FIG. 5. Plots of proportional animal change relative to average pre-dose eosinophil response. Ratios of the animal eosinophil response against the geometric mean of their pre-dose values (day −12 to −26). Values computed animal-by-animal with overall geometric mean group wise values added as horizontal bars. The solid horizontal line corresponds to 20% of the animal's original eosinophil count. n=4 per group [2 ♀ & 2 ♂]; single iv (intravenous) administration of drug on Study Day 1.

Reduction in eosinophil counts were used as a biomarker for 28Y042-7F11-1 mediated IL-5 neutralisation activity. In vivo, 28Y042-7F11-1 displays an extended duration of eosinophil suppression compared to mepolizumab in cynomolgus monkeys (FIG. 5). 28Y042-7F11-1 when dosed at 1/20th the dose of mepolizumab shows an equivalent or marginally superior suppression of eosinophils, indicating that 28Y042-7F11-1 is at least 20 fold more active than mepolizumab in vivo. Blood eosinophil numbers were ≤50% of the pre-dose value for up to 24 weeks post dosing for 28Y042-7F11-1, compared to 4-7 weeks for mepolizumab, when dosed at 1 mg/kg. Blood eosinophil numbers started showing recovery around week 7 for 28Y042-7F11-1 and week 4 for mepolizumab. These data demonstrate that 3 monthly dosing in humans is achievable and that 6 monthly dosing is also attainable.

Total IL-5 Levels in Serum

Figure 6:
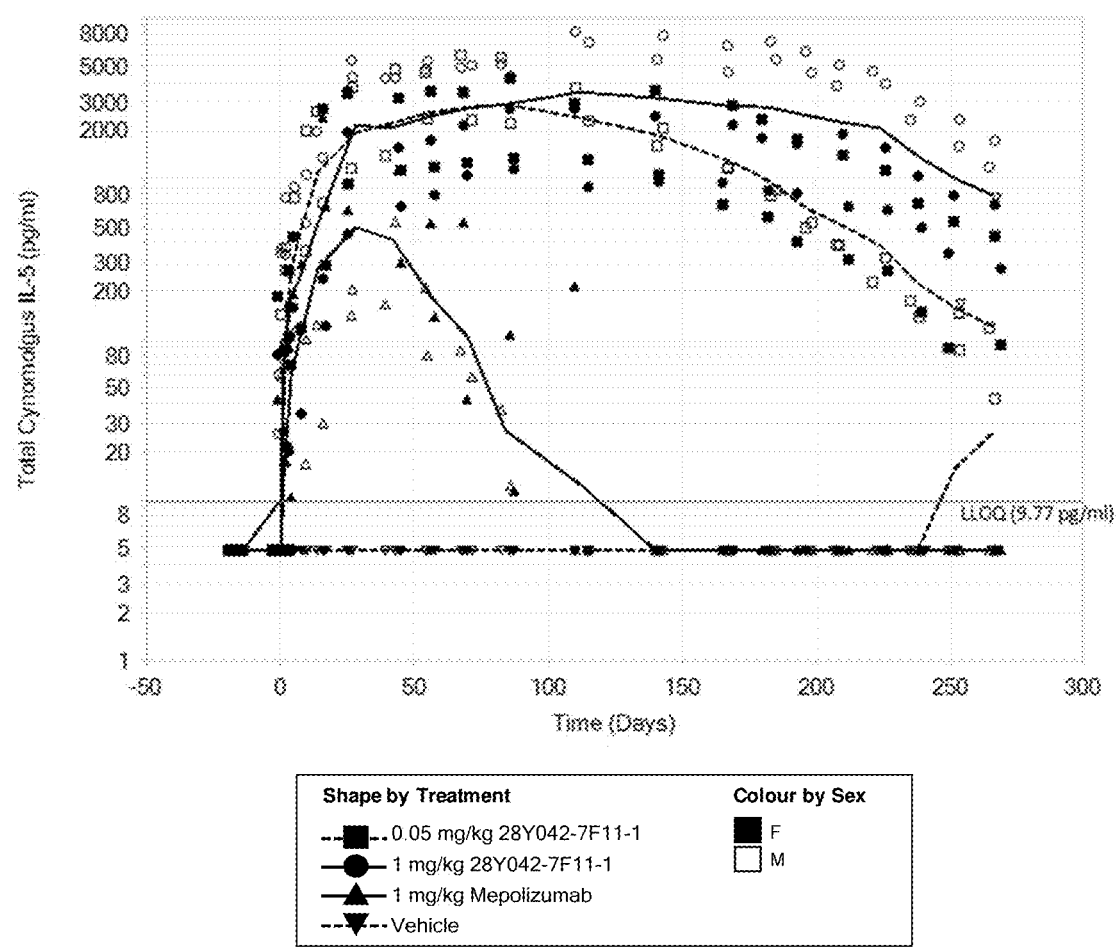
FIG. 6. Serum total IL-5 levels in cynomolgus monkey from the 9-Month PK/PD study (data to day 267/week 38) for animals treated with 28Y042-7F11-1, mepolizumab or vehicle. 28Y042-7F11-1 demonstrated an extended duration and increased magnitude of total IL-5: antibody complex in serum. The lowest level of quantification (LLOQ) of cynomolgus IL-5 was 9.77 pg/ml.
Figure 7:
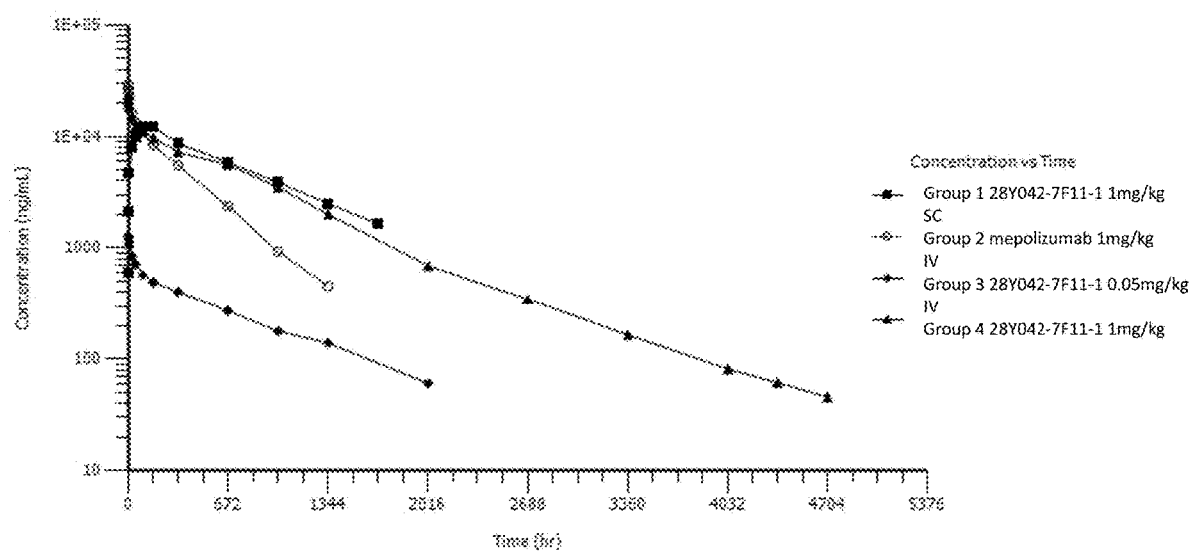
FIG. 7. Mean serum concentration (ng/ml) of 28Y042-7F11-1 and mepolizumab (SB-240563) in cynomolgus monkeys following a single intravenous (IV) or subcutaneous (SC) injection.

The level of total IL-5 (almost exclusively complexed IL-5 with either 28Y042-7F11-1 or mepolizumab) was observed to increase post dose and showed a marked persistence for the two 28Y042-7F11-1 dosed groups compared to the mepolizumab group, where the IL-5 complex started to decline much earlier (FIG. 6). The 1 mg/kg mepolizumab dosed group began to decline after Study Day 29 (672 hrs), the 0.05 mg/kg 28Y042-7F11-1 group began to decline after Study Day 85 (2016 hrs), and the 1 mg/kg 28Y042-7F11-1 began to decline after Study Day 113 (2688 hrs). This reflects the lower affinity as well as the shorter half-life of mepolizumab for IL-5 compared with 28Y042-7F11-1 which continues to maintain a complex with IL-5 for a longer duration.

Non-compartmental pharmacokinetic analysis was also performed for 28Y042-7F11-1 delivered by single intravenous administration and by single subcutaneous administration. Intravenously administrated GSK3511294 demonstrated an increased serum half-life compared to mepolizumab (24 Days vs. 11.5 Days), and a reduction in serum clearance of 1.8-fold (FIG. 4).

Methods: TF-1 Functional Cell Assay

Antibody samples and controls were prepared in 96 well polypropylene plates for initial screening. Antibodies were diluted in cell culture media to a final assay concentration of 200 nM then sterile filtered using filter plate (Pall Corporation multiwell plates, ACRO PREP 96 filter plate, 3.0 µm glass fibre media/0.2 µm BIO-INERT membrane, #5053). Samples were serially diluted 1 in 4 across the plate to produce a 10 point series with a concentration range of (200 nM-7.63 pM). The aim was to generate a single dose response curve to provide an early estimation of the $IC_{50}$ values for the variants. Human IL-5 cytokine (molecular weight of homodimer, 28.5 KDa) for stimulation of cells was diluted in cell culture media and prepared at a final assay concentration of 17.5 pM (0.5 ng/ml), the $EC_{80}$ for human IL-5 stimulation in the assay. Human IL-5 was added to the plate containing the antibody dilution series and incubated for 1 h at room temperature. TF1 cells were washed 3 times with PBS to ensure successful removal of growth factor, GMCSF (Granulocyte Macrophage Colony-Stimulating Factor) used for cell propagation. The cells were seeded in 96 well solid white flat bottomed tissue culture plates at a density of $0.2 \times 10^6$ cells/well. The pre-incubated antibody and cytokine were subsequently added to the cells and further incubated for 3 days at 37° C., 5% $CO_2$. The plates were removed from the incubator and 100 µl of CELLTITER-GLO luminescent reagent (Promega, G7571) was added to the wells of the plates and incubated for 1 hour at room temperature on a plate shaker. The plates were subsequently read on an ENVISION luminescence plate reader (Biomax 501510).

Alternatively for more detailed assessment of the $IC_{50}$ values, the following deviations were used compared to the method described above. A dilution series of the antibodies and controls were prepared in 96 well polypropylene plates. The antibodies were diluted to a final assay concentration of 1 nM in cell culture media and serially diluted 1 in 1.7 across the plate to produce a concentration range of (1 nM-0.000418 pM). Human IL-5 cytokine for stimulation of the cells was diluted in cell culture media and prepared at a final assay concentration of 3 pM.

Methods: BIACORE

Measurement of binding to human IL-5 was done using a BIACORE 4000 (GE Healthcare). The sample flow rate used throughout was 10 µl/min for coupling and regeneration, with 30 µl/min used for kinetic determination. Protein A was immobilised on a Series S CM5 chip (GE Healthcare, BR-1005-30) by primary amine coupling (GE Healthcare, BR-1000-50). This surface was then used to capture the anti-IL-5 antibodies on spot 1 and 5, whilst spots 2 and 4 were used for referencing. Recombinant human IL-5 was then passed over the captured antibodies at 100 nM. A 30 minute dissociation time was used as this was found to be necessary in previous experiments to accurately determine the off-rate of mepolizumab. The binding curves were double referenced with buffer injection (i.e. 0 nM) and the data was fitted with the BIACORE 4000 evaluation software using the 1:1 model. The run was carried out at 25° C., using HBS-EP (Teknova, H8022) as the running buffer and 50 mM NaOH as the regeneration solution.

Analysis of the data found that the off-rates of the antibodies were at the sensitivity limits of the BIACORE 4000 instrument and it was therefore not possible to calculate accurate dissociation rates at 25° C. The run was therefore repeated at 37° C. to increase the dissociation rates, thereby making it possible to calculate accurate dissociation rates for the antibodies.

Methods: MSD-SET Analysis

MSD-SET (MSD solution equilibrium titration) analysis was used in order to determine the affinities of these antibodies to human IL-5 at 25° C. as the dissociation rates were too slow to measure by BIACORE at this temperature. MSD-SET determines the solution phase, equilibrium affinity of antibodies. The method relies on the detection of free antigen at equilibrium in a titrated series of antibody concentrations.

Biotinylated human IL-5 was used at a constant concentration of 30 pM, while the antibody samples were titrated 1 in 3 from 2.5 nM to 0.5 pM, with a final 1 in 10 dilution sample at 0.05 pM on a 96 well polypropylene plate. The titrated antibody and IL-5 were incubated for 24 h at room temperature. After 24 h, antibodies (20 nM in PBS) were coated onto standard bind MSD plates (Meso Scale Discovery, L15XA) for 30 min at room temperature. Plates were then blocked with STARTING BLOCK blocking buffer (Thermo Scientific, #37542) for 30 min with shaking at 700 rpm, followed by three washes with wash buffer. The incubated solutions were added to the MSD plates for 150 s with shaking at 700 rpm followed by one wash. Antigen captured on a plate was detected with a SULFOTAG-labeled streptavidin (Meso Scale Discovery, R32AD-1) by incubation on the plate for 3 min. The plates were washed three times with wash buffer and then read on an MSD SECTOR IMAGER instrument using 1× Read Buffer T with surfactant (Meso Scale Discovery, R92TC-1). The percent free antigen was plotted as a function of titrated antibody using GRAPH-PAD PRISM software and fitted to a quadratic equation.

The affinity for cynomolgus IL-5 at 25° C. was also determined using MSD-SET analysis. The method used was the same as described above, but using a cynomolgus IL-5 concentration of 62.5 pM.

Methods: KINEXA Analysis of 28Y042-7F11-1

In order to generate an accurate affinity determination for 28Y042-7F11-1 binding to human IL-5 at 25° C., KINEXA (kinetic exclusion assay) was used as an alternative to the MSD-SET analyses as the 95% confidence intervals generated for 28Y042-7F11-1 showed that there was a poor fit of the data to the model.

Solution phase affinity measurements were made using Sapidyne's KINEXA 3200 instrument. The method relied on the detection of free antibody at equilibrium in a titrated series of antigen concentrations. For detection, a bead matrix was created using NHS-activated SEPHEROSE beads (GE Healthcare, 17-0906-01) coated with human IL-5. For affinity determination, a fixed concentration of antibody was incubated with a dilution series of human IL-5 concentrations and binding was allowed to reach equilibrium before the samples were run on the KINEXA 3200 instrument. Each solution was passed over an aliquot of the antigen beads where free antibody bound to the antigen coated beads and was detected using an anti-human IgG antibody (DYLIGHT 649-AFFINIPURE F(ab')2 fragment goat anti-human IgG; Jackoson Immunoresearch, 109-496-170), with fresh antigen beads used to measure each sample. Data was analysed using the software inherent to the KINEXA machine, with multiple runs carried out using different starting concentrations of antibody that were above and below the expected affinity of the interaction i.e., 300 pM and 50 pM (concentration driven and affinity driven interactions respectively) and with a range of concentrations of antigen within a single assay that was capable of saturating all the available antibody leaving nearly 100% unbound (10 nM to 4.88 pM for the concentration driven curve, 1 nM to 0.49 pM for the affinity driven curve). The data from the multiple runs was combined analysed using the "n-plot" analysis software inherent to the KINEXA machine to determine the $K_D$ and 95% confidence interval.

Methods: IL-5 Binding of 28Y042-7F11-1 in Competition with Mepolizumab

To determine that 28Y042-7F11-1 bound to the same epitope on human IL-5 as mepolizumab, a competition assay was performed using a FORTEBIO OCTET RED384 biolayer interferometry instrument (BLI). Since human IL-5 is a dimer, a tandem assay format was used where biotinylated human IL-5 at 5 µg/mL in PBSF buffer was captured onto a streptavidin surface (FORTEBIO, 18-5019). This surface was saturated with mepolizumab at 100 nM in PBSF followed by 28Y042-7F11-1 at 100 nM. The process was repeated with 28Y042-7F11-1 saturating the IL-5 surface followed by mepolizumab and self-binning controls were also included. The analysis was run at 25° C., with a plate shaker speed of 1000 rpm. Data was analysed using the instrument's FORTEBIO data analysis.

Methods: SEC Analysis

Analytical size exclusion chromatography (SEC) was carried out to evaluate the purity (% monomer) and retention time of the molecule. Late retention times may indicate potential developability issues with a molecule. SEC was performed using a TSK G3000SWXL, 250A, 5 µm, 30 cm×7.8 mm column on an AGILENT 1100 HPLC system. Running conditions were 200 mM $NaH_2PO_4$, 250 mM NaCl, pH 6.0 at a flow rate of 0.5 ml/min. The load was 20 µg per sample with a run time of 30 minutes. Results were analysed using peak integration software in CHEMSTATION.

Methods: Binding of 28Y042-7F11-1 to Human Fc Receptors Assessed by PROTEON

The binding of 28Y042-7F11-1 to recombinant soluble human Fc gamma receptors (FcγRs) was assessed using the PROTEON XPR36 (BIORAD) biosensor instrument. Antibodies were analysed against a positive control antibody containing a wild type human IgG1 Fc region and a negative control antibody containing two point mutations in the Fc region which reduce the interaction with Fc gamma receptors (L235A/G237A). A further control antibody containing the YTE mutation in its Fc region was also included (28Y042-7F11-1 also contains the YTE mutation).

A murine anti-poly-histidine IgG (ANTI-TETRA-HIS; Qiagen, 34670) was immobilised on a GLM biosensor chip (Bio-Rad, 176-5012) by primary amine coupling (GE Healthcare, BR-1000-50). This surface was used as a capture surface for the poly-histidine tagged human Fc gamma receptors (all in-house generated reagents [except for CD64-Fc; R&D Systems, 1257-FC]). Antibodies to be tested were used as the analyte and passed over at 1024 nM, 256 nM, 64 nM, 16 nM and 4 nM with an injection of 0 nM (i.e., buffer alone) used to double reference the binding curves. The murine anti-poly-histidine IgG surface was regenerated with 100 mM phosphoric acid between interactions. The run was carried out at 25° C. using HBS-EP (Teknova, H8022) as running buffer. Data was analysed for each receptor separately, setting a global R-max and using the equilibrium model inherent to the PROTEON's analysis software.

Methods: Binding of 28Y042-7F11-1 to Human Complement C1q Assessed by PROTEON

Binding of 28Y042-7F11-1 to human recombinant soluble complement C1q was assessed using the PROTEOn XPR36 (BioRad™) biosensor instrument. A control antibody containing the YTE change to its Fc region was included as a control.

The antibodies to be tested were immobilised on a GLC chip (Bio-Rad, 176-5011) by primary amine coupling (GE Healthcare, BR-1000-50). Recombinant C1q (Sigma, C1740) was passed over the immobilised antibodies at 512 nM, 128 nM, 32 nM, 8 nM, 2 nM and 0 nM (i.e., buffer alone) and a blank activated and deactivated flow cell was used to double reference binding curves. The running buffer for binding analysis was HBS-EP (pH7.4, Teknova, H8022) with 10 mM $CaCl_2$. Data were fitted to the equilibrium model, inherent to the PROTEON XPR36 (BioRad™) analysis software using a global R-max value.

Methods: FcRn Binding

The binding affinity of 28Y042-7F11-1 and mepolizumab to human FcRn at pH 6.0 and pH 7.4 was assessed using a BIACORE T200 instrument at 37° C. Human recombinant IL-5 was diluted in acetate buffer pH 5.0 and immobilised to a level of 535 RU by amine coupling on to a CM5 chip (GE, BR100530). 28Y042-7F11-1 or mepolizumab were captured by flowing (5 µl/min) a 100 nM solution of either mAb in HBS-EP (Teknova, H8022) buffer for 24 seconds over the chip surface. Following capture of the antibody via the immobilised IL-5, cycles of varying concentrations (0.5 µM to 32 µM) of human FcRn were flowed over the chip surface at 5 µl/min for 120 seconds contact time followed by 80 seconds dissociation for each cycle. At the completion of each cycle, the chip surface was regenerated using 10 mM Glycine pH 1.5 for 5 seconds at 50 µl/min followed by 10 mM NaOH for 5 seconds at 50 µl/min. FcRn cycles were performed for each concentration at pH 6.0 (HBS-EP+, Teknova, Cat: H8022, pH 6.0) and pH 7.4 (HBS-EP). A molecular weight of 42929 Da for human FcRn was used in the calculations.

Methods: Binding to Native IL-5

The ability of 28Y042-7F11-1, mepolizumab and negative control antibodies (pascolizumab & anti-RSV) to bind native IL-5 was determined. 28Y042-7F11-1, mepolizumab or the control antibodies, were diluted to a concentration of 1 µg/ml/200 µl/well in PBS and incubated on a MAXISORP ELISA plate (Nunc, 10394751) overnight at 4° C. then washed (all washing steps used 200 µl/well PBS supplemented with 0.05% Tween 20. The plate was blocked with 300 µl/well PBS supplemented with 1% BSA (Sigma, A9576) for 2 hours before a 1:2 titration of culture supernatant containing 4 ng/ml native IL-5 was added to the plate. The supernatant was incubated with the antibodies for 1 h at room temperature, washed, then 100 μl/well biotinylated anti-IL-5 antibody (Fisher, MM550CB) at 1 μg/ml diluted in PBS supplemented with 0.5% BSA was added to the plate for 1 h at room temperature. Streptavidin-HRP (GE Healthcare, RPN4401V) was used for detection, diluted 1:5500 in PBS supplemented with 0.5% BSA, (100 μl/well) and incubated for 20 mM at room temperature followed by the addition of 100 μl/well TMB substrate for 5 min after which the reaction was stopped using 100 μl/well 1 M $H_2SO_4$. The absorbance was read at 450 nm using a SPECTRAMAX plate reader (Biomax, 088261; all points were carried out in duplicate). Control conditions using culture supernatant lacking IL-5 or absence of the capture antibody (28Y042-7F11-1, mepolizumab and negative control antibodies) were also assessed.

Native IL-5 was generated by stimulating human isolated PBMCs with anti-CD3 and anti-CD28 antibodies. Blood (100 ml) from a healthy volunteer donor (human) was obtained in sodium heparin (1000 IU/100 ml). Blood was diluted 1:1 with RPMI (Gibco, 31870074) before being separated by density gradient centrifugation for the isolation of the PBMCs using HISTOPAQUE FICOLL and LEUCOSEP tubes (Greiner, 227290), as per the manufacturer's guidelines. Post to isolation, the PBMCs were washed twice with RPMI, (2×5 min spin at 1200 rpm). After the second wash, cells were resuspended in 50 ml RPMI (supplemented with 10% foetal bovine serum, penicillin/streptomycin and L-glutamine), from which a 500 μl sample was taken and mixed 1:1 with TRYPLE EXPRESS (Gibco, 12604-021) and run on a VICELL to obtain a cell count. Plates were precoated with 1 μg/ml anti-CD3 (OKT3, in-house) and 3 μg/ml anti-CD28 (in-house) at 37° C. for 60 mins followed by washing wells once with PBS. Cells were diluted to $1×10^6$/ml and 200 μl/well (2×105 cells) added to the anti-CD3/CD28 pre-coated wells and incubated at 37° C., 5% $CO_2$ for 4 days. Following stimulation, cell supernatants were pooled into a 50 ml falcon tube and spun (5 min, 1200 rpm). The supernatant (45 ml) was recovered into a fresh falcon tube and the cell pellet discarded. BSA (667 μl from Sigma, A9576) was added to 40 ml supernatant (0.5% final concentration) and split equally between 2 VIVASPIN 20 columns (Sartorius, VS0112) and centrifuged at 3600 g (4500 rpm) for 2×10 min to concentrate the supernatant. The enriched supernatant fractions were pooled stored at 4° C. As an assay control, 5 ml original supernatant that had not been spun or had BSA added was also stored at 4° C. Unstimulated supernatant samples were spun in the same way as above and stored at 4° C. to obtain a control supernatant lacking IL-5. The concentration of IL-5 was quantified using a QUANTIKINE ELISA kit (R&D Systems, D5000B).

Methods: Inhibition of IL-5 Mediated Eosinophil Shape Change Assayed by Flow Cytometry This assay was used to measure the inhibition of recombinant IL-5-mediated eosinophil shape change in human whole blood by 28Y042-7F11-1 or mepolizumab (all points were carried out in duplicate). Blood from healthy volunteer donors (human; with associated appropriate consent) was obtained in sodium heparin (1000 IU/100 ml) from the GlaxoSmithKline Stevenage Blood Donation Unit. 28Y042-7F11-1, mepolizumab and control antibodies pascolizumab and anti-RSV were each diluted to obtain a final assay concentration of 10 μg/ml. Antibodies were incubated with an equal volume of recombinant IL-5 (R&D Systems, Lot #091231202) at 10 ng/ml final at 37° C. for 1 h. Following the incubation, each 20 μl sample of antibody/IL-5 complex was added to 80 μl whole blood from one of six donors in a 96 deep well polypropylene plate (Fisher Scientific, 10007621). The plate was incubated at 37° C. for 30 min after which time it was placed on ice and fixed with 250 μl/well for 2 minutes using CELL FIX (BD, 340181) diluted 1:9:30 CELL FIX: water: PBS (this ratio is 4 times more diluted than the manufacturer's recommendation to provide conditions which were not detrimental to eosinophil integrity). Cells were then lysed with 1 ml/well ice cold PHARM LYSE (BioLegend, RBC lysis buffer, 420301) as per the manufacturer's protocol. Samples were spun and supernatant removed before being resuspended in FACS buffer and data acquired on a CANTO II gating eosinophils by their autofluoresence in the PE channel. The effect of 28Y042-7F11-1, mepolizumab, pascolizumab and anti-RSV in the absence of IL-5 was also tested using PBS alone. The effect of IL-5 on eosinophil shape change was also tested in the absence of any antibody, using PBS alone.

Methods: Serum Stability Study

28Y042-7F11-1 was diluted into either neat pooled sterile human serum (GSK Stevenage blood donation unit) or neat pooled sterile cynomolgus serum (from SeraLabs) to give 4 ml of each containing 28Y042-7F11-1 at a target concentration of 120 μg/ml. Each serum sample (human or cynomolgus) was then split into 5×750 μl aliquots into sterile 2 ml microcentrifuge tubes and lids were firmly sealed. One aliquot for each serum species was then immediately placed on dry ice and was allowed to freeze, generating the $T_0$ samples, then transferred to −80° C. for storage. Remaining aliquots were placed into a humidified tissue culture incubator set at 37° C. with 5% $CO_2$. After 1, 2, 4 and 6 weeks, 1 aliquot for each serum species was removed, frozen on dry ice as before, then transferred to −80° C. for storage. The in vitro stability study completed on removal and storage of the 6 week samples.

Samples derived from the in vitro serum stability study were tested in an MSD (Meso Scale Discovery) IL-5 capture immunoassay in order to quantify 28Y042-7F11-1 over the serum incubation time course. Due to the use of biotinylated IL-5 as a capture reagent, only molecules with activity against IL-5 were captured and subsequently detected, therefore any change in recovery detected over time represented loss of active 28Y042-7F11-1. All samples were tested together in a single assay after completion of the 6-week incubation. The IL-5 capture immunoassay was performed using 96-well standard bind MSD plates (MSD, #L15XA-6) which were coated with 50 μl of NEUTRAVIDIN (Thermo-Fisher Scientific, #31000) at 2 μg/ml diluted into tissue culture grade PBS (Sigma-Aldrich, #D8537). Plates were left overnight at +4° C. Coated plates were washed using an automated plate washer (Biotek ELx405) where each well was washed 3 times with 300 μl PBS +0.1% TWEEN-20. After washing, plates were tapped on paper towel to remove residual liquid. All plates were then blocked with 150 μl of assay buffer (PBS +5% BSA (Sigma-Aldrich, #A7030) +1% TWEEN-20 (Fisher Scientific, #BP337)). Plates were incubated at room temperature for 1 hour on a plate rocker (Heidolph TITRAMAX 1000) set to approximately 750 rpm (used throughout) and were then washed as before. Biotinylated human IL-5 (GSK reagent) was diluted to 100 ng/ml in assay buffer and 25 μl of this was added to all wells of the blocked and washed plates. Plates were then incubated at room temperature for at least 1 hour on a plate rocker and were then washed as described previously. During the incubation with biotinylated ILS, the 28Y042-7F11-1 standard curve and test samples were prepared. A 28Y042-7F11-1 standard curve was prepared by diluting to a top concentration of 250 ng/ml in assay buffer. This was then serially diluted using a dilution factor of 2.5 over a total of 11 dilution points, with the 12th point being assay buffer alone as the assay blank. All test serum stability samples were diluted using dilution factors of 2000, 20,000 and 200,000 into assay buffer. Each neat sample was diluted using a minimum of 20 μl between dilutions and by using successive dilutions no greater than a dilution factor of 10 (i.e., a dilution factor of 2000 was achieved by 3 successive 10-fold dilutions followed by a 2-fold dilution). Once the incubation with biotinylated IL-5 was complete and plates had been washed, 25 μl of the 28Y042-7F11-1 standard curve was added in triplicate followed by 25 μl of each test sample at each dilution in duplicate. Plates were then incubated at room temperature for at least 1 hour on a plate rocker and were then washed as before. To detect bound 28Y042-7F11-1, mouse monoclonal anti-human Fc SULFOTAG (labelled using unlabelled antibody from Southern Biotech, #9040-01) was diluted to 500 ng/ml in assay buffer and 25 μl was added to all wells. Plates were then incubated at room temperature for at least 1 hour on a plate rocker and were then washed as before. MSD read buffer T with surfactant was diluted to a 1× working solution with distilled $H_2O$ and then 150 μl was added to all wells. Plates were then read using the SECTOR 6000 MSD imager. The mean concentrations of 28Y042-7F11-1 measured in either human or cynomolgus serum were then normalised to the % of the concentration determined in the $T_0$ samples using:

% of $T_0$=[concentration in test sample/concentration in $T_0$sample]*100

In order to put the serum stability data generated for 28Y042-7F11-1 into context, it was plotted alongside data generated historically for mepolizumab and for an IL-13 specific control antibody. The serum stability set up used for these molecules was identical to that described above except the time points used were 0, 2, 4 and 6 weeks and the batch of human and cynomolgus serum used were different. The analysis of mepolizumab samples was as described above, except a mepolizumab standard curve was used which started from 500 ng/ml and samples were tested using a dilution factor of 1000 only. The analysis of the IL-13 specific control antibody samples were as described above except a the antibody standard curve started from 500 ng/ml, samples were tested using a dilution factor of 1000 only and for the data reported here an IL-13 capture assay was used where biotinylated IL-13 (GSK internal reagent,) at 100 ng/ml in assay buffer was used in place of biotinylated IL-5. Data was normalised to the value at $T_0$ as described above.

Methods: Cynomolgus Monkey in Vivo PK/PD

The study comprised 4 groups of cynomolgus monkey (*Macaca fascicularis*, 2-5 years old, 2-6 kg weight, purpose bred naïve of Mauritius origin), each study group consisting of 2 male and 2 female animals. The cynomolgus monkeys were housed as 4 animals of the same sex per pen with an enriched environment to promote social interaction, play and exploration. Each animal during the study had access to 200 g/day on average of standard ration (PMI Nutrition International Certified primate Diet No. 5S48 (25% protein) and Special Diets Services (SDS) Mazuri Expanded Short (MP (E) short SQC)) diet throughout the study and water ad libitum. Complete haematology cell counts, including eosinophil counts, were determined prior to dosing and then every 1 or 2 weeks post dosing (for 6 months) Animals were administered by intravenous bolus injection on Day 1 with either 28Y042-7F11-1 (0.05 mg/kg or 1 mg/kg), mepolizumab (1 mg/kg), or vehicle. In addition to the haematology cell counts, test substance PK and total IL-5 measurements were performed.

Methods: PK Data

Animals were dosed with test substance on day 1, and sampled (see Table 20 and Table 21) by extracting blood from the femoral vein without the addition of anticoagulant. Sampling was performed as late as possible during the afternoon (between 1-3 pm) to coincide with the haematological (eosinophil) blood sampling schedule. Samples were allowed to clot for at least 1 h at ambient temperature and then centrifuged at 2500 g for 10 min at 4° C. The resultant serum was separated, transferred to uniquely labelled Standard Sarstedt tubes, and frozen immediately over dry ice then stored at −80° C.

The concentration of 28Y042-7F11-1 and mepolizumab from cynomolgus monkey serum samples was determined by an immunoassay using the GYROLAB Work Station (Gyros, P0004943) platform. Biotinylated recombinant human IL-5 capture (in-house reagent) and 28Y042-7F11-1 standards (in cynomolgus serum) were diluted in REXXIP A buffer (Gyros, P0004820) and ALEXA-647 labelled anti-human IgG detection (clone JDC-10) diluted in REXXIP F buffer (Gyros, P0004825). The assay was validated with a range of 30-10,000 ng/ml for 28Y042-7F11-1 and 100-10,000 ng/ml for mepolizumab on a BIOAFFY 1000 CD (Gyros, P0004253). Serum concentration values for 28Y042-7F11-1 were in the expected range. Table 20 legend/description: Cynomolgus blood sampling schedule for the PK and total IL-5 assays. Blood extraction volume was 0.7 ml (0.5 ml where *). Table 21 legend/description: Haematology Sample Collection Schedules.

TABLE 20

Blood Sample Collection Time Points (Time Post Dose in hours) from end of injection on Day 1; [Day No.]

| 0.25 h | 1 h | 3 h | 6 h | 24 h | 48 h | 96 h | 168 h | 336 h | 672 h | 1008 h | 1344 h |
|---|---|---|---|---|---|---|---|---|---|---|---|
| [1] | [1] | [1] | [1] | [2] | [3] | [5] | [8] | [15] | [29] | [43] | [57] |
| 1680 h | 2016 h | 2688 h | 3360 h | 4032 h | 4368 h | 4704 h | 5040 h | 5376 h | 5712 h | 6048 h | 6384 h |
| [71]* | [85] | [113] | [141] | [169] | [183] | [197] | [211] | [225] | [239] | [253] | [267] |

TABLE 21

| Blood Sample Collection Time Points (Time Post Dose in hours) from end of injection on Day 1; [Day No.] | | | | | | | | | | | |
|---|---|---|---|---|---|---|---|---|---|---|---|
| 24 h | 168 h | 336 h | 672 h | 1008 h | 1176 h | 1344 h | 1512 h | 1680 h | 1848 h | 2016 h | 2184 h | 2376 h |
| [2] | [8] | [15] | [29] | [43] | [50] | [57] | [64] | [71] | [78] | [85] | [92] | [100] |
| 2520 h | 2688 h | 3024 h | 3360 h | 3696 h | 4032 h | 4368 h | 4704 h | 5040 h | 5376 h | 5712 h | 6048 h | 6384 h |
| [106] | [113] | [127] | [141] | [155] | [169] | [183] | [197] | [211] | [225] | [239] | [253] | [267] |

Methods: Total IL-5 Data

Animals were dosed, blood sampled and processed as described for PK data collection. Standard curves of cynomolgus IL-5 (2.44-10,000 pg/ml final concentration) were prepared at ×2 final concentration serially diluting 1 in 4 in pooled cynomolgus serum (SeraLab, S-118-D). Four QC spiked IL 5 controls were also prepared at 2× the final concentration required (to account for the 1:2 dilution with the antibody cocktail) using pooled cynomolgus serum (5000, 500, 50 and 0 pg/ml IL-5). Each standard/QC spiked control/serum test sample was then transferred (50 µl) into a new 96-well polypropylene plate. The capture and detection antibody cocktail was prepared using rat anti-human IL-5-biotin conjugate mAb (Southern Biotech, 10118-08) at a final concentration of 0.5 µg/ml as the capture mAb and rat anti-human IL-5-sulfo-tagged mAb (Southern Biotech, 10118-14 (MSD sulfo-tagged in house)) at a final concentration of 0.5 µg/ml as the detection mAb. Both the capture and detection antibodies were prepared in assay buffer (RK/CI Buffer: [6.4 mM EDTA, 5.1 mM EGTA, 50 mM HEPES, 149.2 mM NaCl, 1% Triton X-100, 1% BSA, pH 7.4]) at 2× the final concentration to account for the 1:2 dilution in the standard/sample/control. The antibody cocktail (50 µl) was added to each standard/QC spiked control/test serum sample and incubated for 3 h at room temperature, shaking (600 rpm) in the dark. A streptavidin gold MSD plate (Meso Scale Discovery, L15SA-1) was blocked with 150 µl/well MSD Blocking Buffer (3% MSD Blocker A (Meso Scale Discovery, R93BA-1) in PBS) and incubated for 1 h at room temperature with shaking (600 rpm). Following the 3 h incubation of the antibody cocktail and standards/QC spiked controls/test serum samples, 25 µl/well in duplicate (or triplicate for QC spiked controls) was transferred onto the blocked and washed (SKAN WASHER 300, Skatron Instruments) MSD streptavidin gold plate. The plate was then incubated for 1 h at room temperature with shaking (600 rpm). Following this incubation, the plate was then washed (SKAN WASHER 300, Skatron Instruments). Read Buffer T (2×) was prepared and 150 µl/well was added to each well of the MSD streptavidin gold plate. The electrochemiluminescence was then quantified using the MSD Sector S 600 (Model 1201) within 15 minutes.

Methods: Eosinophil Counts

Reduction in eosinophil counts were used as a biomarker for 28Y042-7F11-1 mediated IL-5 neutralisation activity. Prior to the administration of the test substance, a panel of 39 animals were pre-screened for eosinophil levels (days −51 and −44) and animals with eosinophil levels (≥180 eosinophils/4) selected to go onto the study Animals with higher eosinophil counts were selected based on the assumption that they would provide a larger assay window to measure the level of eosinophil suppression. There was concern that due to the animals being captive bread and living in clean room conditions, they had lower baseline eosinophil counts than wild animals, and these lower eosinophil values when suppressed by drug, may fall below the lowest level of quantification. It also became apparent during the pre-screening phase that some animals displayed a wide fluctuation in eosinophil counts. The cause of this variation is unknown, but could be attributed to multiple factors, such as: environmental, stress, or hormonal changes.

Once the 16 animals were selected for the study, they were re-housed in the study pens (4 animals of the same sex per pen) and allowed to acclimatise to their new surroundings. During the acclimatisation period, 3 pre-dose haematology counts were performed (days −21, −14, and −7). Animals were dosed with test substance on day 1, and sampled by extracting 0.5 ml blood from the femoral vein using EDTA as an anticoagulant. Sampling was performed as late as possible during the afternoon (between 1-3 pm) to control for diurnal variation in blood eosinophil levels. After collection, samples were processed within 60 min of final sample collection for each time point and measured quantitatively using an ADVIA 120 haematology analyser (Siemens) using both the Peroxidase method and the Basophil/Lobularity method.

Example 2

28Y042-7F11-1 was also evaluated in 4-week single dose and 26-week repeat dose GLP toxicity (10 and 100 mg/kg/week) studies. In these studies 28Y042-7F11-1 has been administered subcutaneously to cynomolgus monkeys. The off-dose phase of the 26-week study is ongoing (May 2017), therefore, an interim report presenting data generated during pretreatment through the end of the dosing period is reported here. The systemic exposures achieved in this study are presented in Table 22. Standard methodologies were used to conduct these studies and related analyses. Table 22 legend/description: Comparative assessment of mean systemic exposure following subcutaneous administration of 28Y042-7F11-1 in cynomolgus monkeys. Table 23 legend/description: Mean pharmacokinetic parameters of 28Y042-7F11-1 in cynomolgus monkeys following a single IV or SC injection. Table 24 legend/description: Safety margins when comparing cynomologus monkey NOAEL data with predicted human data at doses to be administered subcutaneously ('safety cover').

TABLE 22

| | Dose | | AUC (µg · h/mL)$^a$ | | $C_{max}$ (µg/mL) | | $T_{max}$ (h) | |
|---|---|---|---|---|---|---|---|---|
| Duration | (mg/kg) | Sex | Day 1 | Week 14 | Day 1 | Week 14 | Day 1 | Week 14 |
| Single Dose 4-Week$^b$ | 10 | M/F | 58900 | NA | 131 | NA | 84 | NA |
| | 100 | M/F | 551000 | NA | 1200 | NA | 84 | NA |

TABLE 22-continued

| Duration | Dose (mg/kg) | Sex | AUC (µg · h/mL)[a] Day 1 | AUC (µg · h/mL)[a] Week 14 | $C_{max}$ (µg/mL) Day 1 | $C_{max}$ (µg/mL) Week 14 | $T_{max}$ (h) Day 1 | $T_{max}$ (h) Week 14 |
|---|---|---|---|---|---|---|---|---|
| Repeat Dose 26-Week[b,c] | 10 | M/F | 104000 (85100-138000) | 1160000 (40300-185000) | 125 (113-153) | 149 (101-221) | 120 | 120 |
|  | 100 | M/F | 837000 (671000-983000) | 1120000 (898000-1290000) | 1200 (1110-1270) | 1390 (1090-1610) | 72 | 96 |

Key:
[a] AUC(0-t) = area under the plasma concentration-time curve from 0 to 672 h (4 week) post single dose and 0 to 2016 h (12 week) after repeat administration.
[b] n = 3/sex/group; sexes combined since no marked differences between sexes exposure to 28Y042-7F11-1.
[c] 5/sex/group at 10 mg/kg dose and n = 3/sex/group for 100 mg/kg dose; sexes combined since no marked differences between sexes exposure to 28Y042-7F11-1. First dose of drug administered on Day 1; second dose administered on Week 14
No observed adverse effect levels (NOAELs) are indicated in bold.
Values in brackets represent the range.
$C_{max}$ = maximum concentration
NA—not applicable
$T_{max}$ = time to maximum observed concentration

TABLE 23

|  | Intravenous Dose (mg/kg) | Intravenous Dose (mg/kg) | Subcutaneous Dose (mg/kg) |
|---|---|---|---|
| Parameter | 0.05 | 1 | 1 |
| $C_{max}$ (µg/mL) | 1.29 | 23.4 | 12.5 |
| $AUC_{0-t}$ (hr*µg/mL) | 457 | 9550 | 9270 |
| CL (mL/hr/kg) | 0.0942 | 0.105 | 0.0974[1] |
| Vss (mL/kg) | 77.8 | 79.7 | 74.0[2] |
| T½ (days) | 25 | 24 | 22 |
| Bioavailability (%) | NA | NA | 111 |

NA = not applicable
[1] CL/F
[2] Vz/F

TABLE 24

| Predicted Human Cmax and AUC | | | | Safety cover (vs. Monkey NOAEL) | | |
|---|---|---|---|---|---|---|
| Dose (mg) | Dose (mg/kg)[1] | Cmax (µg/mL) | AUC (µg*h/mL) | Dose cover[2] | Cmax Cover | Cover AUC |
| 2 | 0.03 | 0.226 | 323 | 3500x | 6156x | 3471x |
| 10 | 0.14 | 1.13 | 1613 | 700x | 1231x | 694x |
| 30 | 0.43 | 3.39 | 4840 | 233x | 410x | 231x |
| 100 | 1.43 | 11.3 | 16132 | 70x | 123x | 69x |
| 300 | 4.29 | 33.9 | 48396 | 23x | 41x | 23x |

[1] assuming a 70 kg subject;
[2] dose (expressed in mg/kg) cover

Example 3

Informal Sequence Listing

Underlining below identifies CDR sequences, according to the Kabat definition of CDRs, in the variable heavy and variable light chain portions of the antibodies or the nucleic acid sequences encoding these CDR sequences. For example, in SEQ ID NO: 1 the frameworks and CDRs are presented as plaintext framework1, underlined CDR1, plaintext framework2, underlined CDR2, plaintext framework3, underlined CDR3 and plaintext framework4 in order from the amino proximal portion to the carboxy terminal portion of the sequences presented. This scheme is used in SEQ ID NO:s 1-4 for example Amino terminal methionine residues shown in these sequences can be cleaved. Thus, the sequences here showing an amino terminal methionine residue should also be considered to disclose the cleaved versions of these proteins lacking such an amino terminal methionine residue. Nucleic acids sequences are presented as DNA nucleic acid sequences and include "t" nucleic acid residues, the corresponding RNA sequence should also be considered as disclosed such that "t" nucleic acid residues may also be regarded as disclosing a "u" nucleic acid residue. Additionally, the 5' proximal "atg" start codon and the 3' proximal "taa," "tag," and "tga" stop codons have been omitted from the cDNA nucleic acid sequences below.

28Y042-7F11-1 FULL LENGTH HEAVY CHAIN
SEQ ID NO: 1
QVTLRESGPALVKPTQTLTLTCTVSGFSLTGSSVHWVRQPPGKGLEWLGV

IWASGGTDYNSALMSRLSISKDTSRNQVVLTMTNMDPVDTATYYCARDPP

SGLLRLDYWGRGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLYITREPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

28Y042-7F11-1 FULL LENGTH LIGHT CHAIN
SEQ ID NO: 2
DIVMTQSPDSLAVSLGERATINCKSSQSLLNSGNQKNYLAWYQQKPGQP

PKLLIYGASTRESGVPDRFSGSGSGTDFTLTISSLQAEDVAVYYCQNVH

SFPFTFGGGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC

28Y042-7F11-1 VH
SEQ ID NO: 3
QVTLRESGPALVKPTQTLTLTCTVSGFSLTGSSVHWVRQPPGKGLEWLG

VIWASGGTDYNSALMSRLSISKDTSRNQVVLTMTNMDPVDTATYYCARD

PPSGLLRLDYWGRGTLVTVSS

```
28Y042-7F11-1 VL
                                        SEQ ID NO: 4
DIVMTQSPDSLAVSLGERATINCKSSQSLLNSGNQKNYLAWYQQKPGQP

PKLLIYGASTRESGVPDRFSGSGSGTDFTLTISSLQAEDVAVYYCQNVH

SFPFTFGGGTKLEIKR

28Y042-7F11-1 CDRH1
                                        SEQ ID NO: 5
GSSVH

28Y042-7F11-1 CDRH2
                                        SEQ ID NO: 6
VIWASGGTDYNSALMS

28Y042-7F11-1 CDRH3
                                        SEQ ID NO: 7
DPPSGLLRLDY

28Y042-7F11-1 CDRL1
                                        SEQ ID NO: 8
KSSQSLLNSGNQKNYLA

28Y042-7F11-1 CDRL2
                                        SEQ ID NO: 9
GASTRES

28Y042-7F11-1 CDRL3
                                        SEQ ID NO: 10
QNVHSFPFT

HUMAN IL-5 (MATURE PROTEIN)
                                        SEQ ID NO: 11
IPTEIPTSALVKETLALLSTHRTLLIANETLRIPVPVHKNHQLCTEEIFQ

GIGTLESQTVQGGTVERLFKNLSLIKKYIDGQKKKCGEERRRVNQFLDYL

QEFLGVMNTEWIIES

HUMAN IL-5 RECEPTOR SUBUNIT ALPHA ISOFORM 1
(MATURE PROTEIN)
                                        SEQ ID NO: 12
DLLPDEKISLLPPVNFTIKVTGLAQVLLQWKPNPDQEQRNVNLEYQVKIN

APKEDDYETRITESKCVTILHKGFSASVRTILQNDHSLLASSWASAELHA

PPGSPGTSIVNLTCTTNTTEDNYSRLRSYQVSLHCTWLVGTDAPEDTQYF

LYYRYGSWTEECQEYSKDTLGRNIACWFPRTFILSKGRDWLAVLVNGSSK

HSAIRPFDQLFALHAIDQINPPLNVTAEIEGTRLSIQWEKPVSAFPIHCF

DYEVKIHNTRNGYLQIEKLMTNAFISIIDDLSKYDVQVRAAVSSMCREAG

LWSEWSQPIYVGNDEHKPLREWFVIVIMATICFILLILSLICKICHLWIK

LFPPIPAPKSNIKDLFVTTNYEKAGSSETEIEVICYIEKPGVETLEDSVF

DNA ENCODING 28Y042-7F11-1 FULL LENGTH HEAVY CHAIN
WITH LEADER SEQUENCE
                                        SEQ ID NO: 13
atgggctggtcctgcatcatcctgtttctggtggccaccgccaccggtgt gcacagccaggtgaccctgagggagagcggccccgccctggtgaagccca cacagaccctcactctgacctgcaccgtgagcggcttcagcctgaccggc tctagcgtccactgggtgaggcagcccccggcaagggcctggagtggct gggcgtgatctgggcaagcggggggacggactacaactcggccctgatga gcaggctctccatcagcaaggacaccagcggaaccaggtggtgctgacc atgaccaacatggaccccgtggacaccgccacctattactgcgccaggga ccctccctccggcctgctgaggctggactactggggcaggggaacactag tgaccgtgtccagcgccagcaccaagggcccagcgtgaccccctggccc ccagcagcaagagcaccagcggcggcacagccgccctgggctgcctggtg aaggactacttccccgagcccgtgaccgtgtcctggaacagcggagccct gaccagcggcgtgcacaccttccccgccgtgctgcagagcagcggcctgt acagcctgagcagcgtggtgaccgtgcccagcagcagcctgggcacccag acctacatctgtaacgtgaaccacaagcccagcaacaccaaggtggacaa gcgggtggagcccaagagctgtgacaagacccacacctgcccccctgcc ctgcccccgagctgctgggaggccccagcgtgttcctgacccccccaagc ctaaggacacccctgtacatcaccagagaacccgaggtgacctgtgtggtg gtggatgtgagccacgaggaccctgaggtgaagttcaactggtacgtgga cggcgtggaggtgcacaatgccaagaccaagcccagggaggagcagtaca acagcacctaccgggtggtgtccgtgctgaccgtgctgcaccaggattgg ctgaacggcaaggagtacaagtgtaaggtgtccaacaagggcctgcctgc ccctatcgagaaaaccatcagcaaggccaagggccagccagagagcccc aggtgtacaccctgccccctagcagagaggagatgaccaagaaccaggtg tccctgacctgcctggtgaagggcttctaccccagcgacatcgccgtgga gtgggagagcaacggccagcccgagaacaactacaagaccaccccccctg tgctggacagcgatggcagcacttcctgtacagcaagctgaccgtggaca agagcagatggcagcagggcaacgtgttcagctgctccgtgatgcacgag gccctgcacaatcactacacccagaagagcctgagcctgtcccctggcaa g DNA ENCODING 28Y042-7F11-1 FULL LENGTH LIGHT CHAIN
WITH LEADER SEQUENCE
                                        SEQ ID NO: 14
atgggctggtcctgcatcatcctgtttctggtggccaccgccaccggtgt gcacagcgacatcgtgatgacccagtctcccgattcactggccgtgagcc tgggcgagagggccaccatcaactgcaagagcagccagagcctcctgaac agcggcaaccagaagaactacctggcctggtaccagcagaaacccggcca gcccccaagctgctgatctatggcgcctccaccagggagagcggcgtgc cagacaggtttagcggcagcggcagcggcaccgacttcaccctgacaatc agcagcctgcaggccgaggacgtggccgtgtactactgccagaacgtcca cagcttcccttcaccttcggcggggaaccaagctggagatcaagcgta cggtggccgccccagcgtgttcatcttcccccccagcgatgagcagctg aagagcggcaccgccagcgtggtgtgtctgctgaacaacttctacccccg ggaggccaaggtgcagtggaaggtggacaatgccctgcagagcggcaaca gccaggagagcgtgaccgagcaggacagcaaggactccacctacagcctg agcagcaccctgaccctgagcaaggccgactacgagaagcacaaggtgta cgcctgtgaggtgacccaccaggggcctgtccagccccgtgaccaagagct tcaaccggggcgagtgc DNA ENCODING 28Y042-7F11-1 HEAVY CHAIN VARIABLE
REGION
                                        SEQ ID NO: 15
caggtgaccctgagggagagcggccccgccctggtgaagcccacacagac cctcactctgacctgcaccgtgagcggcttcagcctgaccggctctagcg tccactgggtgaggcagccccccggcaagggcctggagtggctgggcgtg
``` atctgggcaagcggggggacggactacaactcggccctgatgagcaggct ctccatcagcaaggacaccagccggaaccaggtggtgctgaccatgacca acatggaccccgtggacaccgccacctattactgcgccagggaccctccc tccggcctgctgaggctggactactggggcaggggaacactagtgaccgt gtccagc DNA ENCODING 28Y042-7F11-1 LIGHT CHAIN VARIABLE
REGION
SEQ ID NO: 16
gacatcgtgatgacccagtctcccgattcactggccgtgagcctgggcga gagggccaccatcaactgcaagagcagccagagcctcctgaacagcggca accagaagaactacctggcctggtaccagcagaaacccggccagccccc aagctgctgatctatggcgcctccaccagggagagcggcgtgccagacag gtttagcggcagcggcagcggcaccgacttcaccctgacaatcagcagcc tgcaggccgaggacgtggccgtgtactactgccagaacgtccacagcttc cccttcaccttcggcggggggaaccaagctggagatcaagcgt DNA ENCODING 28Y042-7F11-1 FULL LENGTH HEAVY CHAIN
SEQ ID NO: 17
caggtgaccctgagggagagcggccccgccctggtgaagcccacacagac cctcactctgacctgcaccgtgagcggcttcagcctgaccggctctagcg tccactgggtgaggcagccccccggcaagggcctggagtggctgggcgtg atctgggcaagcggggggacggactacaactcggccctgatgagcaggct ctccatcagcaaggacaccagccggaaccaggtggtgctgaccatgacca acatggaccccgtggacaccgccacctattactgcgccagggaccctccc tccggcctgctgaggctggactactggggcaggggaacactagtgaccgt gtccagcgccagcaccaagggcccagcgtgttcccctggcccccagca gcaagagcaccagcggcggcacagccgccctgggctgcctggtgaaggac tacttccccgagcccgtgaccgtgtcctggaacagcggagccctgaccag cggcgtgcacaccttccccgccgtgctgcagagcagcggcctgtacagcc tgagcagcgtggtgaccgtgcccagcagcagcctgggcacccagacctac atctgtaacgtgaaccacaagcccagcaacaccaaggtggacaagcgggt ggagcccaagagctgtgacaagacccacacctgccccccctgccctgccc ccgagctgctgggaggcccagcgtgttcctgttcccccccaagcctaag gacaccctgtacatcaccagagaacccgaggtgacctgtgtggtggtgga tgtgagccacgaggaccctgaggtgaagttcaactggtacgtggacggcg tggaggtgcacaatgccaagaccaagcccagggaggagcagtacaacagc acctaccgggtggtgtccgtgctgaccgtgctgcaccaggattggctgaa cggcaaggagtacaagtgtaaggtgtccaacaaggccctgcctgcccta tcgagaaaaccatcagcaaggccaagggccagcccagagagccccaggtg tacaccctgccccctagcagagaggagatgaccaagaaccaggtgtccct gacctgcctggtgaagggcttctaccccagcgacatcgccgtggagtggg agagcaacggccagcccgagaacaactacaagaccaccccccctgtgctg gacagcgatggcagcttcttcctgtacagcaagctgaccgtggacaagag cagatggcagcagggcaacgtgacagctgctccgtgatgcacgaggccct gcacaatcactacacccagaagagcctgagcctgtccctggcaag DNA ENCODING 28Y042-7F11-1 FULL LENGTH LIGHT CHAIN
SEQ ID NO: 18
gacatcgtgatgacccagtctcccgattcactggccgtgagcctgggcga gagggccaccatcaactgcaagagcagccagagcctcctgaacagcggca accagaagaactacctggcctggtaccagcagaaacccggccagccccc aagctgctgatctatggcgcctccaccagggagagcggcgtgccagacag gtttagcggcagcggcagcggcaccgacttcaccctgacaatcagcagcc tgcaggccgaggacgtggccgtgtactactgccagaacgtccacagcttc cccttcaccttcggcggggggaaccaagctggagatcaagcgtacggtggc cgcccccagcgtgttcatcttcccccccagcgatgagcagctgaagagcg gcaccgccagcgtggtgtgtctgctgaacaacttctaccccgggaggcc aaggtgcagtggaaggtggacaatgccctgcagagcggcaacagccagga gagcgtgaccgagcaggacagcaaggactccacctacgcctgagcagca ccctgaccctgagcaaggccgactacgagaagcacaaggtgtacgcctgt gaggtgacccaccagggcctgtccagccccgtgaccaagagcttcaaccg gggcgagtgc

28Y042-7F11-1 HEAVY CHAIN LEADER SEQUENCE
SEQ ID NO: 19
MGWSCIILFLVATATGVHS

28Y042-7F11-1 HEAVY CHAIN LEADER SEQUENCE
SEQ ID NO: 20
MGWSCIILFLVATATGVHS

28Y042-7F11-1 HEAVY CHAIN FR4 SEQUENCE
SEQ ID NO: 21
WGRGTLVTVSS

The present invention now being fully described, it will be apparent to one of ordinary skill in the art that many changes and modifications can be made thereto without departing from the spirit or scope of the appended claims.

The material in the ASCII text file named "PU66209T_US_WO_FF_SeqList [,]," created on May 23, 2018 and having a size of 21,851 bytes is incorporated herein by reference in its entirety.

What is claimed is:

1. A composition comprising a nucleic acid encoding an IL-5 binding protein or a fragment thereof comprising a heavy chain and a light chain, wherein a) the heavy chain comprises a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and b) the light chain comprises a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and wherein the IL-5 binding protein comprises a human IgG1 heavy chain Fc domain comprising:

a) a tyrosine residue at position 252 (265 according to Kabat numbering), a threonine residue at position 254 (267 according to Kabat numbering) and a glutamic acid residue at position 256 (269 according to Kabat numbering);

b) a leucine residue at position 108 according to Kabat numbering in the heavy chain variable region; or c) a combination thereof.

2. The composition of claim 1, wherein the IL-5 binding protein comprises a human IgG1 heavy chain Fc domain having a tyrosine residue at position 252 (265 according to Kabat numbering), a threonine residue at position 254 (267 according to Kabat numbering) and a glutamic acid residue at position 256 (269 according to Kabat numbering).

3. The composition of claim 2, wherein the IL-5 binding protein comprises a heavy chain comprising the amino acid sequence of SEQ ID NO: 1.

4. The composition of claim 3, wherein the nucleic acid comprises the sequence of SEQ ID NO:17.

5. The composition of claim 1, wherein the IL-5 binding protein comprises a leucine residue at position 108 according to Kabat numbering in the heavy chain variable region.

6. The composition of claim 5, wherein the heavy chain variable region comprises the amino acid sequence of SEQ ID NO: 3.

7. The composition of claim 6, wherein the nucleic acid comprises the sequence of SEQ ID NO: 15.

8. The composition of claim 1, wherein the IL-5 binding protein comprises a light chain variable region comprising at least 85% sequence identity with SEQ ID NO: 4.

9. The composition of claim 8, wherein the light chain variable region comprises the amino acid sequence of SEQ ID NO: 4.

10. The composition of claim 9, wherein the nucleic acid comprises the sequence of SEQ ID NO: 16.

11. The composition of claim 1, wherein the IL-5 binding protein comprises a light chain comprising at least 85% sequence identity with SEQ ID NO: 2.

12. The composition of claim 11, wherein the light chain comprises the amino acid sequence of SEQ ID NO: 2.

13. The composition of claim 12, wherein the nucleic acid comprises the sequence of SEQ ID NO: 18.

14. The composition of claim 1, wherein the nucleic acid comprises the sequences of SEQ ID NO: 17 and SEQ ID NO: 18.

15. The composition of claim 1, wherein the nucleic acid comprises the sequences of SEQ ID NO: 15 and SEQ ID NO: 16.

16. The composition of claim 1, wherein the nucleic acid comprises the sequences of SEQ ID NO: 13 and SEQ ID NO: 14.

* * * * *

SEQUENCE LISTING

<160> NUMBER OF SEQ ID NOS: 21

<210> SEQ ID NO 1
<211> LENGTH: 449
<212> TYPE: PRT
<213> ORGANISM: Artificial Sequence
<220> FEATURE:

<223> OTHER INFORMATION: Amino acid sequence identified using molecular
      biology techniques.

<400> SEQUENCE: 1

```
Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Gly Ser
            20                  25                  30

Ser Val His Trp Val Arg Gln Pro Pro Gly Lys Gly Leu Glu Trp Leu
        35                  40                  45

Gly Val Ile Trp Ala Ser Gly Gly Thr Asp Tyr Asn Ser Ala Leu Met
    50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Gly Leu Leu Arg Leu Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 2
<211> LENGTH: 220
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 3
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 3

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Gly Ser
                20                  25                  30

Ser Val His Trp Val Arg Gln Pro Pro Gly Lys Gly Leu Glu Trp Leu
            35                  40                  45

Gly Val Ile Trp Ala Ser Gly Gly Thr Asp Tyr Asn Ser Ala Leu Met
50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Gly Leu Leu Arg Leu Asp Tyr Trp Gly Arg Gly
            100                 105                 110

Thr Leu Val Thr Val Ser Ser
        115

<210> SEQ ID NO 4
<211> LENGTH: 114
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
            100                 105                 110

Lys Arg

<210> SEQ ID NO 5
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 5

Gly Ser Ser Val His
1               5

<210> SEQ ID NO 6
<211> LENGTH: 16
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 6

```
Val Ile Trp Ala Ser Gly Gly Thr Asp Tyr Asn Ser Ala Leu Met Ser
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 7

Asp Pro Pro Ser Gly Leu Leu Arg Leu Asp Tyr
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 8

Lys Ser Ser Gln Ser Leu Leu Asn Ser Gly Asn Gln Lys Asn Tyr Leu
1               5                   10                  15

Ala

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 9

Gly Ala Ser Thr Arg Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 10

Gln Asn Val His Ser Phe Pro Phe Thr
1               5

<210> SEQ ID NO 11
<211> LENGTH: 115
<212> TYPE: PRT
<213> ORGANISM: Homo sapien

<400> SEQUENCE: 11

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
                20                  25                  30

Ile Pro Val Pro Val His Lys Asn His Gln Leu Cys Thr Glu Glu Ile
            35                  40                  45
```

Phe Gln Gly Ile Gly Thr Leu Glu Ser Gln Thr Val Gln Gly Gly Thr
 50                  55                  60

Val Glu Arg Leu Phe Lys Asn Leu Ser Leu Ile Lys Lys Tyr Ile Asp
 65                  70                  75                  80

Gly Gln Lys Lys Lys Cys Gly Glu Glu Arg Arg Arg Val Asn Gln Phe
                 85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 12
<211> LENGTH: 400
<212> TYPE: PRT
<213> ORGANISM: Homo sapien

<400> SEQUENCE: 12

Asp Leu Pro Asp Glu Lys Ile Ser Leu Leu Pro Pro Val Asn Phe
 1               5                  10                  15

Thr Ile Lys Val Thr Gly Leu Ala Gln Val Leu Leu Gln Trp Lys Pro
            20                  25                  30

Asn Pro Asp Gln Glu Gln Arg Asn Val Asn Leu Glu Tyr Gln Val Lys
         35                  40                  45

Ile Asn Ala Pro Lys Glu Asp Asp Tyr Glu Thr Arg Ile Thr Glu Ser
 50                  55                  60

Lys Cys Val Thr Ile Leu His Lys Gly Phe Ser Ala Ser Val Arg Thr
 65                  70                  75                  80

Ile Leu Gln Asn Asp His Ser Leu Leu Ala Ser Ser Trp Ala Ser Ala
                 85                  90                  95

Glu Leu His Ala Pro Pro Gly Ser Pro Gly Thr Ser Ile Val Asn Leu
            100                 105                 110

Thr Cys Thr Thr Asn Thr Thr Glu Asp Asn Tyr Ser Arg Leu Arg Ser
            115                 120                 125

Tyr Gln Val Ser Leu His Cys Thr Trp Leu Val Gly Thr Asp Ala Pro
130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175

Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
            195                 200                 205

Gln Leu Phe Ala Leu His Ala Ile Asp Gln Ile Asn Pro Pro Leu Asn
210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
            275                 280                 285

Arg Ala Ala Val Ser Ser Met Cys Arg Glu Ala Gly Leu Trp Ser Glu
290                 295                 300

```
Trp Ser Gln Pro Ile Tyr Val Gly Asn Asp Glu His Lys Pro Leu Arg
305                 310                 315                 320

Glu Trp Phe Val Ile Val Ile Met Ala Thr Ile Cys Phe Ile Leu Leu
            325                 330                 335

Ile Leu Ser Leu Ile Cys Lys Ile Cys His Leu Trp Ile Lys Leu Phe
            340                 345                 350

Pro Pro Ile Pro Ala Pro Lys Ser Asn Ile Lys Asp Leu Phe Val Thr
            355                 360                 365

Thr Asn Tyr Glu Lys Ala Gly Ser Ser Glu Thr Glu Ile Glu Val Ile
            370                 375                 380

Cys Tyr Ile Glu Lys Pro Gly Val Glu Thr Leu Glu Asp Ser Val Phe
385                 390                 395                 400
```

<210> SEQ ID NO 13
<211> LENGTH: 1404
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 13

```
atgggctggt cctgcatcat cctgtttctg gtggccaccg ccaccggtgt gcacagccag      60
gtgaccctga gggagagcgg ccccgccctg gtgaagccca cagaccctca ctctgacc      120
tgcaccgtga gcggcttcag cctgaccggc tctagcgtcc actgggtgag cagccccccc     180
ggcaagggcc tggagtggct gggcgtgatc tgggcaagcg ggggacgga ctacaactcg      240
gccctgatga gcaggctctc catcagcaag gacaccagcc ggaaccaggt ggtgctgacc     300
atgaccaaca tggaccccgt ggacaccgcc acctattact gcgccaggga ccctcccctcc    360
ggcctgctga ggctggacta ctggggcagg ggaacactag tgaccgtgtc cagcgccagc    420
accaagggcc ccagcgtgtt ccccctggcc ccagcagca gagcaccag cggcggcaca     480
gccgccctgg gctgcctggt gaaggactac ttccccgagc ccgtgaccgt gtcctggaac     540
agcggagccc tgaccagcgg cgtgcacacc ttccccgccg tgctgcagag cagcggcctg     600
tacagcctga gcagcgtggt gaccgtgccc agcagcagcc tgggcaccca gacctacatc     660
tgtaacgtga accacaagcc cagcaacacc aaggtggaca gcggggtgga gcccaagagc     720
tgtgacaaga cccacacctg cccccccctgc cctgccccg agctgctggg aggccccagc     780
gtgttcctgt tcccccccaa gcctaaggac accctgtaca tcaccagaga cccgaggtg     840
acctgtgtgg tggtggatgt gagccacgag gaccctgagg tgaagttcaa ctggtacgtg     900
gacggcgtgg aggtgcacaa tgccaagacc aagcccaggg aggagcagta caacagcacc     960
taccgggtgg tgtccgtgct gaccgtgctg caccaggatt ggctgaacgg caaggagtac    1020
aagtgtaagg tgtccaacaa ggccctgcct gccctatcg agaaaaccat cagcaaggcc    1080
aagggccagc ccagagagcc ccaggtgtac accctgcccc ctagcagaga ggagatgacc    1140
aagaaccagg tgtccctgac ctgcctggtg aagggcttct accccagcga catcgccgtg    1200
gagtgggaga gcaacggcca gcccgagaac aactacaaga ccaccccccc tgtgctggac    1260
agcgatggca gcttcttcct gtacagcaag ctgaccgtgg acaagagcag atggcagcag    1320
ggcaacgtgt tcagctgctc cgtgatgcac gaggccctgc acaatcacta cacccagaag    1380
agcctgagcc tgtcccctgg caag                                          1404
```

<210> SEQ ID NO 14
<211> LENGTH: 717
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 14

| | | | | | | |
|---|---|---|---|---|---|---|
| atgggctggt | cctgcatcat | cctgtttctg | gtggccaccg | ccaccggtgt | gcacagcgac | 60 |
| atcgtgatga | cccagtctcc | cgattcactg | gccgtgagcc | tgggcgagag | ggccaccatc | 120 |
| aactgcaaga | gcagccagag | cctcctgaac | agcggcaacc | agaagaacta | cctggcctgg | 180 |
| taccagcaga | aacccggcca | gccccccaag | ctgctgatct | atggcgcctc | caccagggag | 240 |
| agcggcgtgc | cagacaggtt | tagcggcagc | ggcagcggca | ccgacttcac | cctgacaatc | 300 |
| agcagcctgc | aggccgagga | cgtggccgtg | tactactgcc | agaacgtcca | cagcttcccc | 360 |
| ttcaccttcg | gcgggggaac | caagctggag | atcaagcgta | cggtggccgc | cccccagcgtg | 420 |
| ttcatcttcc | cccccagcga | tgagcagctg | aagagcggca | ccgccagcgt | ggtgtgtctg | 480 |
| ctgaacaact | tctaccccg | ggaggccaag | gtgcagtgga | aggtggacaa | tgccctgcag | 540 |
| agcggcaaca | gccaggagag | cgtgaccgag | caggacagca | aggactccac | ctacagcctg | 600 |
| agcagcaccc | tgaccctgag | caaggccgac | tacgagaagc | acaaggtgta | cgcctgtgag | 660 |
| gtgacccacc | agggcctgtc | cagccccgtg | accaagagct | tcaaccgggg | cgagtgc | 717 |

<210> SEQ ID NO 15
<211> LENGTH: 356
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 15

| | | | | | | |
|---|---|---|---|---|---|---|
| aggtgaccct | gagggagagc | ggccccgccc | tggtgaagcc | cacacagacc | ctcactctga | 60 |
| cctgcaccgt | gagcggcttc | agcctgaccg | gctctagcgt | ccactgggtg | aggcagcccc | 120 |
| ccggcaaggg | cctggagtgg | ctgggcgtga | tctgggcaag | cggggggacg | gactacaact | 180 |
| cggccctgat | gagcaggctc | tccatcagca | aggacaccag | ccggaaccag | gtggtgctga | 240 |
| ccatgaccaa | catggacccc | gtggacaccg | ccacctatta | ctgcgccagg | gaccctccct | 300 |
| ccggcctgct | gaggctggac | tactggggca | ggggaacact | agtgaccgtg | tccagc | 356 |

<210> SEQ ID NO 16
<211> LENGTH: 342
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 16

| | | | | | | |
|---|---|---|---|---|---|---|
| gacatcgtga | tgacccagtc | tcccgattca | ctggccgtga | gcctgggcga | gagggccacc | 60 |
| atcaactgca | agagcagcca | gagcctcctg | aacagcggca | accagaagaa | ctacctggcc | 120 |
| tggtaccagc | agaaacccgg | ccagcccccc | aagctgctga | tctatggcgc | ctccaccagg | 180 |
| gagagcggcg | tgccagacag | gtttagcggc | agcggcagcg | gcaccgactt | caccctgaca | 240 |
| atcagcagcc | tgcaggccga | ggacgtggcc | gtgtactact | gccagaacgt | ccacagcttc | 300 |
| cccttcacct | tcggcggggg | aaccaagctg | gagatcaagc | gt | | 342 |

<210> SEQ ID NO 17
<211> LENGTH: 1347
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 17

| caggtgaccc | tgagggagag | cggccccgcc | ctggtgaagc | ccacacagac | cctcactctg | 60 |
| acctgcaccg | tgagcggctt | cagcctgacc | ggctctagcg | tccactgggt | gaggcagccc | 120 |
| cccggcaagg | gcctggagtg | gctgggcgtg | atctgggcaa | gcgggggggac | ggactacaac | 180 |
| tcggccctga | tgagcaggct | ctccatcagc | aaggacacca | gccggaacca | ggtggtgctg | 240 |
| accatgacca | acatggaccc | cgtggacacc | gccacctatt | actgcgccag | ggaccctccc | 300 |
| tccggcctgc | tgaggctgga | ctactggggc | aggggaacac | tagtgaccgt | gtccagcgcc | 360 |
| agcaccaagg | gccccagcgt | gttccccctg | gcccccagca | gcaagagcac | cagcggcggc | 420 |
| acagccgccc | tgggctgcct | ggtgaaggac | tacttccccg | agcccgtgac | cgtgtcctgg | 480 |
| aacagcggag | ccctgaccag | cggcgtgcac | accttccccg | ccgtgctgca | gagcagcggc | 540 |
| ctgtacagcc | tgagcagcgt | ggtgaccgtg | cccagcagca | gcctgggcac | ccagacctac | 600 |
| atctgtaacg | tgaaccacaa | gcccagcaac | accaaggtgg | acaagcgggt | ggagcccaag | 660 |
| agctgtgaca | agacccacac | ctgcccccca | tgccctgccc | ccgagctgct | gggaggcccc | 720 |
| agcgtgttcc | tgttcccccc | caagcctaag | gacaccctgt | acatcaccag | agaacccgag | 780 |
| gtgacctgtg | tggtggtgga | tgtgagccac | gaggaccctg | aggtgaagtt | caactggtac | 840 |
| gtggacggcg | tggaggtgca | caatgccaag | accaagccca | gggaggagca | gtacaacagc | 900 |
| acctaccggg | tggtgtccgt | gctgaccgtg | ctgcaccagg | attggctgaa | cggcaaggag | 960 |
| tacaagtgta | aggtgtccaa | caaggccctg | cctgccccta | tcgagaaaac | catcagcaag | 1020 |
| gccaagggcc | agcccagaga | gccccaggtg | tacaccctgc | cccctagcag | agaggagatg | 1080 |
| accaagaacc | aggtgtccct | gacctgcctg | gtgaagggct | tctacccag | cgacatcgcc | 1140 |
| gtggagtggg | agagcaacgg | ccagcccgag | aacaactaca | agaccacccc | ccctgtgctg | 1200 |
| gacagcgatg | gcagcttctt | cctgtacagc | aagctgaccg | tggacaagag | cagatggcag | 1260 |
| cagggcaacg | tgttcagctg | ctccgtgatg | cacgaggccc | tgcacaatca | ctacacccag | 1320 |
| aagagcctga | gcctgtcccc | tggcaag | | | | 1347 |

<210> SEQ ID NO 18
<211> LENGTH: 660
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 18

| gacatcgtga | tgacccagtc | tcccgattca | ctggccgtga | gcctgggcga | gagggccacc | 60 |
| atcaactgca | agagcagcca | gagcctcctg | aacagcggca | accagaagaa | ctacctggcc | 120 |
| tggtaccagc | agaaacccgg | ccagcccccc | aagctgctga | tctatggcgc | ctccaccagg | 180 |
| gagagcggcg | tgccagacag | gtttagcggc | agcggcagcg | gcaccgactt | cacccctgaca | 240 |
| atcagcagcc | tgcaggccga | ggacgtggcc | gtgtactact | gccagaacgt | ccacagcttc | 300 |

```
ccctccacct tcggcggggg aaccaagctg gagatcaagc gtacggtggc cgccccagc    360 gtgttcatct tccccccag cgatgagcag ctgaagagcg gcaccgccag cgtggtgtgt    420
ctgctgaaca acttctaccc ccgggaggcc aaggtgcagt ggaaggtgga caatgccctg    480
cagagcggca acagccagga gagcgtgacc gagcaggaca gcaaggactc cacctacagc    540
ctgagcagca ccctgaccct gagcaaggcc gactacgaga agcacaaggt gtacgcctgt    600
gaggtgaccc caccgggcct gtccagcccc gtgaccaaga gcttcaaccg gggcgagtgc    660
```

<210> SEQ ID NO 19
<211> LENGTH: 19
<212> TYPE: PRT
<213> ORGANISM: Artificial Sequence
<220> FEATURE:
<223> OTHER INFORMATION: Amino acid sequence identified using molecular biology techniques.

<400> SEQUENCE: 19

```
Met Gly Trp Ser Cys Ile Ile Leu Phe Leu Val Ala Thr Ala Thr Gly
1               5                   10                  15

Val His Ser
```

<210> SEQ ID NO 20
<211> LENGTH: 19
<212> TYPE: PRT
<213> ORGANISM: Artificial Sequence
<220> FEATURE:
<223> OTHER INFORMATION: Amino acid sequence identified using molecular biology techniques.

<400> SEQUENCE: 20

```
Met Gly Trp Ser Cys Ile Ile Leu Phe Leu Val Ala Thr Ala Thr Gly
1               5                   10                  15

Val His Ser
```

<210> SEQ ID NO 21
<211> LENGTH: 11
<212> TYPE: PRT
<213> ORGANISM: Artificial Sequence
<220> FEATURE:
<223> OTHER INFORMATION: Amino acid sequence identified using molecular biology techniques.

<400> SEQUENCE: 21

```
Trp Gly Arg Gly Thr Leu Val Thr Val Ser Ser
1               5                   10
```